United States Patent
Shalitin et al.

(10) Patent No.: US 11,926,837 B2
(45) Date of Patent: Mar. 12, 2024

(54) COMPOSITIONS AND METHODS FOR CONTROLLING PLANT GROWTH

(71) Applicant: PLANTARC BIO LTD., Raanana (IL)

(72) Inventors: Dror Shalitin, Raanana (IL); Noam Grimberg, Kibutz Lehavot Haviva (IL)

(73) Assignee: PLANTARC BIO LTD., Raanana (IL)

( * ) Notice: Subject to any disclaimer, the term of this patent is extended or adjusted under 35 U.S.C. 154(b) by 0 days.

(21) Appl. No.: 17/683,747

(22) Filed: Mar. 1, 2022

(65) Prior Publication Data

US 2022/0186246 A1 Jun. 16, 2022

Related U.S. Application Data

(63) Continuation of application No. PCT/IL2020/050967, filed on Sep. 3, 2020.

(60) Provisional application No. 62/896,312, filed on Sep. 5, 2019.

(51) Int. Cl.
C12N 15/82 (2006.01)

(52) U.S. Cl.
CPC .. *C12N 15/8274* (2013.01); *C12Y 113/11027* (2013.01)

(58) Field of Classification Search
CPC .................................................. C12N 15/8274
See application file for complete search history.

(56) References Cited

U.S. PATENT DOCUMENTS

| | | | |
|---|---|---|---|
| 6,245,968 B1 * | 6/2001 | Boudec | C12N 15/8274 800/300 |
| 2002/0112260 A1 | 8/2002 | Schillinger et al. | |
| 2003/0233675 A1 | 12/2003 | Cao et al. | |
| 2015/0089684 A1 | 3/2015 | Abad et al. | |
| 2015/0159145 A1 * | 6/2015 | Poree | C12N 9/0069 800/300 |
| 2016/0244777 A1 | 8/2016 | Coffin | |
| 2017/0166918 A1 | 6/2017 | Dubald et al. | |

FOREIGN PATENT DOCUMENTS

WO 2015/138394 9/2015

OTHER PUBLICATIONS

Accinelli et al, Crop Protection (2014) 67:243-250.*
UniProt Accession No. A0A2T4APG0, integrated into UniProt on Jul. 18, 2018.*
Choudhury et al, Weeds—Journal of Asian-Pacific Weed Science Society (2019) 1:43-54.*
Jhala et al, Weed Technology (2022) 37:1-14.*
Choudhury, Partha P. et al., "Biodegradation of Topramezone by a *Trichoderma* isolate in soil", 2019, Weeds-Journal of the Asian-Pacific Weed Science Society, vol. 1, Issue No. 1, pp. 43-54.
Meher, Prabina Kumar et al, "HRGPred: Prediction of herbicide resistant genes With k-mer nucleotide compositional features and support vector machine", 2019, Scientific Reports, vol. 9:778, 16 pages.
Database NCBI, Apr. 26, 2018, hypothetical protein M431DRAFT_490592 [Trichoderma harzianurn CBS 226.95]. Genebank accession No. XP_024778642.1. (https://www.ncbi.nlm.nih.gov/protein/XP_024778642.1?report=genbank&log$=protalign&blast_rank=2&RID=Y417T8CS013).
International Search Report and Written Opinion of PCT/IL2020/050967, dated Dec. 24, 2020.
Database UniProt (2019) Accession No. AOA2N1LMP8.
4-hydroxyphenyloyruvate dioxygenase [Colletotriehum orbiculare MAFF 240422] GenBank Accession No. TDZ23002.1.
Hypothetical protein M431DRAFT_490592 [Trichoderma harzianum CBS 226.95] NCBI Accession No. XP_024778642.1.

* cited by examiner

*Primary Examiner* — Mykola V. Kovalenko
(74) *Attorney, Agent, or Firm* — WENDEROTH, LIND & PONACK, L.L.P.

(57) ABSTRACT

A plant containing a nucleic acid sequence encoding a protein conferring resistance to a herbicide including one or more HPPD inhibitors, wherein the nucleic acid sequence encodes for a modified and/or exogenous HPPD enzyme.

5 Claims, 12 Drawing Sheets
(10 of 12 Drawing Sheet(s) Filed in Color)
Specification includes a Sequence Listing.

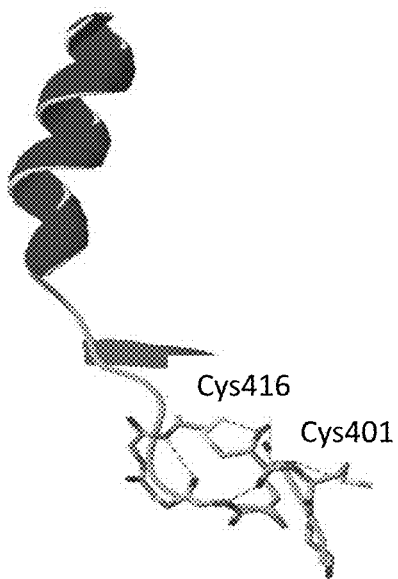
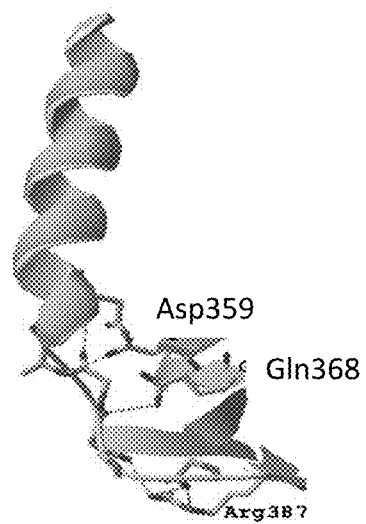
FIG. 7A
FIG. 7B
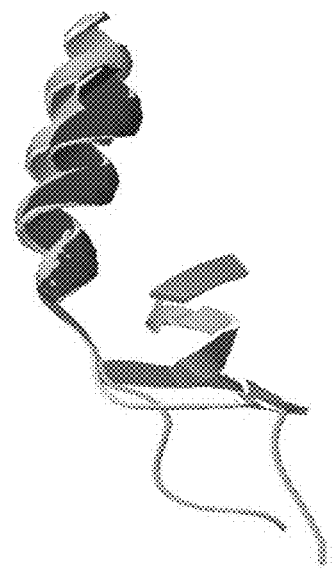
FIG. 7C

GmHPPD.1

GmHPPD.5

GmHPPD.3

GmHPPD

GmHPPD.4

EGFP

COMPOSITIONS AND METHODS FOR CONTROLLING PLANT GROWTH

FIELD OF INVENTION

The present invention relates to plants, plant cells, tissues, and seeds that have been genetically modified to express a fungus derived HPPD or variant thereof and/or to plants in which the endogenous HPPD has been edited (e.g. by CRISPR/Cas technology, TALLEN, Zink-finger etc.) to include fungus derived motifs and/or mutations, thereby providing plants with an HPPD that confers resistance or tolerance to HPPD inhibitors.

BACKGROUND OF THE INVENTION

Weeds have been the major biotic cause of crop yield loses since the origin of agriculture. Weeds compete with crops for space, nutrients, water and light, and the potential of weed damages is estimated as 34% loss of crop yield, on average, world-wide [Oerke, E-C., 2006].

Herbicides are the most commonly used and effective weed control tools. Due to the intense selection pressure exerted by herbicides, herbicide resistance is constantly growing and, as of 2016 there are over 470 weed biotypes currently identified as being herbicide resistant to one or more herbicides by The International Survey of Herbicide Resistant Weeds (weedscience.org). Weeds compete with productive crops or pasture, ultimately converting productive land into unusable scrub. Moreover, weeds can be poisonous, distasteful, produce burrs, thorns or otherwise interfere with the use and management of desirable plants by contaminating harvests or interfering with livestock.

4-Hydroxyphenylpyruvate dioxygenase (HPPD) inhibitors (HPPD inhibitors) are a class of herbicides that inhibit plant growth by blocking HPPD, an enzyme catalyzes the conversion of p-hydroxyphenylpyruvate (HPP) into homogentisate (HGA), a key precursor of α-tocopherol and plastoquinone in plant's tyrosine degradation pathway. Preventing the breakdown of tyrosine causes three major impacts on the treated plant: excess of tyrosine which stunts growth; oxidative damage due to lack of tocopherols (vitamin E); and chlorophyll destruction due to lack of carotenoids. Plants turn white due to a complete loss of chlorophyll, which has led compounds of this class to be classified as a "bleaching herbicide".

Herbicides that act by inhibiting HPPD are well known, and include isoxazoles, diketonitriles, triketones, and pyrazolinates (Hawkes "Hydroxyphenylpyruvate Dioxygenase (HPPD)—The Herbicide Target." In Modern Crop Protection Compounds. Eds. Kramer and Schirmer. Weinheim, Germany: Wiley-VCH, 2007. Ch. 4.2, pp. 211-220).

HPPD inhibitors were first brought to market in 1980, although their mechanism of action was not understood until the late 1990s. They were originally used primarily in Japan in rice production, but since the late 1990s have been used in Europe and North America for corn, soybeans, and cereals, and since the 2000s have become more important as weeds have become resistant to glyphosate and other herbicides.

Specifically, tembotrione, mesotrione and isoxaflutole provide powerful residual control of more than 65 grass and broadleaf weeds with unsurpassed crop safety in all types of corn. It is also effective on the toughest broadleaf weeds, including glyphosate-, PPO-, ALS- and dicamba-resistant weeds.

HPPD inhibitors, can only be used in crops if the crop is resistant/tolerant to the herbicide. The treatment of plants susceptible to HPPD inhibition, such as, but not limited to, broad-leaf plants, is thus limited. It has been of particular difficulty to achieve a resistance that provides commercial levels of tolerance to at least some desirable HPPD-inhibitor herbicides. Accordingly, new methods and compositions for conferring HPPD herbicide tolerance upon various crops and crop varieties are needed.

SUMMARY OF THE INVENTION

The present invention provides plants, plant cells, tissues, and seeds that have been genetically modified with a fungus derived HPPD or variant thereof and/or to plants in which the endogenous HPPD has been edited (e.g. by CRISPR/Cas technology, TALLEN, Zink-finger etc.) to include fungus derived motifs and/or mutations, thereby providing plants with an HPPD that confers resistance or tolerance to herbicides.

Compositions and methods for conferring hydroxyphenyl pyruvate dioxygenase (HPPD) herbicide resistance or tolerance to plants are provided. The compositions include nucleotide and amino acid sequences for HPPD polypeptides. In certain embodiments, the polypeptides of the invention are fungal HPPDs or HPPD derivatives that when expressed in plants confer their resistance or tolerance to herbicides that inhibit HPPD.

According to some embodiments, the HPPD, expressed in the plant, comprises one or more of the amino acid sequences set forth in SEQ ID NO: 9 (EAVYNKAVAEGA), SEQ ID NO: 10 (VAEGAIAVQGP), SEQ ID NO: 11 (FHRFWSVDD), SEQ ID NO: 12 (DDSQICTEFS), SEQ ID NO: 13 (VEFINVPTTYY), SEQ ID NO: 14 (TYYDTMRQRLKT), SEQ ID NO: 15 (QRLNILID), SEQ ID NO: 16 (IDYDEAGY), SEQ ID NO: 17 (EIIQRNNF), SEQ ID NO: 18 (NNFEGFG), SEQ ID NO: 19 (AVICTYGDT), SEQ ID NO: 20 (DTTHTLINR), SEQ ID NO: 21 (EMVSACA), SEQ ID NO: 22 (CAFYEQC), SEQ ID NO: 23 (GFGAGNF), SEQ ID NO: 24 (TPDNFA); SEQ ID NO: 25 (DDVFAAAVQNGA), SEQ ID NO: 26 (VQNGAVAVSQP), SEQ ID NO: 27 (FHRFRSVDD), SEQ ID NO: 28 (DDKDICTDYS), SEQ ID NO: 29 (VEFIKVPPTYY), SEQ ID NO: 30 (TYYDNMWMRLKK), SEQ ID NO: 31 (KKLDILID), SEQ ID NO: 32 (IDFDEGGY), SEQ ID NO: 33 (NNFSGFG), SEQ ID NO: 34 (ATIRTYGDT), SEQ ID NO: 35 (DTTHTLIQR), SEQ ID NO: 36 (CAYYEKV), SEQ ID NO: 37 (QSDNLP) or any combination thereof. Each possibility is a separate embodiment.

According to some embodiments, the HPPD, expressed in the plant, comprises one or more of the amino acid sequences set forth in SEQ ID NO: 9 (EAVYNKAVAEGA), SEQ ID NO: 10 (VAEGAIAVQGP), SEQ ID NO: 11 (FHRFWSVDD), SEQ ID NO: 12 (DDSQICTEFS), SEQ ID NO: 13 (VEFINVPTTYY), SEQ ID NO: 14 (TYYDTMRQRLKT), SEQ ID NO: 15 (QRLNILID), SEQ ID NO: 16 (IDYDEAGY), SEQ ID NO: 17 (EIIQRNNF), SEQ ID NO: 18 (NNFEGFG), SEQ ID NO: 19 (AVICTYGDT), SEQ ID NO: 20 (DTTHTLINR), SEQ ID NO: 21 (EMVSACA), SEQ ID NO: 22 (CAFYEQC), SEQ ID NO: 23 (GFGAGNF), SEQ ID NO: 24 (TPDNFA) or any combination thereof. Each possibility is a separate embodiment.

According to some embodiments, the HPPD, expressed in the plant, comprises one or more of the amino acid sequences set forth in SEQ ID NO: 25 (DDVFAAAVQNGA), SEQ ID NO: 26 (VQNGAVAVSQP), SEQ ID NO: 27 (FHRFRSVDD), SEQ ID NO: 28

(DDKDICTDYS), SEQ ID NO: 29 (VEFIKVPPTYY), SEQ ID NO: 30 (TYYDNMWMRLKK), SEQ ID NO: 31 (KKLDILID), SEQ ID NO: 32 (IDFDEGGY), SEQ ID NO: 33 (NNFSGFG), SEQ ID NO: 34 (ATIRTYGDT), SEQ ID NO: 35 (DTTHTLIQR), SEQ ID NO: 36 (CAYYEKV), SEQ ID NO: 37 (QSDNLP) or any combination thereof. Each possibility is a separate embodiment.

According to some embodiments, the HPPD, expressed in the plant, comprises all of the amino acid sequences set forth in SEQ ID NOs: 9-24 and/or all of the amino acid sequences set forth in SEQ ID NOs: 25-37.

According to some embodiments, the amino acid sequences set forth in SEQ ID NOs: 9-37 constitute motifs. As used herein, the term "motif" refers to an amino acid sequence which can form secondary structure elements that either have a particular functional significance or define a portion of an independently folded domain, such as, for example, a loop structure. According to some embodiments, the HPPD, expressed in the plant, comprises one or more motifs or is genetically modified to express one or more motifs or is genetically edited to express one or more motifs. According to some embodiments, the one or more motifs comprises or consists of an amino acid sequence set forth in any one or more of SEQ ID NOs: 9-37 or 9-24. Each possibility is a separate embodiment. According to some embodiments, the HPPD SEQ ID NOs: 9-24 form 9 motifs.

According to some embodiments, motif 1-9 are derived from SEQ ID NO: 1.

According to some embodiments, motif 1 includes SEQ ID NO: 9 and 10 or modified versions thereof. According to some embodiments, motif 1 has the amino acid sequence set forth in SEQ ID NO: 38 (EAVYNKAVAEGAIAVQGP).

According to some embodiments, motif 2 includes SEQ ID NO: 11 and 12 or modified versions thereof. According to some embodiments, motif 2 has the amino acid sequence set forth in SEQ ID NO: 39 (FHRFWSVDDSQICTEFS).

According to some embodiments, motif 3 includes SEQ ID NO: 13 and 14 or modified versions thereof. According to some embodiments, motif 3 has the amino acid sequence set forth in SEQ ID NO: 40 (VEFINVPT-TYYDTMRQRLKT).

According to some embodiments, motif 4 includes SEQ ID NO: 15 and 16 or modified versions thereof. According to some embodiments, motif 4 has the amino acid sequence set forth in SEQ ID NO: 41 (QRLNILIDYDEAGY).

According to some embodiments, motif 5 includes SEQ ID NO: 17 and 18 or modified versions thereof. According to some embodiments, motif 5 has the amino acid sequence set forth in SEQ ID NO: 42 (EIIQRNNFEGFG).

According to some embodiments, motif 6 includes SEQ ID NO: 19 and 20 or modified versions thereof. According to some embodiments, motif 6 has the amino acid sequence set forth in SEQ ID NO: 43 (AVICTYGDTTHTLINR).

According to some embodiments, motif 7 includes SEQ ID NO: 21 and 22 or modified versions thereof. According to some embodiments, motif 7 has the amino acid sequence set forth in SEQ ID NO: 44 (EMVSACAFYEQC).

According to some embodiments, motif 8 includes SEQ ID NO: 23 or modified versions thereof. According to some embodiments, motif 8 has the amino acid sequence set forth in SEQ ID NO: 45 (GFGAGNF).

According to some embodiments, motif 9 includes SEQ ID NO: 24 or modified versions thereof. According to some embodiments, motif 9 has the amino acid sequence set forth in SEQ ID NO: 46 (TPDNFA).

According to some embodiments, the HPPD, expressed in the plant, comprises at least one, at least two, at least three, at least four or more of the amino acid sequences set forth in SEQ ID NOs: 38-46. According to some embodiments, the HPPD, expressed in the plant, comprises all of the amino acid sequences set forth in SEQ ID NOs: 38-46.

According to some embodiments, motif 1-9 are derived from SEQ ID NO: 3.

According to some embodiments, motif 1 includes SEQ ID NO: 25 and 26 or modified versions thereof. According to some embodiments, motif 1 has the amino acid sequence set forth in SEQ ID NO: 47 (DDVFAAAVQNGAVAVSQP).

According to some embodiments, motif 2 includes SEQ ID NO: 27 and 28 or modified versions thereof. According to some embodiments, motif 2 has the amino acid sequence set forth in SEQ ID NO: 48 (FHRFRSVDDKDICTDYS).

According to some embodiments, motif 3 includes SEQ ID NO: 29 and 30 or modified versions thereof. According to some embodiments, motif 3 has the amino acid sequence set forth in SEQ ID NO: 49 (VEFIKVPP-TYYDNMWMRLKK).

According to some embodiments, motif 4 includes SEQ ID NO: 31 and 32 or modified versions thereof. According to some embodiments, motif 4 has the amino acid sequence set forth in SEQ ID NO: 50 (KKLDILIDFDEGGY).

According to some embodiments, motif 5 includes SEQ ID NO: 33 or modified versions thereof. According to some embodiments, motif 5 has the amino acid sequence set forth in SEQ ID NO: 51 (EIIQRNNFSGFG).

According to some embodiments, motif 6 includes SEQ ID NO: 34 and 35 or modified versions thereof. According to some embodiments, motif 6 has the amino acid sequence set forth in SEQ ID NO: 52 (ATIRTYGDTTHTLIQR).

According to some embodiments, motif 7 includes SEQ ID NO: 36 or modified versions thereof. According to some embodiments, motif 7 has the amino acid sequence set forth in SEQ ID NO: 53 (EMEKVCAYYEKV).

According to some embodiments, motif 9 includes SEQ ID NO: 37 or modified versions thereof. According to some embodiments, motif 9 has the amino acid sequence set forth in SEQ ID NO: 54 (QSDNLP).

According to some embodiments, the HPPD, expressed in the plant, comprises at least a fungal derived motif 1. According to some embodiments, the fungal derived motif 1 may include any one of the SEQ ID NOs set forth in SEQ ID NOs: 9, 10, 25, 26, 38, 47, 119-128 or 159-168. Each possibility is a separate embodiment.

According to some embodiments, the HPPD, expressed in the plant, comprises at least a fungal derived motif 2. According to some embodiments, the fungal derived motif 2 may include any one of the SEQ ID Nos set forth in SEQ ID NOs: 11, 12, 27, 28, 39, 48, 129-134 or 169-174. Each possibility is a separate embodiment.

According to some embodiments, the HPPD, expressed in the plant, comprises at least a fungal derived motif 3. According to some embodiments, the fungal derived motif 3 may include any one of the SEQ ID Nos set forth in SEQ ID NOs: 13, 14, 29, 30, 40, 49, 135-142 or 175-182. Each possibility is a separate embodiment.

According to some embodiments, the HPPD, expressed in the plant, comprises at least a fungal derived motif 4. According to some embodiments, the fungal derived motif 4 may include any one of the SEQ ID Nos set forth in SEQ ID NOs: 15, 16, 31, 32, 41, 50, 143, 144, 156 or 183-185. Each possibility is a separate embodiment.

According to some embodiments, the HPPD, expressed in the plant, comprises at least a fungal derived motif 5. According to some embodiments, the fungal derived motif 5 may include any one of the SEQ ID Nos set forth in SEQ ID NOs: 17, 18, 33, 42, 51, 145-151, 186-191 or 196. Each possibility is a separate embodiment.

According to some embodiments, the HPPD, expressed in the plant, comprises at least a fungal derived motif 6. According to some embodiments, the fungal derived motif 6 may include any one of the SEQ ID Nos set forth in SEQ ID NOs: 19, 20, 34, 35, 43, 52, 152, 157, 192 or 197. Each possibility is a separate embodiment.

According to some embodiments, the HPPD, expressed in the plant, comprises at least a fungal derived motif 7. According to some embodiments, the fungal derived motif 7 may include any one of the SEQ ID Nos set forth in SEQ ID Nos 21, 22, 36, 44, 53, 153, 154, 193 or 194. Each possibility is a separate embodiment.

According to some embodiments, the HPPD, expressed in the plant, comprises at least a fungal derived motif 8. According to some embodiments, the fungal derived motif 8 may include any one of the SEQ ID Nos set forth in SEQ ID Nos 23, 45, 158 or 198. Each possibility is a separate embodiment.

According to some embodiments, the HPPD, expressed in the plant, comprises at least a fungal derived motif 9. According to some embodiments, the fungal derived motif 9 may include any one of the SEQ ID Nos set forth in SEQ ID Nos 24, 37, 46, 54, 155 or 195. Each possibility is a separate embodiment.

According to some embodiments, the term "fungal derived motif" refers to a motif coming from a fungus and/or to an endogenous motif at least partially modified to mimic the equivalent motif of the fungus.

According to some embodiments, the plant is a dicot plant and wherein the dicot plant has been genetically modified to express an HPPD enzyme encoded by an amino acid sequence having any of the amino acid sequences set forth in SEQ ID NO: 119-158. Each possibility is a separate embodiment.

According to some embodiments, the plant is a dicot plant and wherein the dicot plant has been genetically modified to express an HPPD enzyme encoded by an amino acid sequence having any of the amino acid sequences set forth in SEQ ID NO: 159-198. Each possibility is a separate embodiment.

According to some embodiments, the HPPD enzyme comprises 9 helices, wherein helix 7 of the modified HPPD enzyme disclosed herein is altered. Without being bound by any theory the altered helix 7 results in a modified active site and thus in lower affinity to HPPD inhibitors.

In particular embodiments, the HPPD, expressed in the plant, comprises an amino acid sequence set forth in SEQ ID NO: 1, 3 or 5-8 or polypeptides having at least about 99, 98, 97, 96, 95, 94, 93, 92, 91 or 90% sequence identity to SEQ ID NO: 1, 3, or 5-8 that exhibit HPPD enzyme activity. According to some embodiments, the nucleotide sequences encoding the HPPD comprises the nucleotide sequences set forth in SEQ ID NO: 2, 4 or parts or homologs thereof encoding the HPPDs having the amino acid sequence set forth in SEQ ID NO: 1, 3, or 5-8.

According to some embodiments, the HPPD, expressed in the plant includes a sequence having at least 80%, at least 85%, at least 90%, at least 95% or at least 98% sequence homology to a sequence set forth in a referred to sequence ID NO. Each possibility is a separate embodiment. As a non-limiting example, the HPPD, expressed in the plant may include an amino acid sequence having at least 80%, at least 85%, at least 90%, at least 95% or at least 98% homology to any of the amino acid sequences set forth in SEQ ID NOs: 9-54.

According to some embodiments, the herein disclosed HPPD, when expressed in plants, confers resistance to a variety of herbicides that inhibit HPPD, such as at least two different HPPDs, at least three HPPDs or at least four HPPDs.

According to some embodiments, the HPPD protein may be a non-naturally occurring modified HPPD protein. According to some embodiments, the HPPD protein may be a synthetic protein. According to some embodiments, the HPPD protein may be an HPPD mutant. According to some embodiments, the HPPD protein may be an HPPD protein modified by gene editing e.g. using CRISPR-CAS technologies.

According to some embodiments, the HPPD protein may be a modified version of the HPPD protein endogenous to *G. max* (Gm_HPPD) set forth in SEQ ID NO: 118, wherein the modified version has HPPD enzymatic activity and comprises the amino acid sequence set forth in SEQ ID NO: 55 (EAAFSASVAKGA), wherein the first F is replaced with any other amino acid, particularly with Y; and/or wherein the first S is replaced with any other amino acid, particularly with N; and/or wherein the third A is replaced with any other amino acid, particularly with K; and/or wherein the second S is replaced with any other amino acid, particularly with A; and/or wherein the first K is replaced with any other amino acid, particularly with E.

According to some embodiments, the HPPD protein may be a modified version of the HPPD protein endogenous to *G. max* (Gm_HPPD), wherein the modified version has HPPD enzymatic activity and comprises the amino acid sequence set forth in SEQ ID NO: 56 (VAKGAEPASPP), wherein the first K is replaced with any other amino acid, particularly with E; and/or wherein the first E is replaced with any other amino acid, particularly with I; and/or wherein the first P is replaced with any other amino acid, particularly with A; and/or wherein the first S is replaced with any other amino acid, particularly with Q; and/or wherein the second P is replaced with any other amino acid, particularly with G.

According to some embodiments, the HPPD protein may be a modified version of the HPPD protein endogenous to *G. max* (Gm_HPPD), wherein the modified version has HPPD enzymatic activity and comprises the amino acid sequence set forth in SEQ ID NO: 57 (FHEFAEFTA), wherein the first A is replaced with any other amino acid, particularly with W or R; and/or wherein the first T is replaced with any other amino acid, particularly with D; and/or wherein the second A is replaced with any other amino acid, particularly with D.

According to some embodiments, the HPPD protein may be a modified version of the HPPD protein endogenous to *G. max* (Gm_HPPD), wherein the modified version has HPPD enzymatic activity and comprises the amino acid sequence set forth in SEQ ID NO: 58 (TAEDVGTSES), wherein the first T is replaced with any other amino acid, particularly with D; and/or wherein the first A is replaced with any other amino acid, particularly with D; and/or wherein the first E is replaced with any other amino acid, particularly with F or Y.

According to some embodiments, the HPPD protein may be a modified version of the HPPD protein endogenous to *G. max* (Gm_HPPD), wherein the modified version has HPPD enzymatic activity and comprises the amino acid sequence set forth in SEQ ID NO: 59 (FEFMPSPPPTYY), wherein the first M is replaced with any other amino acid, particularly with I; and/or wherein the first P is replaced with any other amino acid, particularly with N; and/or wherein the first S is replaced with any other amino acid, particularly with V; and/or wherein the third P is replaced with any other amino acid, particularly with G or T; and/or wherein the fourth P is replaced with any other amino acid, particularly with G or removed.

According to some embodiments, the HPPD protein may be a modified version of the HPPD protein endogenous to *G. max* (Gm_HPPD), wherein the modified version has HPPD enzymatic activity and comprises the amino acid sequence set forth in SEQ ID NO: 60 (TYYANLHNRA), wherein the first A is replaced with any other amino acid, particularly with D; and/or wherein the first H is replaced with any other amino acid, particularly with R; and/or wherein the second N is replaced with any other amino acid, particularly with L.

According to some embodiments, the HPPD protein may be a modified version of the HPPD protein endogenous to *G. max* (Gm_HPPD), wherein the modified version has HPPD enzymatic activity and comprises the amino acid sequence set forth in SEQ ID NO: 61 (EELGILVD), wherein the first G is replaced with any other amino acid, particularly with N or D.

According to some embodiments, the HPPD protein may be a modified version of the HPPD protein endogenous to *G. max* (Gm_HPPD), wherein the modified version has HPPD enzymatic activity and comprises the amino acid sequence set forth in SEQ ID NO: 62 (VDRDDQGT), wherein the first R is replaced with any other amino acid, particularly with Y or F; and/or wherein the first Q is replaced with any other amino acid, particularly with A or G.

According to some embodiments, the HPPD protein may be a modified version of the HPPD protein endogenous to *G. max* (Gm_HPPD), wherein the modified version has HPPD enzymatic activity and comprises the amino acid sequence set forth in SEQ ID NO: 63 (EIIQRIGCM), wherein the third I is replaced with any other amino acid, particularly with N; and/or wherein the first G is replaced with any other amino acid, particularly with N; and/or wherein the first C is replaced with any other amino acid, particularly with F; and/or wherein the first M is replaced with any other amino acid, particularly with G or removed.

According to some embodiments, the HPPD protein may be a modified version of the HPPD protein endogenous to *G. max* (Gm_HPPD), wherein the modified version has HPPD enzymatic activity and comprises the amino acid sequence set forth in SEQ ID NO: 64 (CMVEDEEGK), wherein the first C is replaced with any other amino acid, particularly with F; and/or wherein all the amino acids but the first C are replaced with any other amino acid in particular with G or removed.

According to some embodiments, the HPPD protein may be a modified version of the HPPD protein endogenous to *G. max* (Gm_HPPD), wherein the modified version has HPPD enzymatic activity and comprises the amino acid sequence set forth in SEQ ID NO: 65 (GKVYQKGA), wherein all the amino acids are replaced with any other amino acid in particular with G or removed.

According to some embodiments, the HPPD protein may be a modified version of the HPPD protein endogenous to *G. max* (Gm_HPPD), wherein the modified version has HPPD enzymatic activity and comprises the amino acid sequence set forth in SEQ ID NO: 66 (YQKGACGGFG), wherein the first six amino acids are replaced with any other amino acid in particular with G or removed; and/or wherein the second G is replaced with any other amino acid, particularly with E or S.

According to some embodiments, the HPPD protein may be a modified version of the HPPD protein endogenous to *G. max* (Gm_HPPD), wherein the modified version has HPPD enzymatic activity and comprises the amino acid sequence set forth in SEQ ID NO: 67 (AEVRLYGDV), wherein the first E is replaced with any other amino acid, particularly with T or V.

According to some embodiments, the HPPD protein may be a modified version of the HPPD protein endogenous to *G. max* (Gm_HPPD), wherein the modified version has HPPD enzymatic activity and comprises the amino acid sequence set forth in SEQ ID NO: 68 (DVVLRYVSY), wherein the first Y is replaced with any other amino acid, particularly with F.

According to some embodiments, the HPPD protein may be a modified version of the HPPD protein endogenous to *G. max* (Gm_HPPD), wherein the modified version has HPPD enzymatic activity and comprises the amino acid sequence set forth in SEQ ID NO: 69 (ELAPAVR), wherein the first P is replaced with any other amino acid, particularly with S or K.

According to some embodiments, the HPPD protein may be a modified version of the HPPD protein endogenous to *G. max* (Gm_HPPD), wherein the modified version has HPPD enzymatic activity and comprises the amino acid sequence set forth in SEQ ID NO: 70 (VRYLKGF), wherein the first Y is replaced with any other amino acid, particularly with F.

According to some embodiments, the HPPD protein may be a modified version of the HPPD protein endogenous to *G. max* (Gm_HPPD), wherein the modified version has HPPD enzymatic activity and comprises the amino acid sequence set forth in SEQ ID NO: 71 (GFGKGNF), wherein the first K is replaced with any other amino acid, particularly with A.

According to some embodiments, the HPPD protein may be a modified version of the HPPD protein endogenous to *G. max* (Gm_HPPD), wherein the modified version has HPPD enzymatic activity and comprises the amino acid sequence set forth in SEQ ID NO: 72 (FVRTNP), wherein the first R is replaced with any other amino acid, particularly with A, D or Q.

According to some embodiments, the HPPD protein may be a modified version of an endogenous HPPD protein of a dicot plant, wherein a motif of the endogenous HPPD protein has the consensus sequence set forth in SEQ ID NO: 73 ((E,R)XAF(S,T)(A,I,T)SVX(K,N,H)GA—wherein X may be any amino acid) and, wherein the modified version has HPPD enzymatic activity and comprises the amino acid sequence set forth in SEQ ID NO: 73, wherein the F at the forth position is replaced with any other amino acid, particularly with Y, as set forth in SEQ ID NO: 119 ((E,R)XAY(S,T)(A,I,T)SVX(K,N,H)GA); and/or wherein the amino acid (S,T) at the fifth position is replaced with any other amino acid, particularly with N, as set forth in SEQ ID NO: 120 ((E,R)XAFN(A,I,T)SVX(K,N,H)GA); and/or wherein the amino acid (A,I,T) at the sixth position is replaced with any other amino acid, particularly with K, as set forth in SEQ ID NO: 121 ((E,R)XAF(S,T)KSVX(K,N,H)GA); and/or wherein the amino acid S at the seventh position is replaced with any other amino acid, particularly with A, as set forth in SEQ ID NO: 122 ((E,R)XAF(S,T)(A,I,T)AVX(K,N,H)GA); and/or wherein the amino acid (K,N,H) at the tenth position is replaced with any other amino acid, particularly with E, as set forth in SEQ ID NO: 123 ((E,R)XAF(S,T)(A,I,T)SVXEGA).

According to some embodiments, the HPPD protein may be a modified version of an endogenous HPPD protein of a dicot plant, wherein a motif of the endogenous HPPD protein has the consensus sequence set forth in SEQ ID NO: 74 (VX(K,N,H)GAEP(A,S)S(P,E)P)—wherein X may be any amino acid) and, wherein the modified version has HPPD enzymatic activity and comprises the amino acid sequence set forth in SEQ ID NO: 74, wherein the amino acid (K,N,H) at the third position is replaced with any other amino acid, particularly with E, as set forth in SEQ ID NO: 124 (VXEGAEP(A,S)S(P,E)P); and/or wherein the amino acid E at the sixth position is replaced with any other amino acid, particularly with I, as set forth in SEQ ID NO: 125 (VX(K,N,H)GAIP(A,S)S(P,E)P); and/or wherein the amino acid P at the seventh position is replaced with any other amino acid, particularly with A, as set forth in SEQ ID NO: 126 (VX(K,N,H)GAEA(A,S)S(P,E)P); and/or wherein the amino acid S at the nineth position is replaced with any other amino acid, particularly with Q, as set forth in SEQ ID NO: 127 (VX(K,N,H)GAEP(A,S)Q(P,E)P); and/or wherein the amino acid (P,E) at the tenth position is replaced with any other amino acid, particularly with G, as set forth in SEQ ID NO: 128 (VX(K,N,H)GAEP(A,S)SGP).

According to some embodiments, the HPPD protein may be a modified version of an endogenous HPPD protein of a dicot plant, wherein a motif HPPD protein has the consensus sequence set forth in SEQ ID NO: 75 (FH(E,Q)FAEFT(A, T)) and, wherein the modified version of the endogenous has HPPD enzymatic activity and comprises the amino acid sequence set forth in SEQ ID NO: 75, wherein the amino acid A at the fifth position is replaced with any other amino acid, particularly with W or R, as set forth in SEQ ID NO: 129 (FH(E,Q)F(W,R)EFT(A,T)); and/or wherein the amino acid T at the eight position is replaced with any other amino acid, particularly with D, as set forth in SEQ ID NO: 130 (FH(E,Q)FAEFD(A,T)); and/or wherein the amino acid (A,T) at the tenth position is replaced with any other amino acid, particularly with D, as set forth in SEQ ID NO: 131 (FH(E,Q)FAEFTD).

According to some embodiments, the HPPD protein may be a modified version of an endogenous HPPD protein of a dicot plant, wherein a motif HPPD protein has the consensus sequence set forth in SEQ ID NO: 76 (T(A,T)(E,D)DVGT (A,S)ES) and, wherein the modified version of the endogenous has HPPD enzymatic activity and comprises the amino acid sequence set forth in SEQ ID NO: 76, wherein the amino acid T at the first position is replaced with any other amino acid, particularly with D, as set forth in SEQ ID NO: 132 (D(A,T)(E,D)DVGT(A,S)ES); and/or wherein the amino acid (A,T) at the second position is replaced with any other amino acid, particularly with D, as set forth in SEQ ID NO: 133 (TD(E,D)DVGT(A,S)ES); and/or wherein the amino acid E at the ninth position is replaced with any other amino acid, particularly with F or Y, as set forth in SEQ ID NO: 134 (T(A,T)(E,D)DVGT(A,S)(F,Y)S).

According to some embodiments, the HPPD protein may be a modified version of an endogenous HPPD protein of a dicot plant, wherein a motif of the endogenous HPPD protein has the consensus sequence set forth in SEQ ID NO: 77 (F(E,D)FMPSPP(P,V)TYY) and, wherein the modified version has HPPD enzymatic activity and comprises the amino acid sequence set forth in SEQ ID NO: 77, wherein the amino acid M at the fourth position is replaced with any other amino acid, particularly with I, as set forth in SEQ ID NO: 135 (F(E,D)FIPSPP(P,V)TYY); and/or wherein the amino acid P at the fifth position is replaced with any other amino acid, particularly with N, as set forth in SEQ ID NO: 136 (F(E,D)FMNSPP(P,V)TYY); and/or wherein the amino acid S at the sixth position is replaced with any other amino acid, particularly with V, as set forth in SEQ ID NO: 137 (F(E,D)FMPVPP(P,V)TYY); and/or wherein the amino acid P at the eighth position is replaced with any other amino acid, particularly with G or T, as set forth in SEQ ID NO: 138 (F(E,D)FMPSP(G,T)(P,V)TYY); and/or wherein the amino acid (P,V) at the nineth position is replaced with any other amino acid, particularly with G or removed, as set forth in SEQ ID NO: 139 (F(E,D)FMPSPPGTYY) and SEQ ID NO: 140 (F(E,D)FMPSPPTYY), respectively.

According to some embodiments, the HPPD protein may be a modified version of an endogenous HPPD protein of a dicot plant, wherein a motif of the endogenous HPPD protein has the consensus sequence set forth in SEQ ID NO: 78 (TYYX(N,K)L(H,K,R)X(A,G)L—wherein X may be any amino acid) and, wherein the modified version has HPPD enzymatic activity and comprises the amino acid sequence set forth in SEQ ID NO: 78, wherein the amino acid at the fourth position is replaced with any other amino acid, particularly with D, as set forth in SEQ ID NO: 141 (TYYD(N,K)L(H,K,R)X(A,G)L); and/or wherein the amino acid at the eighth position is replaced with any other amino acid, particularly with L, as set forth in SEQ ID NO: 142 (TYYX(N,K)L(H,K,R)L(A,G)L).

According to some embodiments, the HPPD protein may be a modified version of an endogenous HPPD protein of a dicot plant, wherein a motif of the endogenous HPPD protein has the consensus sequence set forth in SEQ ID NO: 79 (VD(R,K)DDQGT) and, wherein the modified version has HPPD enzymatic activity and comprises the amino acid sequence set forth in SEQ ID NO: 79, wherein the amino acid (R,K) at the third position is replaced with any other amino acid, particularly with F or Y, as set forth in SEQ ID NO: 143 (VD(F,Y)DDQGT); and/or wherein the amino acid Q at the sixth position is replaced with any other amino acid, particularly with A or G, as set forth in SEQ ID NO: 144 (VD(R,K)DD(A,G)GT).

According to some embodiments, the HPPD protein may be a modified version of an endogenous HPPD protein of a dicot plant, wherein a motif of the endogenous HPPD protein has the consensus sequence set forth in SEQ ID NO: 80 (EIIQR(I,V)GCM) and, wherein the modified version has HPPD enzymatic activity and comprises the amino acid sequence set forth in SEQ ID NO: 80, wherein the amino acid amino acid (I,V) at the sixth position is replaced with any other amino acid, particularly with N, as set forth in SEQ ID NO: 145 (EIIQRNGCM); and/or wherein the amino acid G at the seventh position is replaced with any other amino acid, particularly with N, as set forth in SEQ ID NO: 146 (EIIQR(I,V)NCM); and/or wherein the amino acid C at the eighth position is replaced with any other amino acid, particularly with F, as set forth in SEQ ID NO: 147 (EIIQR (I,V)GFM); and/or wherein the amino acid M at the nineth position is replaced with any other amino acid, particularly with G or removed, as set forth in SEQ ID NO: 148 (EIIQR(I,V)GCG) and SEQ ID NO: 149 (EIIQR(I,V)GC), respectively.

According to some embodiments, the HPPD protein may be a modified version of an endogenous HPPD protein of a dicot plant, wherein a motif of the endogenous HPPD protein has the consensus sequence set forth in SEQ ID NO: 81 (CMX(E,K,Q)(D,N)(E,A)EG(K,E)—wherein X may be any amino acid) and, wherein the modified version has HPPD enzymatic activity and comprises the amino acid sequence set forth in SEQ ID NO: 81, wherein the amino acid amino acid C at the first position is replaced with any other amino acid, particularly with F, as set forth in SEQ ID NO: 150 (FMX(E,K,Q)(D,N)(E,A)EG(K,E)); and/or all the amino acids but the amino acid C at the first position are replaced with any other amino acid, particularly with G or removed.

According to some embodiments, the HPPD protein may be a modified version of an endogenous HPPD protein of a dicot plant, wherein a motif of the endogenous HPPD protein has the consensus sequence set forth in SEQ ID NO: 82 (G(K,E)XYQ(K,S)G(G,A)—wherein X may be any amino acid) and, wherein the modified version has HPPD enzymatic activity and comprises the amino acid sequence set forth in SEQ ID NO: 82, all the amino acids are replaced with any other amino acid, particularly with G or removed.

According to some embodiments, the HPPD protein may be a modified version of an endogenous HPPD protein of a dicot plant, wherein a motif of the endogenous HPPD protein has the consensus sequence set forth in SEQ ID NO: 83 (YQ(K,S)G(G,A)CGGFG) and, wherein the modified version has HPPD enzymatic activity and comprises the amino acid sequence set forth in SEQ ID NO: 83, wherein the first six amino acids are replaced with any other amino acid, particularly with G or removed; and/or wherein the amino acid G at the seventh position is replaced with any other amino acid, particularly with E or S, as set forth in SEQ ID NO: 151 (YQ(K,S)G(G,A)C(E,S)GFG).

According to some embodiments, the HPPD protein may be a modified version of an endogenous HPPD protein of a dicot plant, wherein a motif of the endogenous HPPD protein has the consensus sequence set forth in SEQ ID NO: 84 ((A,S)EV(R,H,K)LYGDV) and, wherein the modified version has HPPD enzymatic activity and comprises the amino acid sequence set forth in SEQ ID NO: 84, wherein the amino acid E at the second position is replaced with any other amino acid, particularly with T or V, as set forth in SEQ ID NO: 152 ((A,S)(T,V)V(R,H,K)LYGDV).

According to some embodiments, the HPPD protein may be a modified version of an endogenous HPPD protein of a dicot plant, wherein a motif of the endogenous HPPD protein has the consensus sequence set forth in SEQ ID NO: 85 ((E,Q)L(A,G,S)P(A,V)(V,L,I)X—wherein X may be any amino acid) and, wherein the modified version has HPPD enzymatic activity and comprises the amino acid sequence set forth in SEQ ID NO: 85, wherein the amino acid P at the fourth position is replaced with any other amino acid, particularly with S or K, as set forth in SEQ ID NO: 153 ((E,Q)L(A,G,S)(S,K)(A,V)(V,L,I)X).

According to some embodiments, the HPPD protein may be a modified version of an endogenous HPPD protein of a dicot plant, wherein a motif of the endogenous HPPD protein has the consensus sequence set forth in SEQ ID NO: 86 ((V,L,I)XY(L,V,I)(K,A)XF—wherein X may be any amino acid) and, wherein the modified version has HPPD enzymatic activity and comprises the amino acid sequence set forth in SEQ ID NO: 86, wherein the amino acid Y at the third position is replaced with any other amino acid, particularly with F, as set forth in SEQ ID NO: 154 ((V,L,I)XF(L,V,I)(K,A)XF).

According to some embodiments, the HPPD protein may be a modified version of an endogenous HPPD protein of a dicot plant, wherein a motif of the endogenous HPPD protein has the consensus sequence set forth in SEQ ID NO: 87 (F(V,I)RXNP—wherein X may be any amino acid) and, wherein the modified version has HPPD enzymatic activity and comprises the amino acid sequence set forth in SEQ ID NO: 87, wherein the amino acid R at the third position is replaced with any other amino acid, particularly with A, D or Q, as set forth in SEQ ID NO: 155 (F(V,I)(A,D,Q)XNP).

According to some embodiments, the HPPD protein may be a modified version of an endogenous HPPD protein of a dicot plant, wherein a motif of the endogenous HPPD protein has the consensus sequence set forth in SEQ ID NO: 199 (EELGILVD), wherein the first G is replaced with any other amino acid, particularly with N or D, as set forth in SEQ ID NO: 156 (EEL(N, D)ILVD).

According to some embodiments, the HPPD protein may be a modified version of an endogenous HPPD protein of a dicot plant, wherein a motif of the endogenous HPPD protein has the consensus sequence set forth in SEQ ID NO: 200 (DVVLRYVS), wherein the first Y is replaced with any other amino acid, particularly with F, as set forth in SEQ ID NO: 157 (DVVLRFVS).

According to some embodiments, the HPPD protein may be a modified version of an endogenous HPPD protein of a dicot plant, wherein a motif of the endogenous HPPD protein has the consensus sequence set forth in SEQ ID NO: 201 (GFGKGNF), wherein the first K is replaced with any other amino acid, particularly with A, as set forth in SEQ ID NO: 158 (GFGAGNF).

According to some embodiments, the HPPD protein may be a modified version of an endogenous HPPD protein of a monocot plant, wherein a motif of the endogenous HPPD protein has the consensus sequence set forth in SEQ ID NO: 88 ((E,A)(D,E)AFR(A,V)SVA(A,G)GA) and, wherein the modified version has HPPD enzymatic activity and comprises the amino acid sequence set forth in SEQ ID NO: 88, wherein the amino acid F at the fourth position is replaced with any other amino acid, particularly with Y, as set forth in SEQ ID NO: 159 ((E,A)(D,E)AYR(A,V)SVA(A,G)GA); and/or wherein the amino acid R at the fifth position is replaced with any other amino acid, particularly with N, as set forth in SEQ ID NO: 160 ((E,A)(D,E)AFN(A,V)SVA(A,G)GA); and/or wherein the amino acid (A,V) at the sixth position is replaced with any other amino acid, particularly with K, as set forth in SEQ ID NO: 161 ((E,A)(D,E)AFRKSVA(A,G)GA); and/or wherein the amino acid S at the seventh position is replaced with any other amino acid, particularly with A, as set forth in SEQ ID NO: 162 ((E,A)(D,E)AFR(A,V)SVA(A,G)GA); and/or wherein the amino acid (A,G) at the tenth position is replaced with any other amino acid, particularly with E, as set forth in SEQ ID NO: 163 ((E,A)(D,E)AFR(A,V)SVAEGA).

According to some embodiments, the HPPD protein may be a modified version of an endogenous HPPD protein of a monocot plant, wherein a motif of the endogenous HPPD protein has the consensus sequence set forth in SEQ ID NO: 89 (VA(A,G)GARPAF(Q,A)P) and, wherein the modified version has HPPD enzymatic activity and comprises the amino acid sequence set forth in SEQ ID NO: 89, wherein the amino acid (A,G) at the third position is replaced with any other amino acid, particularly with E, as set forth in SEQ ID NO: 164 (VAEGARPAF(Q,A)P); and/or wherein the amino acid R at the sixth position is replaced with any other amino acid, particularly with I, as set forth in SEQ ID NO: 165 (VA(A,G)GAIPAF(Q,A)P); and/or wherein the amino acid P at the seventh position is replaced with any other amino acid, particularly with A, as set forth in SEQ ID NO: 166 (VA(A,G)GARAAF(Q,A)P); and/or wherein the amino acid F at the nineth position is replaced with any other amino acid, particularly with Q, as set forth in SEQ ID NO: 167 (VA(A,G)GARPAQ(Q,A)P); and/or wherein the amino acid (Q,A) at the tenth position is replaced with any other amino acid, particularly with G, as set forth in SEQ ID NO: 168 (VA(A,G)GARPAFGP).

According to some embodiments, the HPPD protein may be a modified version of an endogenous HPPD protein of a monocot plant, wherein a motif of the endogenous HPPD protein has the consensus sequence set forth in SEQ ID NO: 90 (FHEFAEFT(A,T)) and, wherein the modified version has HPPD enzymatic activity and comprises the amino acid sequence set forth in SEQ ID NO: 90, wherein the amino acid A at the fifth position is replaced with any other amino acid, particularly with W or R, as set forth in SEQ ID NO: 169 (FHEF(W,R)EFT(A,T)); and/or wherein the amino acid T at the eighth position is replaced with any other amino acid, particularly with D, as set forth in SEQ ID NO: 170 (FHEFAEFD(A,T)); and/or wherein the amino acid (A,T) at the tenth position is replaced with any other amino acid, particularly with D, as set forth in SEQ ID NO: 171 (FHEFAEFTD).

According to some embodiments, the HPPD protein may be a modified version of an endogenous HPPD protein of a monocot plant, wherein a motif of the endogenous HPPD protein has the consensus sequence set forth in SEQ ID NO: 91 (T(A,T)EDVGT(A,T)ES) and, wherein the modified version has HPPD enzymatic activity and comprises the amino acid sequence set forth in SEQ ID NO: 91, wherein the amino acid T at the first position is replaced with any other amino acid, particularly with D, as set forth in SEQ ID NO: 172 (D(A,T)EDVGT(A,T)ES); and/or wherein the amino acid (A,T) at the second position is replaced with any other amino acid, particularly with D, as set forth in SEQ ID NO: 173 (TDEDVGT(A,T)ES); and/or wherein the amino acid E at the ninth position is replaced with any other amino acid, particularly with F or Y, as set forth in SEQ ID NO: 174 (T(A,T)EDVGT(A,T)(F,Y)S).

According to some embodiments, the HPPD protein may be a modified version of an endogenous HPPD protein of a monocot plant, wherein a motif of the endogenous HPPD protein has the consensus sequence set forth in SEQ ID NO: 92 (FEF(L,M)APP(P,T,Q)(S,P,A)(D,N,K)YYW) and, wherein the modified version has HPPD enzymatic activity and comprises the amino acid sequence set forth in SEQ ID NO: 92, wherein the amino acid (L,M) at the fourth position is replaced with any other amino acid, particularly with I, as set forth in SEQ ID NO: 175 (FEFIAPP(P,T,Q)(S,P,A)(D,N,K)YYW); and/or wherein the amino acid A at the fifth position is replaced with any other amino acid, particularly with N, as set forth in SEQ ID NO: 176 (FEF(L,M)NPP(P,T,Q)(S,P,A)(D,N,K)YYW); and/or wherein the amino acid P at the sixth position is replaced with any other amino acid, particularly with V, as set forth in SEQ ID NO: 177 (FEF(L,M)AVP(P,T,Q)(S,P,A)(D,N,K)YYW); and/or wherein the amino acid (P,T,Q) at the eighth position is replaced with any other amino acid, particularly with G, as set forth in SEQ ID NO: 178 (FEF(L,M)APPG(S,P,A)(D,N,K)YYW); and/or wherein the amino acid (S,P,A) at the nineth position is replaced with any other amino acid, particularly with G or removed, as set forth in SEQ ID NO: 179 (FEF(L,M)APP(P,T,Q)G(D,N,K)YYW) and SEQ ID NO: 180 (FEF(L,M)APP(P,T,Q)(D,N,K)YW), respectively.

According to some embodiments, the HPPD protein may be a modified version of an endogenous HPPD protein of a monocot plant, wherein a motif of the endogenous HPPD protein has the consensus sequence set forth in SEQ ID NO: 93 ((D,N,K)YY(D,E)GVRRGV) and, wherein the modified version has HPPD enzymatic activity and comprises the amino acid sequence set forth in SEQ ID NO: 93, wherein the amino acid (D, E) at the fourth position is replaced with any other amino acid, particularly with D, as set forth in SEQ ID NO: 181 ((D,N,K)YYDGVRRGV); and/or wherein the amino acid R at the eighth position is replaced with any other amino acid, particularly with L, as set forth in SEQ ID NO: 182 ((D,N,K)YY(D,E)GVRLGV).

According to some embodiments, the HPPD protein may be a modified version of an endogenous HPPD protein of a monocot plant, wherein a motif of the endogenous HPPD protein has the consensus sequence set forth in SEQ ID NO: 94 (QELGVLVD) and, wherein the modified version has HPPD enzymatic activity and comprises the amino acid sequence set forth in SEQ ID NO: 94, wherein the first G is replaced with any other amino acid, particularly with N or D, as set forth in SEQ ID NO: 183 (QEL(N,D)VLVD).

According to some embodiments, the HPPD protein may be a modified version of an endogenous HPPD protein of a monocot plant, wherein a motif of the endogenous HPPD protein has the consensus sequence set forth in SEQ ID NO: 95 (VDRDDQGV) and wherein the modified version has HPPD enzymatic activity and comprises the amino acid sequence set forth in SEQ ID NO: 95, wherein the first R is replaced with any other amino acid, particularly with Y or F, as set forth in SEQ ID NO: 184 (VD(Y,F)DDQGV); and/or wherein the first Q is replaced with any other amino acid, particularly with A or G, as set forth in SEQ ID NO: 185 (VDRDD(A,G)GV).

According to some embodiments, the HPPD protein may be a modified version of an endogenous HPPD protein of a monocot plant, wherein a motif of the endogenous HPPD protein has the consensus sequence set forth in SEQ ID NO: 96 (EMIQRIGCM) and wherein the modified version has HPPD enzymatic activity and comprises the amino acid sequence set forth in SEQ ID NO: 96, wherein the amino acid I at the sixth position is replaced with any other amino acid, particularly with N, as set forth in SEQ ID NO: 186 (EMIQRNGCM); and/or wherein the amino acid G at the seventh position is replaced with any other amino acid, particularly with N, as set forth in SEQ ID NO: 187 (EMIQRINCM); and/or wherein the amino acid C at the eighth position is replaced with any other amino acid, particularly with F, as set forth in SEQ ID NO: 188 (EMIQRIGFM); and/or wherein the amino acid M at the nineth position is replaced with any other amino acid, particularly with G or removed, as set forth in SEQ ID NO: 189 (EMIQRIGCG) and SEQ ID NO: 190 (EMIQRIGC).

According to some embodiments, the HPPD protein may be a modified version of an endogenous HPPD protein of a monocot plant, wherein a motif of the endogenous HPPD protein has the consensus sequence set forth in SEQ ID NO: 97 (CMEKDE(K,S,V)GQ) and wherein the modified version has HPPD enzymatic activity and comprises the amino acid sequence set forth in SEQ ID NO: 97, wherein the amino acid C at the first position is replaced with any other amino acid, particularly with F, as set forth in SEQ ID NO: 191 (FMEKDE(K,S,V)GQ); and/or wherein all the amino acids but the amino acid C at the first position are replaced with any other amino acid, particularly with G or removed.

According to some embodiments, the HPPD protein may be a modified version of an endogenous HPPD protein of a monocot plant, wherein a motif of the endogenous HPPD protein has the consensus sequence set forth in SEQ ID NO: 98 (GQEYQKGA) and wherein the modified version has HPPD enzymatic activity and comprises the amino acid sequence set forth in SEQ ID NO: 98, wherein all the amino acids are replaced with any other amino acid, particularly with G or removed.

According to some embodiments, the HPPD protein may be a modified version of an endogenous HPPD protein of a monocot plant, wherein a motif of the endogenous HPPD protein has the consensus sequence set forth in SEQ ID NO: 99 (AEVELYGDV) and, wherein the modified version has HPPD enzymatic activity and comprises the amino acid sequence set forth in SEQ ID NO: 99, wherein the amino acid E at the second position is replaced with any other amino acid, particularly with T or V, as set forth in SEQ ID NO: 192 (A(T,V)VELYGDV).

According to some embodiments, the HPPD protein may be a modified version of an endogenous HPPD protein of a monocot plant, wherein a motif of the endogenous HPPD protein has the consensus sequence set forth in SEQ ID NO: 100 (E(L,M)AP(A,V)(A,I)(A,D)) and, wherein the modified version has HPPD enzymatic activity and comprises the amino acid sequence set forth in SEQ ID NO: 100, wherein the amino acid P at the fourth position is replaced with any other amino acid, particularly with S or K, as set forth in SEQ ID NO: 193 (E(L,M)A(S,K)(A,V)(A,I)(A,D)).

According to some embodiments, the HPPD protein may be a modified version of an endogenous HPPD protein of a monocot plant, wherein a motif of the endogenous HPPD protein has the consensus sequence set forth in SEQ ID NO: 101 ((A,I)(A,D)Y(F,I,M)(A,S,K)GF) and wherein the modified version has HPPD enzymatic activity and comprises the amino acid sequence set forth in SEQ ID NO: 101, wherein the amino acid Y at the third position is replaced with any other amino acid, particularly with F, as set forth in SEQ ID NO: 194 ((A,I)(A,D)F(F,I,M)(A,S,K)GF).

According to some embodiments, the HPPD protein may be a modified version of an endogenous HPPD protein of a monocot plant, wherein a motif of the endogenous HPPD protein has the consensus sequence set forth in SEQ ID NO: 102 ((F,V)VR(F,A,V)NP) and wherein the modified version has HPPD enzymatic activity and comprises the amino acid sequence set forth in SEQ ID NO: 102, wherein the amino acid R at the third position is replaced with any other amino acid, particularly with A, D or Q, as set forth in SEQ ID NO: 195 ((F,V)V(A,D,Q)(F,A,V)NP).

According to some embodiments, the HPPD protein may be a modified version of an endogenous HPPD protein of a monocot plant, wherein a motif of the endogenous HPPD protein has the consensus sequence set forth in SEQ ID NO: 202 (YQKGACGGFG), wherein the first six amino acids are replaced with any other amino acid in particular with G or removed; and/or wherein the second G is replaced with any other amino acid, particularly with E or S, as set forth in SEQ ID NO: 196 (YQKGAC(E,S)GFG).

According to some embodiments, the HPPD protein may be a modified version of an endogenous HPPD protein of a monocot plant, wherein a motif of the endogenous HPPD protein has the consensus sequence set forth in SEQ ID NO: 203 (DVVLRYVSY), wherein the first Y is replaced with any other amino acid, particularly with F, as set forth in SEQ ID NO: 197 (DVVLRFVSY).

According to some embodiments, the HPPD protein may be a modified version of an endogenous HPPD protein of a monocot plant, wherein a motif of the endogenous HPPD protein has the consensus sequence set forth in SEQ ID NO: 204 (GFGKGNF), wherein the first K is replaced with any other amino acid, particularly with A, as set forth in SEQ ID NO: 198 (GFGAGNF).

According to some embodiments, the polypeptides of the invention are catalytically active HPPDs derived from a fungus that confer efficient levels of resistance and/or tolerance to certain classes of herbicides that inhibit HPPD. According to some embodiments, the HPPD, and sequence encoding same, is derived from a fungus of the species *Trichoderma*. According to some embodiments, the HPPD, and sequence encoding same, is derived from a fungus of the species *Trichoderma*. According to some embodiments, the HPPD, and sequence encoding same, is derived from a fungus of the species T asperellum, *T. harzianum, T. viride, T. hamatum* or any combination thereof. According to some embodiments, the HPPD, and sequence encoding same, is derived from a fungus of the species *T. harzianum*. According to some embodiments, the HPPD, is derived from the *Trichoderma* Ti-123 disclosed in U.S. 63/018,027. According to some embodiments, the HPPD, and sequence encoding same, is derived from a fungus of the species *Talaromyces* spp.

Exemplary HPPD polypeptides according to the invention correspond to the amino acid sequences set forth in SEQ ID NO: 1, 3, 5-8 and variants and fragments thereof. Nucleic acid molecules comprising polynucleotide sequences that encode these particular HPPD polypeptides are set forth in SEQ ID NO: 2, 4 although other nucleic acid sequences may also be envisaged. Compositions also include expression cassettes comprising a promoter operably linked to a nucleotide sequence that encodes an HPPD polypeptide of the invention, alone or in combination with one or more additional nucleic acid molecules encoding polypeptides that confer desirable traits. Transformed plants, plant cells, and seeds comprising an expression cassette of the invention are further provided.

The compositions of the invention are useful in methods directed to conferring herbicide resistance or tolerance to plants, particularly resistance or tolerance to certain classes of herbicides that inhibit HPPD. In particular embodiments, the methods comprise introducing into a plant at least one expression cassette comprising a promoter operably linked to a nucleotide sequence that encodes an HPPD polypeptide of the invention. As a result, the HPPD polypeptide is expressed in the plant, and since the HPPD is selected on the basis that it is less sensitive to HPPD-inhibiting herbicides, this leads to the plant exhibiting substantially improved resistance or tolerance to HPPD-inhibiting herbicides.

Methods of the present invention also comprise selectively controlling weeds in a crop field. In one embodiment, such methods involve over-the-top pre- or postemergence application of weed-controlling amounts of HPPD herbicides in a field that contains plants expressing the HPPD polypeptides of the invention. In other embodiments, methods are also provided for the assay, characterization, identification, and selection of the HPPDs of the current invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

The invention will now be described in relation to certain examples and embodiments with reference to the following illustrative figures so that it may be more fully understood.

FIG. 7A shows the influence of motif 5 on the loop and helix 9 (H9) of the HPPD of *A. thaliana.*

FIG. 7B shows the influence of motif 5 on the loop and helix 9 (H9) of HPPD built based on SEQ ID NO: 1.

FIG. 7C, shows the superimposition of FIG. 7A and FIG. 7B.

DETAILED DESCRIPTION

Figure 1:
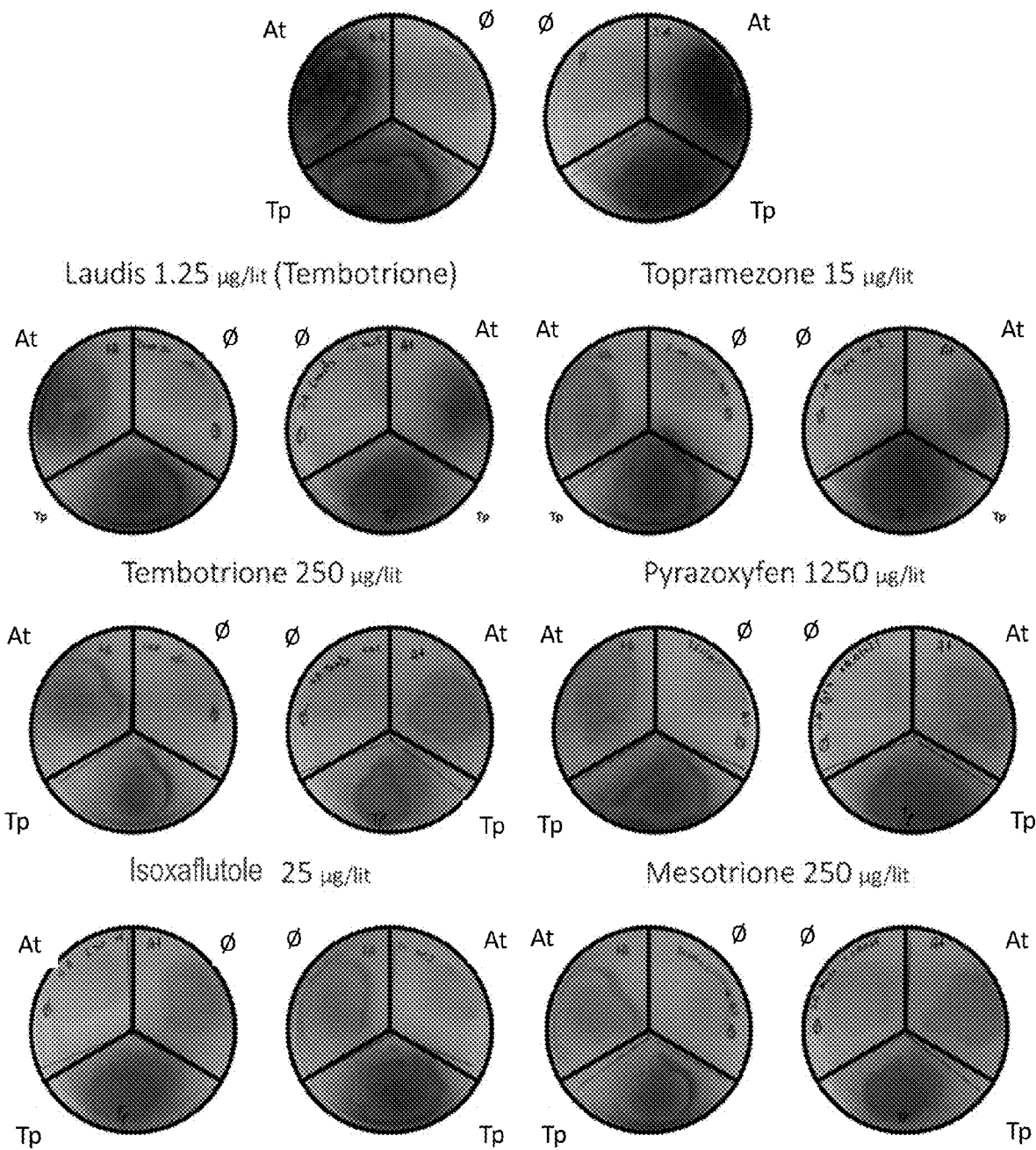
FIG. 1 shows illustrative images obtained from a HPPD-activity screen of *E. coli* BL21 (DE3) transformed with a) a HPPD cDNA derived from a *Trichoderma* spp. (as disclosed herein), b) a HPPD cDNA derived from *Arabidopsis thaliana*, and c) empty vector when grown in increasing concentrations HPPD inhibitors.

The present invention provides compositions and methods directed to conferring hydroxyphenyl pyruvate di oxygenase (HPPD) herbicide resistant and/or tolerant plants.

Compositions include amino acid sequences for HPPD polypeptides having fungus derived HPPD enzymatic activity, and variants and fragments thereof. Nucleic acids that encode the fungus derived HPPD polypeptides of the invention are also provided. Methods for conferring herbicide resistance and/or tolerance to plants, particularly resistance and/or tolerance to certain classes of herbicides that inhibit HPPD, are further provided. Methods are also provided for selectively controlling weeds in a crop field and for the assay, characterization, identification and selection of the mutant HPPDs of the current invention that provide herbicide tolerance.

Within the context of the present invention, the terms "hydroxy phenyl pyruvate dioxygenase (HPPD)", "4-hydroxy phenyl pyruvate dioxygenase (4-HPPD)" and "p-hydroxy phenyl pyruvate dioxygenase (p-HPPD)" are synonymous.

"HPPD herbicides" are herbicides that are bleachers and whose primary site of action is HPPD. Many are well known and described elsewhere e.g. (Hawkes "Hydroxyphenylpyruvate Dioxygenase (HPPD)—The Herbicide Target." In Modern Crop Protection Compounds. Eds. Kramer and Schirmer). As used herein, the term "HPPD herbicides" refers to herbicides that act either directly or indirectly to inhibit HPPD, where the herbicides are bleachers and where inhibition of HPPD is at least part of the herbicide's mode of action on plants.

As used herein, plants which are substantially "tolerant" to a herbicide exhibit, when treated with said herbicide, a dose/response curve which is shifted to the right when compared with that exhibited by similarly subjected non-tolerant plants. Tolerant plants will typically require at least twice as much herbicide as non-tolerant plants in order to produce a given herbicidal effect. Plants which are substantially "resistant" to the herbicide exhibit few, if any, necrotic, lytic, chlorotic or other lesions or, at least, none that impact significantly on yield, when subjected to the herbicide at concentrations and rates which are typically employed by the agricultural community to kill weeds in the field.

As used herein, the term "confer" refers to providing a characteristic or trait, such as herbicide tolerance or resistance, to a plant.

The terms "polypeptide", "peptide", and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Polypeptides of the invention can be produced either from a nucleic acid disclosed herein, or by the use of standard molecular biology techniques. For example, a truncated protein of the invention can be produced by expression of a recombinant nucleic acid of the invention in an appropriate host cell, or alternatively by a combination of ex-vivo procedures, such as protease digestion and purification.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

Fragments and variants of the disclosed nucleotide sequences and proteins encoded thereby are also encompassed by the present invention. As used herein, "fragment" is intended to mean a portion of the nucleotide sequence or a portion of the amino acid sequence and hence protein encoded thereby. Fragments of a nucleotide sequence may encode protein fragments that retain the biological activity of the fungus-derived HPPD protein and hence have HPPD enzymatic activity. A fragment of a nucleotide sequence that encodes a biologically active portion of the fungus-derived HPPD protein of the invention will encode at least 15, 25, 30, 40, 50, 60, 70, 80, 90, 100, 110, 120, 150, 180, 200, 250, 300, 350 contiguous amino acids, or up to the total number of amino acids present in a full-length fungus-derived HPPD polypeptide of the invention. As used herein, "full-length sequence" in reference to a specified polynucleotide means having the entire nucleic acid sequence of the fungus-derived HPPD sequence. As used herein, the term "native sequence" refers to the endogenous sequence, i.e., a non-engineered sequence found in the non-engineered plant.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

"Variants" is intended to mean substantially similar sequences. For polynucleotides, a variant comprises a deletion and/or addition of one or more nucleotides at one or more internal sites within the reference polynucleotide and/or a substitution of one or more nucleotides at one or more sites in the fungus-derived HPPD polynucleotide. One of skill in the art will recognize that variants of the nucleic acids of the invention will be constructed such that the open reading frame is maintained. For polynucleotides, conservative variants include those sequences that, because of the degeneracy of the genetic code, encode the amino acid sequence of the fungus-derived HPPD polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode the fungus derived HPPD protein of the invention. Generally, variants of a particular polynucleotide of the invention will have at least about 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, a polynucleotide that encodes a polypeptide with a given percent sequence identity to the polypeptides of SEQ ID NO: 1, 3, 5-8 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 70%, 75%, 80%, 85%, 90%, 91%, 92%, 93%, 94%, 95%, 96%, 97%, 98%, 99% or more sequence identity across the entirety of the HPPD sequences described herein. According to some embodiments, the polypeptide may have exactly the sequence set forth in any of SEQ ID NOs: 1, 3 and 5-8.

As used herein a "variant" protein refers to a protein derived from the reference protein by deletion or addition of one or more amino acids at one or more internal sites in the fungus-derived HPPD protein and/or substitution of one or more amino acids at one or more sites in the fungus-derived HPPD protein. Variant proteins encompassed by the present invention are biologically active, that is, they continue to possess the desired biological activity of the fungus-derived HPPD protein, that is, HPPD enzymatic activity and/or herbicide tolerance as described herein. Such variants may result from, for example, genetic polymorphism or from human manipulation. Biologically active variants will have at least about 70%, 75%, 80%, 85%, 90%, 91%, 92%, 93%, 94%, 95%, 96%, 97%, 98%, 99% or more sequence identity to the fungus-derived HPPD protein of the invention, as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The article "a" and "an" are used herein to refer to one or more than one (i.e., to at least one) of the grammatical object of the article. By way of example, "a nucleic acid" means one or more nucleic acids. Throughout the specification the word "comprising," or variations such as "comprises" will be understood to imply the inclusion of a stated element.

A variety of additional terms are defined or otherwise characterized herein.

HPPD Sequences

Specifically, the present invention provides HPPD polypeptides that have HPPD enzymatic activity and that confer resistance and/or tolerance in plants to certain classes of herbicides that inhibit HPPD, and variants and fragments thereof. Nucleic acids that encode the native and mutant HPPD polypeptides of the invention are also provided.

The HPPD polypeptides and nucleic acid sequences encoding same are derived from a fungus and may include nucleic acid and optionally amino acid changes at one or more positions relative to the sequence from which they are derived and exhibit enhanced tolerance to one or more HPPD inhibitor herbicides. HPPD enzymes that exhibit enhanced tolerance to an HPPD herbicide may do so by virtue of exhibiting, relative to the native enzyme of the plant.

DNA sequences encoding the fungus derived HPPDs are used in the provision of HPPD plants, crops, plant cells and seeds of the current invention that offer enhanced tolerance or resistance to one or more HPPD herbicides as compared to like plants likewise expressing the unmutated starting enzyme. According to some embodiments, the nucleic acid encoding the fungus derived HPPD may be extracted and isolated from the fungus. According to some embodiments, the nucleic acid encoding the fungus derived HPPD may be synthetically generated.

According to some embodiments, the HPPD, and sequence encoding same, is derived from a fungus of the species *Trichoderma*. According to some embodiments, the HPPD, and sequence encoding same, is derived from a fungus of the species *Trichoderma*. According to some embodiments, the HPPD, and sequence encoding same, is derived from a fungus of the species T asperellum, *T. harzianum, T. viride, T. hamatum* or any combination thereof. According to some embodiments, the HPPD, and sequence encoding same, is derived from a fungus of the species *T. harzianum*. According to some embodiments, the HPPD, is derived from the *Trichoderma* Ti-123 disclosed in U.S. 63/018,027.

According to some embodiments, the HPPD protein has the amino acid sequence set forth in SEQ ID NO: 1, namely:

MSPSAISNSPEQRPANNNGTTPDNFAIQPPADFTGYDHVTWWVGNAKQAA

AYYTTLFGFETTAYRGLETGSRYFASYVVCNNGVRFVFTSPLRSEAHLPE

DETISDSERKLLKEIHAHLERHGDAVKDVAFEVDNVEAVYNKAVAEGAIA

VQGPTATKDDHGSVTTAVICTYGDTTHTLINRRGYTGPFLPGFRAGKERT

SSVEMPNVPLARIDHCVGNQSWNEMVSACAFYEQCLSFHRFWSVDDSQIC

TEFSALNSIVMASPNNLVKMPINEPAPGKKKSQIEEYVIFNSGPGVQHIA

LLTPDIITSVSALRARGVEFINVPTTYYDTMRQRLKTEKRNWQLKEDLDT

IQRLNILIDYDEAGYLLQLFTKPLMDRPTVFIEIIQRNNFEGFGAGNFKS

LFEAIEREQAERGNL

According to some embodiments, the HPPD protein is encoded by the nucleic acid sequence set forth in SEQ ID NO: 2, namely:

ATGTCCCCGTCTGCTATCAGCAACTCCCCAGAGCAGCGACCTGCAAACAA

CAACGGCACCACCCCCGACAACTTCGCTATCCAGCCTCCCGCCGACTTCA

CCGGCTATGACCACGTAACGTGGTGGGTTGGCAACGCCAAGCAGGCGGCC

GCTTATTACACCACCCTCTTTGGGTTCGAGACTACGGCCTATCGTGGACT

CGAGACTGGAAGCCGATACTTCGCTTCCTATGTCGTCTGCAACAATGGCG

TCCGCTTCGTCTTCACGTCGCCTCTGCGATCGGAGGCTCACCTCCCTGAA

GATGAGACCATCTCTGATTCTGAGCGGAAGCTCCTGAAGGAGATTCACGC

TCACCTCGAGAGACACGGCGATGCCGTCAAGGACGTTGCCTTTGAAGTTG

ACAACGTCGAGGCCGTATACAACAAGGCCGTGGCTGAGGGCGCCATCGCC

GTCCAAGGCCCAACCGCCACCAAGGATGATCACGGCTCCGTCACCACGGC

CGTCATCTGCACCTATGGCGATACCACCCACACTCTCATCAACCGCCGGG

GCTACACGGGACCTTTCCTGCCCGGCTTCCGCGCCGGCAAGGAGCGCACC

TCGTCCGTGGAGATGCCCAACGTGCCCCTTGCCCGCATCGACCACTGCGT

CGGCAACCAGTCGTGGAACGAAATGGTCTCGGCCTGCGCCTTTTACGAGC

AGTGCCTGTCCTTCCACCGTTTCTGGTCCGTCGACGACTCCCAGATCTGC

ACCGAGTTCTCGGCCCTCAACTCCATCGTCATGGCCTCGCCCAACAACCT

CGTCAAGATGCCCATCAACGAGCCCGCCCCGGGCAAGAAGAAGTCCCAGA

TCGAGGAGTACGTCATCTTCAACTCCGGCCCGGGCGTCCAGCACATCGCC

CTCCTCACCCCGGACATCATCACCTCCGTCTCGGCCCTCCGCGCCCGCGG

CGTCGAGTTCATCAACGTGCCCACCACTTACTACGACACCATGCGCCAGC

GCCTCAAGACGGAGAAGCGCAACTGGCAGCTCAAGGAGGACCTGGACACC

ATCCAGCGCCTCAACATCCTCATCGACTACGACGAGGCCGGCTACCTCCT

GCAGCTCTTCACCAAGCCGCTCATGGACCGCCCTACCGTCTTCATTGAGA

TTATCCAGAGAAACAACTTTGAGGGCTTCGGCGCCGGCAACTTCAAGAGC

TTGTTCGAGGCCATTGAGCGCGAGCAGGCCGAGCGAGGAAACCTGTAA

According to some embodiments, the HPPD, and sequence encoding same, is derived from a fungus of the species *Talaromyces*.

According to some embodiments, the HPPD protein has the amino acid sequence set forth in SEQ ID NO: 3, namely:

MAPSAISDLQSDNLPTTQSALSSYRGYDHVHWYVGNAKQAATFYITRMGF

SRVAYRGLETGSRSVCSHVVRNGGITFVLTSPLRSPYNTEKLERLLPSAE

EREYLKEIHEHLARHGDAVKDVAFEVDSVDDVFAAAVQNGAVAVSQPKTV

EDENGQVRVATIRTYGDTTHTLIQRRGVEKPYSGVFLPGYRDETTSGSSD

PITAFLPKVDLRRIDHCVGNQDWDEMEKVCAYYEKVLGFHRFRSVDDKDI

CTDYSALKSIVMSSPNDIVKMPINEPAHGKKQSQIEEYVDFYDGAGVQHI

ALLTDDIISAITNLKARGVEFIKVPPTYYDNMWMRLKKAGMMPKEAWEDI

KKLDILIDFDEGGYLLQLFTKHLMDRPTVFIEIIQRNNFSGFGAGNFKSL

FEAIEREQALRGNLI

According to some embodiments, the HPPD protein is encoded by the nucleic acid sequence set forth in SEQ ID NO: 4, namely:

ATGGCACCATCAGCCATCTCAGACCTCCAATCCGACAACCTACCCACAAC

CCAATCCGCCCTCTCCTCCTACCGCGGCTACGACCATGTACACTGGTACG

TCGGCAACGCCAAACAGGCCGCAACCTTCTACATAACGCGCATGGGATTT

TCTCGTGTCGCCTACCGCGGTCTCGAAACCGGCTCTCGCAGCGTCTGCTC

ACACGTCGTGCGCAACGGCGGTATAACTTTTGTCCTGACCTCGCCGCTTC

GATCACCCTACAACACTGAGAAACTCGAGCGCCTACTTCCCAGTGCTGAA

GAGCGGGAGTATTTGAAAGAGATTCATGAGCATTTGGCACGACATGGTGA

TGCAGTCAAAGACGTCGCGTTTGAGGTCGATTCCGTCGATGATGTTCG

CTGCTGCGGTGCAGAATGGCGCCGTTGCGGTCTCGCAACCCAAGACCGTG

GAGGATGAGAATGGTCAAGTGAGGGTTGCCACGATTCGGACGTATGGGA

-continued
```
TACGACGCATACTTTGATTCAGCGACGGGGGGTCGAAAAGCCGTATTCGG

GCGTTTTCTTGCCAGGGTACAGGGATGAGACGACTTCTGGTAGCAGTGAT

CCTATCACGGCGTTCCTGCCCAAGGTTGATTTGAGGAGGATTGATCATTG

TGTGGGGAATCAGGATTGGGATGAAATGGAGAAGGTCTGCGCGTACTACG

AAAAAGTCCTCGGATTCCACCGTTTCCGGTCCGTAGACGACAAAGACATC

TGCACAGACTACTCCGCCCTGAAATCAATCGTCATGTCCTCGCCCAACGA

CATTGTCAAAATGCCCATCAACGAACCCGCCCACGGCAAAAAACAATCCC

AAATCGAAGAATACGTCGACTTTTACGACGGCGCCGGCGTCCAACACATT

GCCCTGCTGACAGACGACATAATCAGCGCGATCACGAATCTCAAAGCGCG

CGGGGTGGAGTTTATCAAAGTGCCGCCTACGTATTACGATAACATGTGGA

TGCGGCTGAAGAAAGCGGGCATGATGCCCAAGGAGGCGTGGGAGGATATT

AAGAAGTTGGATATTCTGATCGATTTTGATGAGGGAGGGTATTTGTTGCA

GCTCTTCACAAAGCATCTCATGGATCGGCCGACTGTTTTCATTGAGATTA

TTCAGCGCAATAACTTCTCAGGCTTTGGTGCTGGTAATTTCAAGTCGCTG

TTCGAAGCTATTGAACGTGAGCAGGCTCTTAGAGGAAACCTGATCTGA
```

According to some embodiments, the HPPD, expressed in the plant, is a partial HPPD devoid of 10-50 amino acids at N' terminus (e.g. devoid of the first 22 or first 38 amino acids).

According to some embodiments, the HPPD, expressed in the plant, is a partial HPPD e.g. SEQ ID NO: 1 devoid of amino acids 1-22 (Δ22). According to some embodiments, the partial 422-HPPD comprises the amino acid sequence set forth in SEQ ID NO: 5

```
(DNFAIQPPADFTGYDHVTWWVGNAKQAAAYYTTLFGFETTAYRGLET

GSRYFASYVVCNNGVRFVFTSPLRSEAHLPEDETISDSERKLLKEIHA

HLERHGDAVKDVAFEVDNVEAVYNKAVAEGAIAVQGPTATKDDHGSVT

TAVICTYGDTTHTLINRRGYTGPFLPGFRAGKERTSSVEMPNVPLARI

DHCVGNQSWNEMVSACAFYEQCLSFHRFWSVDDSQICTEFSALNSIVM

ASPNNLVKMPINEPAPGKKKSQIEEYVIFNSGPGVQHIALLTPDIITS

VSALRARGVEFINVPTTYYDTMRQRLKTEKRNWQLKEDLDTIQRLNIL

IDYDEAGYLLQLFTKPLMDRPTVFIEIIQRNNFEGFGAGNFKSLFEAI

EREQAERGNL)
```

According to some embodiments, the HPPD, expressed in the plant, is a partial HPPD e.g. SEQ ID NO: 1 devoid of amino acids 1-38 (Δ38). According to some embodiments, the partial 438-HPPD comprises the amino acid sequence set forth in SEQ ID NO: 6

```
(VTWWVGNAKQAAAYYTTLFGFETTAYRGLETGSRYFASYVVCNNGVR

FVFTSPLRSEAHLPEDETISDSERKLLKEIHAHLERHGDAVKDVAFEV

DNVEAVYNKAVAEGAIAVQGPTATKDDHGSVTTAVICTYGDTTHTLIN

RRGYTGPFLPGFRAGKERTSSVEMPNVPLARIDHCVGNQSWNEMVSAC

AFYEQCLSFHRFWSVDDSQICTEFSALNSIVMASPNNLVKMPINEPAP

GKKKSQIEEYVIFNSGPGVQHIALLTPDIITSVSALRARGVEFINVPT

TYYDTMRQRLKTEKRNWQLKEDLDTIQRLNILIDYDEAGYLLQLFTKP

LMDRPTVFIEIIQRNNFEGFGAGNFKSLFEAIEREQAERGNL).
```

According to some embodiments, the HPPD, expressed in the plant, is a partial HPPD e.g. SEQ ID NO: 3 devoid of amino acids 1-22 (Δ22). According to some embodiments, the partial 422-HPPD comprises the amino acid sequence set forth in SEQ ID NO: 7

```
(PTTQSALSSYRGYDHVHWYVGNAKQAATFYITRMGFSRVAYRGLETG

SRSVCSHVVRNGGITFVLTSPLRSPYNTEKLERLLPSAEEREYLKEIH

EHLARHGDAVKDVAFEVDSVDDVFAAAVQNGAVAVSQPKTVEDENGQV

RVATIRTYGDTTHTLIQRRGVEKPYSGVFLPGYRDETTSGSSDPITAF

LPKVDLRRIDHCVGNQDWDEMEKVCAYYEKVLGFHRERSVDDKDICTD

YSALKSIVMSSPNDIVKMPINEPAHGKKQSQIEEYVDFYDGAGVQHIA

LLTDDIISAITNLKARGVEFIKVPPTYYDNMWMRLKKAGMMPKEAWED

IKKLDILIDFDEGGYLLQLFTKHLMDRPTVFIEIIQRNNFSGFGAGNF

KSLFEAIEREQALRGNLI).
```

According to some embodiments, the HPPD, expressed in the plant, is a partial HPPD e.g. SEQ ID NO: 3 devoid of amino acids 1-30 (Δ30). According to some embodiments, the partial 430-HPPD comprises the amino acid sequence set forth in SEQ ID NO: 8

```
(VHWYVGNAKQAATFYITRMGFSRVAYRGLETGSRSVCSHVVRNGGIT

FVLTSPLRSPYNTEKLERLLPSAEEREYLKEIHEHLARHGDAVKDVAF

EVDSVDDVFAAAVQNGAVAVSQPKTVEDENGQVRVATIRTYGDTTHTL

IQRRGVEKPYSGVFLPGYRDETTSGSSDPITAFLPKVDLRRIDHCVGN

QDWDEMEKVCAYYEKVLGFHRFRSVDDKDICTDYSALKSIVMSSPNDI

VKMPINEPAHGKKQSQIEEYVDFYDGAGVQHIALLTDDIISAITNLKA

RGVEFIKVPPTYYDNMWMRLKKAGMMPKEAWEDIKKLDILIDFDEGGY

LLQLFTKHLMDRPTVFIEIIQRNNFSGFGAGNFKSLFEAIEREQALRG

NLI).
```

According to some embodiments, the nucleic acid sequence encoding the *Trichoderma* derived HPPD may have less than 80%, less than 70%, less than 60% or less than 50% similarity to that of the nucleic acid sequences encoding the HPPD enzyme endogenous to the plant in which it is expressed.

According to some embodiments, the nucleic acid sequence and amino acid sequence of the fungus-derived HPPD has less than 50%, less than 40% or less than 30% sequence identity to the HPPD nucleic acid and amino acid sequences of the native plants in which it is expressed. According to some embodiments, the HPPD enzyme encoded by the fungus-derived HPPD gene exhibits enzymatic activity in plants.

In some embodiment, the polypeptide comprises one or more amino acid substitutions, additions, or deletions. In some embodiment, the polypeptide comprises one or more substitutions corresponding to a conservative variant of the amino acid.

Accordingly, the present invention provides nucleic acid molecules comprising polynucleotide sequences that encode fungus-derived HPPD polypeptides that have HPPD enzymatic activity and that confer resistance or tolerance in plants to certain classes of herbicides that inhibit HPPD, and variants and fragments thereof. In general, the invention includes any polynucleotide sequence that encodes the HPPD polypeptides described herein, as well as any polynucleotide sequence that encodes HPPD polypeptides having one or more conservative amino acid substitutions relative to the HPPD polypeptides described herein. Conservative substitution tables providing functionally similar amino acids are well known in the art. The following five groups each contain amino acids that are conservative substitutions for one another: Nonpolar, aliphatic: Glycine (G), Alanine (A), Valine (V), Leucine (L), Isoleucine (I), Methionine (M); Nonpolar, aromatic: Phenylalanine (F), Tyrosine (Y), Tryptophan (W); Polar, uncharged: Cysteine (C), Serine (S), Threonine (T), Proline (P), Asparagine (N), Glutamine (Q); Basic: Arginine (R), Lysine (K), Histidine (H); Acidic: Aspartic acid (D), Glutamic acid (E).

In one embodiment, the present invention provides a polynucleotide sequence encoding an amino acid sequence having at least about 70%, 75%, 80%, 85%, 90%, 91%, 92%, 93%, 94%, 95%, 96%, 97%, 98%, 99% or more sequence identity to SEQ ID NO: 1, SEQ ID NO: 3, SEQ ID NO: 5, SEQ ID NO: 6, SEQ ID NO: 7 or SEQ ID NO: 8, where the HPPD amino acid sequence is derived from a fungus, where the polypeptide has HPPD enzymatic activity, and where the polypeptide contains one or more substitutions, additions or deletions as discussed. According to some embodiments, the HPPD, and sequence encoding same, is derived from a fungus of the species *Trichoderma*. According to some embodiments, the HPPD, and sequence encoding same, is derived from a fungus of the species *Trichoderma*. According to some embodiments, the HPPD, and sequence encoding same, is derived from a fungus of the species T asperellum, *T. harzianum, T. viride, T. hamatum, Trichoderma* Ti-123 disclosed in U.S. 63/018,027, or any combination thereof. According to some embodiments, the HPPD, and sequence encoding same, is derived from a fungus of the species *Talaromyces*. According to some embodiments, the HPPD, and sequence encoding same, is derived from a fungus of the species *T. hamatum*.

Gene Stacking

In certain embodiments the polynucleotides of the invention encoding the fungus-derived HPPD polypeptides or variants thereof that retain HPPD enzymatic activity (e.g., a polynucleotide sequence encoding an amino acid sequence selected from the group consisting of SEQ ID NO: 1, 3, 5-8) can be stacked with any combination of polynucleotide sequences of interest in order to create plants with a desired trait. A trait, as used herein, refers to the phenotype derived from a particular sequence or groups of sequences. For example, the polynucleotides encoding the fungus derived HPPD polypeptide or variant thereof that retains HPPD enzymatic activity may be stacked with any other polynucleotides encoding polypeptides that confer a desirable trait, including, but not limited to, resistance to diseases, insects, and herbicides, tolerance to heat and drought, reduced time to crop maturity, improved industrial processing, such as for the conversion of starch or biomass to fermentable sugars, and improved agronomic quality, such as high oil content and high protein content.

In a particular embodiment of the invention, polynucleotides may be stacked (or, alternatively, expression cassettes may be stacked on a single polynucleotide) so as to express more than one type of HPPD polypeptide within a plant. This is a particular advantage where, for example, one HPPD is particularly suitable for providing resistance to one class of HPPD herbicide while the other provides better tolerance to a different class of HPPD herbicide. Stacking HPPD polypeptides is also an advantage where one polypeptide expresses inherent herbicide-resistance but is somewhat labile. This herbicide-resistant HPPD can then be stabilized in mixed expression with, for example, similar but less temperature-labile HPPDs through the formation of mixed enzyme dimers.

Exemplary polynucleotides that may be stacked with polynucleotides of the invention encoding the fungus-derived HPPD polypeptide or variant thereof that retains HPPD enzymatic activity include polynucleotides encoding polypeptides conferring resistance to pests/pathogens such as viruses, nematodes, insects or fungi, and the like. Exemplary polynucleotides that may be stacked with polynucleotides of the invention include polynucleotides encoding: polypeptides having pesticidal and/or insecticidal activity, such as other *Bacillus thuringiensis* toxic proteins, lectins, pentin, and the like; traits desirable for disease or herbicide resistance (e.g., fumonisin detoxification genes; avirulence and disease resistance genes); a gene encoding an aryloxyalkanoate dioxygenase conferring resistance to certain classes of auxin and acetylCoA carboxylase herbicides or a tfdA gene giving resistance to 2,4 D; a gene encoding a dicamba monoxygenase conferring resistance to dicamba; a gene encoding a homogentisate solanesyltransferase (HST) conferring resistance to HST-inhibiting herbicides; a gene encoding a nitrilase conferring resistance to a nitrile-containing herbicide (e.g. the bxnA bromoxynil nitrilase); acetolactate synthase (ALS) mutants that lead to herbicide resistance such as the S4 and/or Hra mutations; glyphosate resistance (e.g., 5-enol-pyrovyl-shikimate-3-phosphate-synthase (EPSPS) gene, or the glyphosate N-acetyltransferase (GAT) gene); glufosinate resistance (e.g., phosphinothricin acetyl transferase genes PAT and BAR); a cytochrome P450 or variant thereof that confers herbicide resistance or tolerance to, inter alia, HPPD herbicides; and traits desirable for processing or process products such as high oil; modified oils (e.g., fatty acid desaturase genes); modified starches (e.g., ADPG pyrophosphorylases (AGPase), starch synthases (SS), starch branching enzymes (SBE), and starch debranching enzymes (SDBE)); and polymers or bioplastics; beta-ketothiolase, polyhydroxybutyrate synthase, and acetoacetyl-CoA reductase.

According to some embodiments, the desirable trait is resistance or tolerance to glyphosate. In another embodiment, the desirable trait is resistance or tolerance to glufosinate, an HST inhibitor herbicide, an auxin herbicide or a PRI herbicide or any combination thereof.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation/gene editing. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system.

According to some embodiments, the herein disclosed modified HPPD protein may be translationally fused to a signal peptide. According to some embodiments, the herein disclosed modified HPPD protein may be translationally fused to a chloroplast-targeting peptide (CTP). According to some embodiments, the signal peptide (CTP) may be fused to the N-terminus of the herein disclosed modified HPPD protein or replace the N-terminus of the herein disclosed modified HPPD protein (i.e. be fused to any one of the amino acid sequences set forth in SEQ ID NO: 1, 3 or 5-8). According to some embodiments, the signal peptide may have at least 85%, at least 90% or at least 95% sequence similarity to the CTP consensus sequence set forth in SEQ ID NO: 103, namely: MPPTPTTAAATGAGAAAVTPE-HAAFRLV. According to some embodiments, the CTP comprises SEQ ID NO: 103. According to some embodiments, the CTP consists of SEQ ID NO: 103. According to some embodiments, the signal peptide may have at least 85%, at least 90% or at least 95% sequence similarity to the CTP consensus sequence set forth in SEQ ID NO: 104, namely: MGHQNAAVSENQNHDDGAASSP. According to some embodiments, the CTP comprises SEQ ID NO: 104. According to some embodiments, the CTP consists of SEQ ID NO: 104. According to some embodiments, the signal peptide may have at least 85%, at least 90% or at least 95% sequence similarity to the CTP consensus sequence of *Arabidopsis thaliana* (amino acids 1-38), as set forth in SEQ ID NO: 105, namely: MGHQNAAVSENQNHDD-GAASSPGFKLVGFSKFVRKNPKSDKFKVKRFHH. According to some embodiments, the CTP comprises SEQ ID NO: 105. According to some embodiments, the CTP consists of SEQ ID NO: 105.

According to some embodiments, the HPPD, expressed in the plant, is a partial HPPD e.g. SEQ ID NO: 1 devoid of amino acids 1-22 (Δ22) and comprising amino acids 1-22 of *Arabidopsis thaliana* as set forth in SEQ ID NO: 106

(MGHQNAAVSENQNHDDGAASSPDNFAIQPPADFTGYDHVTWWVGNAK

QAAAYYTTLFGFETTAYRGLETGSRYFASYVVCNNGVRFVFTSPLRSE

AHLPEDETISDSERKLLKEIHAHLERHGDAVKDVAFEVDNVEAVYNKA

VAEGAIAVQGPTATKDDHGSVTTAVICTYGDTTHTLINRRGYTGPFLP

GFRAGKERTSSVEMPNVPLARIDHCVGNQSWNEMVSACAFYEQCLSFH

RFWSVDDSQICTEFSALNSIVMASPNNLVKMPINEPAPGKKKSQIEEY

VIFNSGPGVQHIALLTPDIITSVSALRARGVEFINVPTTYYDTMRQRL

KTEKRNWQLKEDLDTIQRLNILIDYDEAGYLLQLFTKPLMDRPTVFIE

IIQRNNFEGFGAGNFKSLFEAIEREQAERGNL)

According to some embodiments, the HPPD, expressed in the plant, is a partial HPPD e.g. SEQ ID NO: 1 devoid of amino acids 1-22 (Δ22) and comprising amino acids 1-49 of *Arabidopsis thaliana* as set forth in SEQ ID NO: 107

(MGHQNAAVSENQNHDDGAASSPGFKLVGFSKFVRKNPKSDKFKVKRF

HHDNFAIQPPADFTGYDHVTWWVGNAKQAAAYYTTLFGFETTAYRGLE

TGSRYFASYVVCNNGVRFVFTSPLRSEAHLPEDETISDSERKLLKEIH

AHLERHGDAVKDVAFEVDNVEAVYNKAVAEGAIAVQGPTATKDDHGSV

TTAVICTYGDTTHTLINRRGYTGPFLPGFRAGKERTSSVEMPNVPLAR

IDHCVGNQSWNEMVSACAFYEQCLSFHRFWSVDDSQICTEFSALNSIV

MASPNNLVKMPINEPAPGKKKSQIEEYVIFNSGPGVQHIALLTPDIIT

SVSALRARGVEFINVPTTYYDTMRQRLKTEKRNWQLKEDLDTIQRLNI

LIDYDEAGYLLQLFTKPLMDRPTVFIEIIQRNNFEGFGAGNFKSLFEA

IEREQAERGNL)

According to some embodiments, the HPPD, expressed in the plant, is a partial HPPD e.g. SEQ ID NO: 1 devoid of amino acids 1-38 (Δ38) and comprising amino acids 1-22 of *Arabidopsis thaliana* as set forth in SEQ ID NO: 108

(MGHQNAAVSENQNHDDGAASSPVTWWVGNAKQAAAYYTTLFGFETTA

YRGLETGSRYFASYVVCNNGVRFVFTSPLRSEAHLPEDETISDSERKL

LKEIHAHLERHGDAVKDVAFEVDNVEAVYNKAVAEGAIAVQGPTATKD

DHGSVTTAVICTYGDTTHTLINRRGYTGPFLPGFRAGKERTSSVEMPN

VPLARIDHCVGNQSWNEMVSACAFYEQCLSFHRFWSVDDSQICTEFSA

LNSIVMASPNNLVKMPINEPAPGKKKSQIEEYVIFNSGPGVQHIALLT

PDIITSVSALRARGVEFINVPTTYYDTMRQRLKTEKRNWQLKEDLDTI

QRLNILIDYDEAGYLLQLFTKPLMDRPTVFIEIIQRNNFEGFGAGNFK

SLFEAIEREQAERGNL).

According to some embodiments, the HPPD, expressed in the plant, is a partial HPPD e.g. SEQ ID NO: 1 devoid of amino acids 1-38 (Δ38) and comprising amino acids 1-49 of *Arabidopsis thaliana* as set forth in SEQ ID NO: 109

(MGHQNAAVSENQNHDDGAASSPGFKLVGFSKFVRKNPKSDKFKVKRF

HHVTWWVGNAKQAAAYYTTLFGFETTAYRGLETGSRYFASYVVCNNGV

RFVFTSPLRSEAHLPEDETISDSERKLLKEIHAHLERHGDAVKDVAFE

VDNVEAVYNKAVAEGAIAVQGPTATKDDHGSVTTAVICTYGDTTHTLI

NRRGYTGPFLPGFRAGKERTSSVEMPNVPLARIDHCVGNQSWNEMVSA

CAFYEQCLSFHRFWSVDDSQICTEFSALNSIVMASPNNLVKMPINEPA

PGKKKSQIEEYVIFNSGPGVQHIALLTPDIITSVSALRARGVEFINVP

TTYYDTMRQRLKTEKRNWQLKEDLDTIQRLNILIDYDEAGYLLQLFTK

PLMDRPTVFIEIIQRNNFEGFGAGNEKSLFEAIEREQAERGNL).

According to some embodiments, the HPPD, expressed in the plant, is a partial HPPD e.g. SEQ ID NO: 3 devoid of amino acids 1-22 (Δ22) and comprising amino acids 1-22 of *Arabidopsis thaliana* as set forth in SEQ ID NO: 110

(MGHQNAAVSENQNHDDGAASSPPTTQSALSSYRGYDHVHWYVGNAKQ

AATFYITRMGFSRVAYRGLETGSRSVCSHVVRNGGITFVLTSPLRSPY

-continued

NTEKLERLLPSAEEREYLKEIHEHLARHGDAVKDVAFEVDSVDDVFAA
AVQNGAVAVSQPKTVEDENGQVRVATIRTYGDTTHTLIQRRGVEKPYS
GVFLPGYRDETTSGSSDPITAFLPKVDLRRIDHCVGNQDWDEMEKVCA
YYEKVLGFHRFRSVDDKDICTDYSALKSIVMSSPNDIVKMPINEPAHG
KKQSQIEEYVDFYDGAGVQHIALLTDDIISAITNLKARGVEFIKVPPT
YYDNMWMRLKKAGMMPKEAWEDIKKLDILIDFDEGGYLLQLFTKHLMD
RPTVFIEIIQRNNFSGFGAGNFKSLFEAIEREQALRGNLI).

According to some embodiments, the HPPD, expressed in the plant, is a partial HPPD e.g. SEQ ID NO: 3 devoid of amino acids 1-22 (Δ22) and comprising amino acids 1-49 of Arabidopsis thaliana as set forth in SEQ ID NO: 111

(MGHQNAAVSENQNHDDGAASSPGFKLVGFSKFVRKNPKSDKFKVKRF
HHPTTQSALSSYRGYDHVHWYVGNAKQAATFYITRMGFSRVAYRGLET
GSRSVCSHVVRNGGITFVLTSPLRSPYNTEKLERLLPSAEEREYLKEI
HEHLARHGDAVKDVAFEVDSVDDVFAAAVQNGAVAVSQPKTVEDENGQ
VRVATIRTYGDTTHTLIQRRGVEKPYSGVFLPGYRDETTSGSSDPITA
FLPKVDLRRIDHCVGNQDWDEMEKVCAYYEKVLGFHRFRSVDDKDICT
DYSALKSIVMSSPNDIVKMPINEPAHGKKQSQIEEYVDFYDGAGVQHI
ALLTDDIISAITNLKARGVEFIKVPPTYYDNMWMRLKKAGMMPKEAWE
DIKKLDILIDFDEGGYLLQLFTKHLMDRPTVFIEIIQRNNFSGFGAGN
FKSLFEAIEREQALRGNLI).

According to some embodiments, the HPPD, expressed in the plant, is a partial HPPD e.g. SEQ ID NO: 3 devoid of amino acids 1-30 (Δ30) and comprising amino acids 1-22 of Arabidopsis thaliana as set forth in SEQ ID NO: 112

(MGHQNAAVSENQNHDDGAASSPVHWYVGNAKQAATFYITRMGFSRVAYR
GLETGSRSVCSHVVRNGGITFVLTSPLRSPYNTEKLERLLPSAEEREYLK
EIHEHLARHGDAVKDVAFEVDSVDDVFAAAVQNGAVAVSQPKTVEDENGQ
VRVATIRTYGDTTHTLIQRRGVEKPYSGVFLPGYRDETTSGSSDPITAFL
PKVDLRRIDHCVGNQDWDEMEKVCAYYEKVLGFHRFRSVDDKDICTDYSA
LKSIVMSSPNDIVKMPINEPAHGKKQSQIEEYVDFYDGAGVQHIALLTDD
IISAITNLKARGVEFIKVPPTYYDNMWMRLKKAGMMPKEAWEDIKKLDIL
IDFDEGGYLLQLFTKHLMDRPTVFIEIIQRNNFSGFGAGNFKSLFEAIER
EQALRGNLI).

According to some embodiments, the HPPD, expressed in the plant, is a partial HPPD e.g. SEQ ID NO: 3 devoid of amino acids 1-30 (Δ30) and comprising amino acids 1-49 of Arabidopsis thaliana as set forth in SEQ ID NO: 113

(MGHQNAAVSENQNHDDGAASSPGFKLVGFSKFVRKNPKSDKFKVKRF
HHVHWYVGNAKQAATFYITRMGFSRVAYRGLETGSRSVCSHVVRNGGI
TFVLTSPLRSPYNTEKLERLLPSAEEREYLKEIHEHLARHGDAVKDVA
FEVDSVDDVFAAAVQNGAVAVSQPKTVEDENGQVRVATIRTYGDTTHT
LIQRRGVEKPYSGVFLPGYRDETTSGSSDPITAFLPKVDLRRIDHCVG
NQDWDEMEKVCAYYEKVLGFHRFRSVDDKDICTDYSALKSIVMSSPND
IVKMPINEPAHGKKQSQIEEYVDFYDGAGVQHIALLTDDIISAITNLK
ARGVEFIKVPPTYYDNMWMRLKKAGMMPKEAWEDIKKLDILIDFDEGG
YLLQLFTKHLMDRPTVFIEIIQRNNFSGFGAGNFKSLFEAIEREQALR
GNLI)

According to some embodiments, the HPPD, expressed in the plant, is wt HPPD e.g. SEQ ID NO: 1 to which amino acids 1-22 of Arabidopsis thaliana has been added as set forth in SEQ ID NO: 114

(MGHQNAAVSENQNHDDGAASSPMSPSAISNSPEQRPANNNGTTPDNF
AIQPPADFTGYDHVTWWVGNAKQAAAYYTTLFGFETTAYRGLETGSRY
FASYVVCNNGVRFVFTSPLRSEAHLPEDETISDSERKLLKEIHAHLER
HGDAVKDVAFEVDNVEAVYNKAVAEGAIAVQGPTATKDDHGSVTTAVI
CTYGDTTHTLINRRGYTGPFLPGFRAGKERTSSVEMPNVPLARIDHCV
GNQSWNEMVSACAFYEQCLSFHRFWSVDDSQICTEFSALNSIVMASPN
NLVKMPINEPAPGKKKSQIEEYVIFNSGPGVQHIALLTPDIITSVSAL
RARGVEFINVPTTYYDTMRQRLKTEKRNWQLKEDLDTIQRLNILIDYD
EAGYLLQLFTKPLMDRPTVFIEIIQRNNFEGFGAGNFKSLFEAIEREQ
AERGNL)

According to some embodiments, the HPPD, expressed in the plant, is wt HPPD e.g. SEQ ID NO: 1 to which amino acids 1-49 of Arabidopsis thaliana has been added as set forth in SEQ ID NO: 115

(MGHQNAAVSENQNHDDGAASSPGFKLVGFSKFVRKNPKSDKFKVKRF
HHMSPSAISNSPEQRPANNNGTTPDNFAIQPPADFTGYDHVTWWVGNA
KQAAAYYTTLFGFETTAYRGLETGSRYFASYVVCNNGVRFVFTSPLRS
EAHLPEDETISDSERKLLKEIHAHLERHGDAVKDVAFEVDNVEAVYNK
AVAEGAIAVQGPTATKDDHGSVTTAVICTYGDTTHTLINRRGYTGPFL
PGFRAGKERTSSVEMPNVPLARIDHCVGNQSWNEMVSACAFYEQCLSF
HRFWSVDDSQICTEFSALNSIVMASPNNLVKMPINEPAPGKKKSQIEE
YVIFNSGPGVQHIALLTPDIITSVSALRARGVEFINVPTTYYDTMRQR
LKTEKRNWQLKEDLDTIQRLNILIDYDEAGYLLQLFTKPLMDRPTVFI
EIIQRNNFEGFGAGNFKSLFEAIEREQAERGNL)

According to some embodiments, the HPPD, expressed in the plant, is wt HPPD e.g. SEQ ID NO: 3 to which amino acids 1-22 of Arabidopsis thaliana has been added as set forth in SEQ ID NO: 116

(MGHQNAAVSENQNHDDGAASSPMAPSAISDLQSDNLPTTQSALSSYR
GYDHVWYVGNAKQAATFYITRMGFSRVAYRGLETGSRSVCSHVVRNG
GITFVLTSPLRSPYNTEKLERLLPSAEEREYLKEIHEHLARHGDAVKD

-continued

VAFEVDSVDDVFAAAVQNGAVAVSQPKTVEDENGQVRVATIRTYGDTT

HTLIQRRGVEKPYSGVFLPGYRDETTSGSSDPITAFLPKVDLRRIDHC

VGNQDWDEMEKVCAYYEKVLGFHRFRSVDDKDICTDYSALKSIVMSSP

NDIVKMPINEPAHGKKQSQIEEYVDFYDGAGVQHIALLTDDIISAITN

LKARGVEFIKVPPTYYDNMWMRLKKAGMMPKEAWEDIKKLDILIDFDE

GGYLLQLFTKHLMDRPTVFIEIIQRNNFSGFGAGNFKSLFEAIEREQA

LRGNLI)

According to some embodiments, the HPPD, expressed in the plant, is wt HPPD e.g. SEQ ID NO: 3 to which amino acids 1-49 of *Arabidopsis thaliana* has been added as set forth in SEQ ID NO: 117

(MGHQNAAVSENQNHDDGAASSPGFKLVGFSKFVRKNPKSDKFKVKRF

HHMAPSAISDLQSDNLPTTQSALSSYRGYDHVHWYVGNAKQAATFYIT

RMGFSRVAYRGLETGSRSVCSHVVRNGGITFVLTSPLRSPYNTEKLER

LLPSAEEREYLKEIHEHLARHGDAVKDVAFEVDSVDDVFAAAVQNGAV

AVSQPKTVEDENGQVRVATIRTYGDTTHTLIQRRGVEKPYSGVFLPGY

RDETTSGSSDPITAFLPKVDLRRIDHCVGNQDWDEMEKVCAYYEKVLG

FHRFRSVDDKDICTDYSALKSIVMSSPNDIVKMPINEPAHGKKQSQIE

EYVDFYDGAGVQHIALLTDDIISAITNLKARGVEFIKVPPTYYDNMWM

RLKKAGMMPKEAWEDIKKLDILIDFDEGGYLLQLFTKHLMDRPTVFIE

IIQRNNFSGFGAGNFKSLFEAIEREQALRGNLI)

Plant Expression Cassettes

The compositions of the invention may additionally contain nucleic acid sequences for transformation and expression in a plant of interest. The nucleic acid sequences may be present in DNA constructs or expression cassettes. The term "Expression cassette" as used herein means a nucleic acid molecule capable of directing expression of a particular nucleotide sequence in an appropriate host cell, comprising a promoter operatively linked to the nucleotide sequence of interest (i.e., a polynucleotide encoding the herein disclosed fungus-derived HPPD polypeptide or variant thereof that retains HPPD enzymatic activity, alone or in combination with one or more additional nucleic acid molecules encoding polypeptides that confer desirable traits, which is operatively linked to termination signals). It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. Additionally, the promoter can also be specific to a particular tissue or organ or stage of development.

The present invention encompasses the transformation of plants with expression cassettes capable of expressing a polynucleotide of interest, i.e., a polynucleotide encoding the fungus-derived HPPD polypeptide or variant thereof that retains HPPD enzymatic activity, alone or in combination with one or more additional nucleic acid molecules encoding polypeptides that confer desirable traits. The expression cassette will include in the 5'-3' direction of transcription, a transcriptional and translational initiation region (i.e., a promoter) and a polynucleotide open reading frame. The expression cassette may optionally comprise a transcriptional and translational termination region (i.e., termination region) functional in plants. In some embodiments, the expression cassette comprises a selectable marker gene to allow for selection for stable transformants. Expression constructs of the invention may also comprise a leader sequence and/or a sequence allowing for inducible expression of the polynucleotide of interest.

The regulatory sequences of the expression construct are operably linked to the polynucleotide of interest. By "operably linked" is intended a functional linkage between a promoter and a second sequence wherein the promoter sequence initiates and mediates transcription of the DNA sequence corresponding to the second sequence. Generally, operably linked means that the nucleotide sequences being linked are contiguous.

Any promoter capable of driving expression in the plant of interest may be used in the practice of the invention. The promoter may be native or analogous or foreign or heterologous to the plant host. The terms "heterologous" and "exogenous" when used herein to refer to a nucleic acid sequence (e.g. a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" nucleic acid (e.g., DNA) sequence is a nucleic acid (e.g., DNA or RNA) sequence naturally associated with a host cell into which it is introduced.

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to that sequence. The promoters that are used for expression of the transgene(s) can be a strong plant promoter, a viral promoter, or a chimeric promoter composed of elements such as: TATA box from any gene (or synthetic, based on analysis of plant gene TATA boxes), optionally fused to the region 5' to the TATA box of plant promoters (which direct tissue and temporally appropriate gene expression), optionally fused to 1 or more enhancers (such as the 35S enhancer, FMV enhancer, CMP enhancer, RUBISCO SMALL SUBUNIT enhancer, PLASTOCYANIN enhancer).

Exemplary constitutive promoters include, for example, the core promoter of the Rsyn7 promoter and other constitutive promoters; the core CaMV 35S promoter; rice actin; ubiquitin; pEMU; MAS; ALS promoter, and the like.

Appropriate plant or chimeric promoters are useful for applications such as expression of transgenes in certain tissues, while minimizing expression in other tissues, such as seeds, or reproductive tissues. Exemplary cell type- or tissue-preferential promoters drive expression preferentially in the target tissue but may also lead to some expression in other cell types or tissues as well.

In other embodiments of the present invention, inducible promoters may be desired. Inducible promoters drive transcription in response to external stimuli such as chemical agents or environmental stimuli. For example, inducible promoters can confer transcription in response to hormones such as gibberellic acid or ethylene, or in response to light or drought.

A variety of transcriptional terminators are available for use in expression cassettes. These are responsible for the termination of transcription beyond the transgene and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator, the octopine synthase terminator and the pea rbcs E9 terminator. These can be used in both monocotyledons and dicotyledons. In addition, a gene's native transcription terminator may be used.

Generally, the expression cassette will comprise a selectable marker gene for the selection of transformed cells. Selectable marker genes are utilized for the selection of transformed cells or tissues.

Numerous sequences have been found to enhance gene expression from within the transcriptional unit and these sequences can be used in conjunction with the genes of this invention to increase their expression in plants.

Various intron sequences have been shown to enhance expression, particularly in monocotyledonous cells. For example, the introns of the maize Adhl gene have been found to significantly enhance the expression of the wild-type gene under its cognate promoter when introduced into maize cells. Intron 1 was found to be particularly effective and enhanced expression in fusion constructs with the chloramphenicol acetyltransferase gene. In the same experimental system, the intron from the maize bronze 1 gene had a similar effect in enhancing expression. Intron sequences have been routinely incorporated into plant transformation vectors, typically within the non-translated leader.

The present invention also relates to nucleic acid constructs comprising one or more of the expression cassettes described above. The construct can be a vector, such as a plant transformation vector. In one embodiment, the vector is a plant transformation vector comprising a polynucleotide comprising the sequence set forth in SEQ ID NO: 2, 4 or any other polynucleotide encoding the amino acid sequence set forth in SEQ ID NO: 1, 3, and/or 5-8.

Plants

As used herein, the term "plant part" or "plant tissue" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. The aforementioned term also includes plant products, such as grain, fruits, and nuts.

The plants disclosed herein are genetically modified to express an HPPD enzyme not naturally expressed in the plant (or in plants in general), such as to express the herein disclosed fungus-derived HPPD polypeptide or variant thereof that retains HPPD enzymatic activity in the plant.

As used herein, the term "genetically modified" may refer to transgenic plants transformed to stably express the non-naturally occurring HPPD enzyme as well as to plants being modified genetically to express a non-naturally occurring HPPD enzyme (mutation or substitution) using gene editing technologies, such as but not limited to CRISPR/Cas, TAL-LEN and zink-finger technologies. According to some embodiments, the genetically modified plant is a transgenic plant. According to some embodiments, the genetically modified plant having a HPPD enzyme modified by gene editing. According to some embodiments, the HPPD enzyme may be an exogenously introduced HPPD enzyme, such as, but not limited to the HPPD enzymes derived from *Trichoderma* spp or *Talaromyces* spp disclosed herein. According to some embodiments, the HPPD enzyme may be the endogenous HPPD of the plant genetically modified to include fungal derived motifs and/or mutations, rendering the plant resistant to the HPPD inhibitors.

The type of plant selected depends on a variety of factors, including for example, the downstream use of the harvested plant material, amenability of the plant species to transformation, and the conditions under which the plants will be grown, harvested, and/or processed. One of skill will further recognize that additional factors for selecting appropriate plant varieties for use in the present invention include high yield potential, good stalk strength, resistance to specific diseases, drought tolerance, rapid dry down and grain quality sufficient to allow storage and shipment to market with minimum loss.

Plants according to the present invention include any plant that is cultivated for the purpose of producing plant material that is sought after by man or animal for either oral consumption, or for utilization in an industrial, pharmaceutical, or commercial process. The invention may be applied to any of a variety of plants, including, but not limited to maize, wheat, rice, barley, soybean, cowpea, chickpea, cotton, sorghum, oat, beans in general, rape/canola, alfalfa, flax, sunflower, safflower, millet, rye, sugarcane, sugar beet, cocoa, tea, *Brassica*, cotton, coffee, sweet potato, flax, peanut, clover; vegetables such as lettuce, tomato, cucurbits, cassava, potato, carrot, radish, pea, lentils, cabbage, cauliflower, broccoli, Brussels sprouts, peppers, and pineapple; tree fruits such as citrus, apples, pears, peaches, apricots, walnuts, avocado, banana, palm, eucalyptus, poplar, pine and coconut; and flowers such as orchids, petunia, carnations and roses. Other plants useful in the practice of the invention include perennial grasses, such as switchgrass, prairie grasses, indiangrass, big bluestem grass and the like. It is recognized that mixtures of plants may be used.

In addition, the term "crop" is to be understood as also including crop that have been rendered tolerant to herbicides or classes of herbicides (such as, for example, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. Examples of crops that have been rendered tolerant to herbicides or classes of herbicides by genetic engineering methods include glyphosate- and glufosinate-resistant crop varieties. The method according to the present invention is especially suitable for the protection of crops where HPPD herbicides are used for weed control.

Plant Transformation

Once an herbicide resistant or tolerant HPPD polynucleotide, alone or in combination with one or more additional nucleic acid molecules encoding polypeptides that confer desirable traits, has been cloned into an expression system, it is transformed into a plant cell. The expression cassettes of the present invention can be introduced into the plant cell in a number of art-recognized ways. The term "introducing" in the context of a polynucleotide, for example, a nucleotide construct of interest, is intended to mean presenting to the plant the polynucleotide in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors. Accordingly, these polynucleotides can be introduced into the host cell of interest in a single transformation event, in separate transformation events, or, for example, in plants, as part of a breeding protocol. The methods of the invention do not depend on a particular method for introducing one or more polynucleotides into a plant, only that the polynucleotide(s) gains access to the interior of at least one cell of the plant. Methods for introducing polynucleotides into plants are known in the art including, but not limited to, transient transformation methods, stable transformation methods, and virus-mediated methods.

"Transient transformation" in the context of a polynucleotide is intended to mean that a polynucleotide is introduced into the plant and does not integrate into the genome of the plant. "Stable transformation" or "stably transformed" is intended to mean that a polynucleotide, for example, a nucleotide construct described herein, introduced into a plant integrates into the genome of the plant and is capable of being inherited by the progeny thereof, more particularly, by the progeny of multiple successive generations.

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. According to some embodiments, the HPPD gene of the current invention is, in combination with the use of an HPPD herbicide as selection agent, itself used as the selectable marker.

Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Another approach to transforming plant cells with a gene involves propelling inert or biologically active particles at plant tissues and cells. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e., co-transformation) and both of these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome.

The plants obtained via transformation with a nucleic acid sequence of interest in the present invention can be any of a wide variety of plant species, including those of monocots and dicots; however, the plants used in the method of the invention are preferably selected from the list of agronomically important target crops set forth elsewhere herein. The expression of a gene of the present invention in combination with other characteristics important for production and quality can be incorporated into plant lines through breeding.

The genetic properties engineered into the seeds and plants described above may be passed on by sexual reproduction or vegetative growth and can thus be maintained and propagated in progeny plants. Generally, maintenance and propagation make use of known agricultural methods developed to fit specific purposes such as tilling, sowing or harvesting.

Use of the advantageous genetic properties of the plants and seeds according to the invention can further be made in plant breeding. Depending on the desired properties, different breeding measures are taken. The relevant techniques are well known in the art and include but are not limited to hybridization, inbreeding, backcross breeding, multi-line breeding, variety blend, interspecific hybridization, aneuploid techniques, etc. Thus, the seeds and plants according to the invention can be used for the breeding of improved plant lines that, for example, increase the effectiveness of conventional methods such as herbicide or pesticide treatment or allow one to dispense with said methods due to their modified genetic properties.

Herbicide Resistance

The present invention provides plants, plant cells, tissues, and seeds that have been genetically modified with a nucleic acid molecule encoding a fungus derived HPPD or variant thereof and/or to plants in which the endogenous HPPD has been edited (e.g. by CRISPR/Cas technology, TALLEN, Zink-finger etc.) to include fungus derived motifs and/or mutations, thereby providing plants with an HPPD that confers resistance or tolerance to herbicides, optionally combination with one or more additional nucleic acid molecules encoding polypeptides that confer desirable traits.

In one embodiment, the plants of the invention exhibit resistance or tolerance to application of herbicide in an amount of from about 5 to about 2,000 grams per hectare (g/ha), including, for example, about 5 g/ha, about 10 g/ha, about 15 g/ha, about 20 g/ha, about 25 g/ha, about 30 g/ha, about 35 g/ha, about 40 g/ha, about 45 g/ha, about 50 g/ha, about 55 g/ha, about 60 g/ha, about 65 g/ha, about 70 g/ha, about 75 g/ha, about 80 g/ha, about 85 g/ha, about 90 g/ha, about 95 g/ha, about 100 g/ha, about 110 g/ha, about 120 g/ha, about 130 g/ha, about 140 g/ha, about 150 g/ha, about 160 g/ha, about 170 g/ha, about 180 g/ha, about 190 g/ha, about 200 g/ha, about 210 g/ha, about 220 g/ha, about 230 g/ha, about 240 g/ha, about 250 g/ha, about 260 g/ha, about 270 g/ha, about 280 g/ha, about 290 g/ha, about 300 g/ha, about 310 g/ha, about 320 g/ha, about 330 g/ha, about 340 g/ha, about 350 g/ha, about 360 g/ha, about 370 g/ha, about 380 g/ha, about 390 g/ha, about 400 g/ha, about 410 g/ha, about 420 g/ha, about 430 g/ha, about 440 g/ha, about 450 g/ha, about 460 g/ha, about 470 g/ha, about 480 g/ha, about 490 g/ha, about 500 g/ha, about 510 g/ha, about 520 g/ha, about 530 g/ha, about 540 g/ha, about 550 g/ha, about 560 g/ha, about 570 g/ha, about 580 g/ha, about 590 g/ha, about 600 g/ha, about 610 g/ha, about 620 g/ha, about 630 g/ha, about 640 g/ha, about 650 g/ha, about 660 g/ha, about 670 g/ha, about 680 g/ha, about 690 g/ha, about 700 g/ha, about 710 g/ha, about 720 g/ha, about 730 g/ha, about 740 g/ha, about 750 g/ha, about 760 g/ha, about 770 g/ha, about 780 g/ha, about 790 g/ha, about 800 g/ha, about 810 g/ha, about 820 g/ha, about 830 g/ha, about 840 g/ha, about 850 g/ha, about 860 g/ha, about 870 g/ha, about 880 g/ha, about 890 g/ha, about 900 g/ha, about 910 g/ha, about 920 g/ha, about 930 g/ha, about 940 g/ha, about 950 g/ha, about 960 g/ha, about 970 g/ha, about 980 g/ha, about 990 g/ha, about 1,000 g/ha, about 1,010 g/ha, about 1,020 g/ha, about 1,030 g/ha, about 1,040 g/ha, about 1,050 g/ha, about 1,060 g/ha, about 1,070 g/ha, about 1,080 g/ha, about 1,090 g/ha, about 1,100 g/ha, about 1,110 g/ha, about 1,120 g/ha, about 1,130 g/ha, about 1,140 g/ha, about 1,150 g/ha, about 1,160 g/ha, about 1,170 g/ha, about 1,180 g/ha, about 1,190 g/ha, about 1,200 g/ha, about 1,210 g/ha, about 1,220 g/ha, about 1,230 g/ha, about 1,240 g/ha, about 1,250 g/ha, about 1,260 g/ha, about 1,270 g/ha, about 1,280 g/ha, about 1,290 g/ha, about 1,300 g/ha, about 1,310 g/ha, about 1,320 g/ha, about 1,330 g/ha, about 1,340 g/ha, about 1,350 g/ha, about 1,360 g/ha, about 1,370 g/ha, about 1,380 g/ha, about 1,390 g/ha, about 1,400 g/ha, about 1,410 g/ha, about 1,420 g/ha, about 1,430 g/ha, about 1,440 g/ha, about 1,450 g/ha, about 1,460 g/ha, about 1,470 g/ha, about 1,480 g/ha, about 1,490 g/ha, about 1,500 g/ha, about 1,510 g/ha, about 1,520 g/ha, about 1,530 g/ha, about 1,540 g/ha, about 1,550 g/ha, about 1,560 g/ha, about 1,570 g/ha, about 1,580 g/ha, about 1,590 g/ha, about 1,600 g/ha, about 1,610 g/ha, about 1,620 g/ha, about 1,630 g/ha, about 1,640 g/ha, about 1,650 g/ha, about 1,660 g/ha, about 1,670 g/ha, about 1,680 g/ha, about 1,690 g/ha, about 1,700 g/ha, about 1,710 g/ha, about 1,720 g/ha, about 1,730 g/ha, about 1,740 g/ha, about 1,750 g/ha, about 1,760 g/ha, about 1,770 g/ha, about 1,780 g/ha, about 1,790 g/ha, about 1,800 g/ha, about 1,810 g/ha, about 1,820 g/ha, about 1,830 g/ha, about 1,840 g/ha, about 1,850 g/ha, about 1,860 g/ha, about 1,870 g/ha, about 1,880 g/ha, about 1,890 g/ha, about 1,900 g/ha, about 1,910 g/ha, about 1,920 g/ha, about 1,930 g/ha, about 1,940 g/ha, about 1,950 g/ha, about 1,960 g/ha, about 1,970 g/ha, about 1,980 g/ha, about 1,990 g/ha, or about 2,000 g/ha.

The methods of the present invention are especially useful to protect crops from the herbicidal injury of HPPD inhibitor herbicides. For example, the HPPD inhibiting herbicide is suitably selected from the group consisting of bicyclopyrone (CAS RN 352010-68-5), benzobicyclon (CAS RN 156963-66-5), benzofenap (CAS RN 82692-44-2), ketospiradox (CAS RN 192708-91-1) or its free acid (CAS RN 187270-87-7), isoxachlortole (CAS RN 141112-06-3), isoxaflutole (CAS RN 141112-29-0), mesotrione (CAS RN 104206-82-8), pyrasulfotole (CAS RN 365400-11-9), pyrazolynate (CAS RN 58011-68-0), pyrazoxyfen (CAS RN 71561-11-0), sulcotrione (CAS RN 99105-77-8), tefuryltrione (CAS RN 473278-76-1), tembotrione (CAS RN 335104-84-2) and topramezone (CAS RN 210631-68-8); including, where applicable, agrochemically acceptable salts thereof.

Methods of Use

The present invention further provides a method of selectively controlling weeds at a locus comprising crop plants and weeds, wherein the plants are obtained by any of the methods of the current invention described above, wherein the method comprises application to the locus of a weed controlling amount of one or more herbicides. Any of the plants described herein may be used within these methods of the invention. The term "locus" may include soil, seeds, and seedlings, as well as established vegetation. Herbicides can suitably be applied pre-emergence or post-emergence of the crop or weeds.

The term "weed controlling amount" is meant to include functionally, an amount of herbicide which is capable of affecting the growth or development of a given weed. Thus, the amount may be small enough to simply retard or suppress the growth or development of a given weed, or the amount may be large enough to irreversibly destroy a given weed.

Thus, the present invention provides a method of controlling weeds at a locus comprising applying to the locus a weed-controlling amount of one or more herbicides, where the locus comprises a plant that has been transformed with a nucleic acid molecule encoding the herein disclosed fungus-derived HPPD polypeptide or variant thereof that confers resistance or tolerance to HPPD herbicides, alone or in combination with one or more additional nucleic acid molecules encoding polypeptides that confer desirable traits.

In one embodiment, the present invention provides plants and methods useful for the control of unwanted plant species in crop fields, wherein the crop plants are made resistant to HPPD chemistry by transformation to express genes encoding the herein disclosed fungus-derived HPPD polypeptides, and where an HPPD herbicide is applied as an over-the-top application in amounts capable of killing or impairing the growth of unwanted plant species (weed species, or, for example, carry-over or "rogue" or "volunteer" crop plants in a field of desirable crop plants). The application may be pre- or post-emergence of the crop plants or of the unwanted species, and may be combined with the application of other herbicides to which the crop is naturally tolerant, or to which it is resistant via expression of one or more other herbicide resistance transgenes.

In another embodiment, the invention also relates to a method of protecting crop plants from herbicidal injury. In the cultivation of crop plants, especially on a commercial scale, correct crop rotation is crucially important for yield stability (the achievement of high yields of good quality over a long period) and for the economic success of an agronomic business. Use of the herbicide may cause agronomically unacceptable phytotoxic damage to the crop plants in subsequent crops ("carry-over" damage). Accordingly, the herbicide resistant or tolerant plants of the invention are also useful for planting in a locus of any short term carry-over of herbicide from a previous application (e.g., by planting a plant of the invention in the year following application of an herbicide to reduce the risk of damage from soil residues of the herbicide).

EXAMPLES

The invention is now described with reference to the following Examples. These Examples are provided for the purpose of illustration only, and the invention is not limited to these Examples, but rather encompasses all variations which are evident as a result of the teachings provided herein.

Isolation

A putative fungus was isolated from x0.25 YENB agar plate with chloramphenicol (50 µg/ml) and Penicillin-Streptomycin (100 units penicillin and 100 µg Streptomycin per ml).

Gene Annotation

A first isolated fungus was shown to belong to the genus *Trichoderma* spp., by sequencing, several genes including 18S Internal Transcribed spacer1 (ITS1), translation elongation factor 1-alpha (tef1), endochitinase 42 (ech42) and RNA polymerase II (rpb2), followed by whole genome sequencing of the fungus. A 4-Hydroxyphenylpyruvate dioxygenase (HPPD) gene of the isolated fungus was detected by homology search (BLASTx) and cloned.

Another fungus was shown to belong to the genus *Talaromyces* spp., by sequencing several genes. A 4-Hydroxyphenylpyruvate dioxygenase (HPPD) gene of the isolated fungus was detected by homology search (BLASTx) and cloned.

Bacterial HPPD-Activity Assay

The coding sequence of the identified hppd cDNA was amplified by PCR and cloned to a pET16 expression vector. *E. coli* BL21 (DE3) were transformed with the expression vector and monitored for HPPD activity using a colorimetric method as essentially explained in Rocaboy-Faquet. E. et al. (DOI: 10.1007/s00253-014-5793-5) with two minor modifications, namely: 1) The transformed bacteria were inoculated on an agar based medium instead of a liquid medium; 2) The screen was performed at 25° C. for 4 days.

The screen media was prepared with a concentration gradient of HPPD inhibitors at the indicated concentrations and the transformed bacteria were inoculated on the screening agar plates. HPPD activity was detected by a brown halo resulting from the HPPD-mediated conversion of p-hydroxyphenylpyruvate (HPP) into homogentisate (HGA), which later is oxidized to a melanin-like pigment. Tembotrione resistance of the transformed bacteria was compared to that of plates inoculated with *E. coli* BL21 (DE3) transformed with either an empty pET16 vector or a pET16 vector transformed with *Arabidopsis thaliana* hppd cDNA (accession no. AF047834).

As seen in FIG. 1, transformation of *E. coli* BL21 (DE3) with the HPPD derived from the novel *Trichoderma* fungus (TP) resulted in detection of HPPD activity (brown halo) on plates with as much as to 250 µg/ml of Tembotrione, 250 µg/ml of Mesotrione, 25 µg/ml of isoxaflutole, 25 µg/ml of Topramezone and 1250 µg/ml of Pyrazoxyfen, while of *E. coli* BL21 (DE3) transformed with the *Arabidopsis thaliana* HPPD (AtHPPD) showed poor HPPD activity if at all. No activity was detected in the empty vector control plates (0).

In-Planta Screen of Plants Transformed with Fungal HPPD

The hppd coding region was cloned into pPA35H binary vector under the control of the CaMV35S constitutive promoter and HSP terminator and was used to transform *Arabidopsis* plants using *agrobacterium* according to the dipping flower method, as essentially described in WO 2018/178975. T1 generation transformed seeds were germinated on Basta selection (Bayer) according to manufacturer instructions. 3-4 days post germination, plants were treated with 0.1% and 0.05% Tembotrione (Laudis (Bayer)). HPPD resistant plants were detected one-week post germination.

Figure 2:
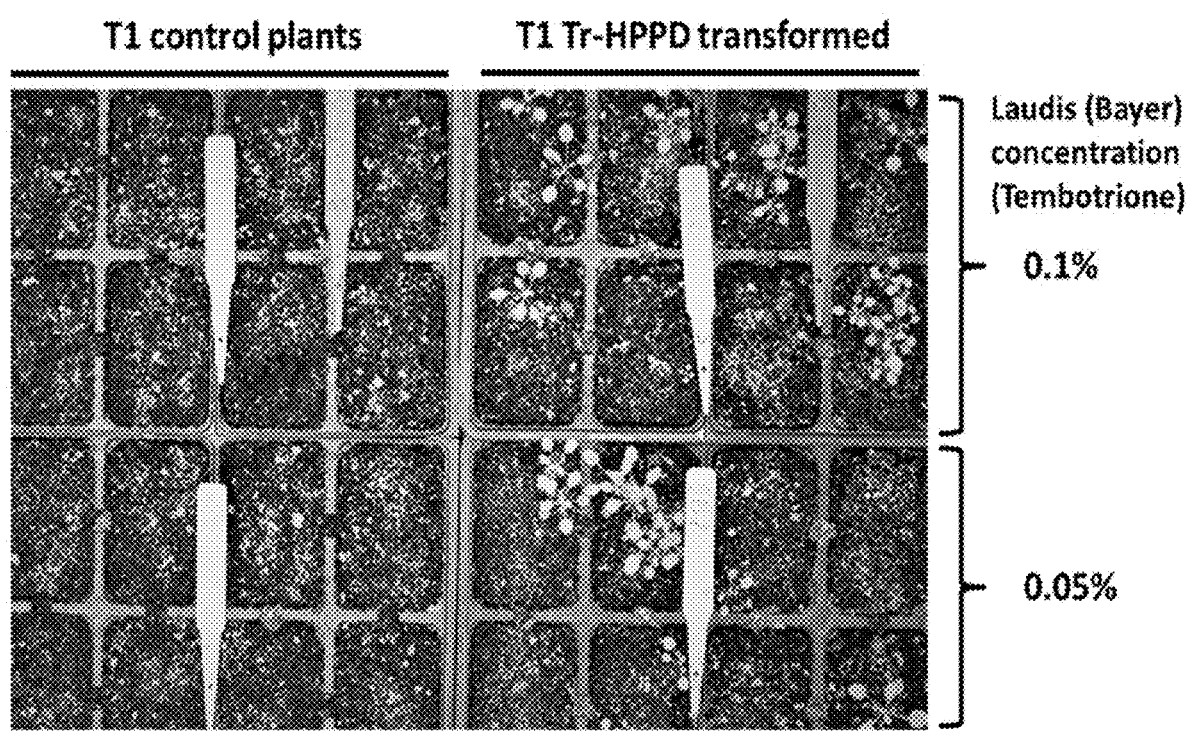
FIG. 2 shows illustrative images of *Arabidopsis* T1 plants transformed to express the herein disclosed *Trichoderma* spp-HPPD gene as compared to control (non-transformed), when grown on Basta and treated with 0.1% or 0.05% Tembotrione.

As seen from FIG. 2, transformation of *Arabidopsis* T1 plants with the herein disclosed *Trichoderma* spp-HPPD gene enabled growth in the presences of the Tembotrione herbicide, while no plant growth was observed in the control. This shows that transformation of plant to express the herein disclosed *Trichoderma* spp-HPPD gene enables its growth in the presence of the herbicide Tembotrione, which is highly effective in weed control of plants in particular broad leaf.

Figure 3A:
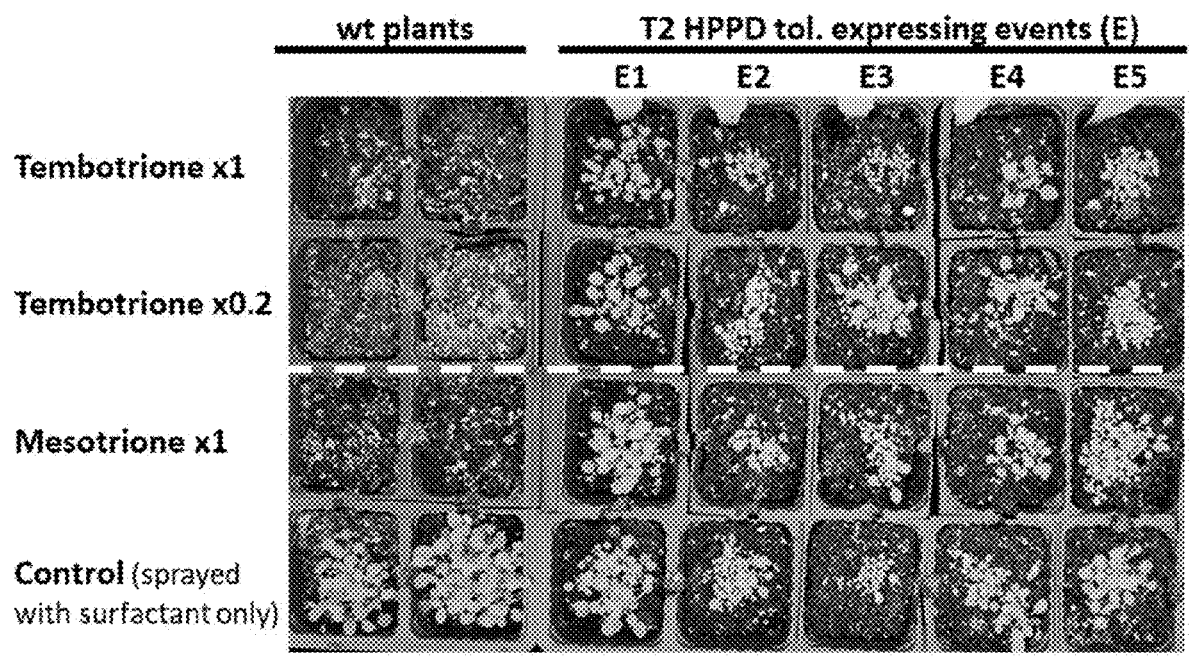
FIG. 3A and FIG. 3B show illustrative images of *Arabidopsis* T2 plants transformed to express the herein disclosed *Trichoderma* spp-HPPD gene as compared to control (wild type (wt) non-transformed), when grown on Basta and treated with Tembotrione x1, Tembotrione x0.2 and Mesotrione x1 (FIG. 3A) and Tembotrione x1, Topramezon x0.2, Topramezon x1, Isoxaflutole x1 (FIG. 3B).
Figure 3B:
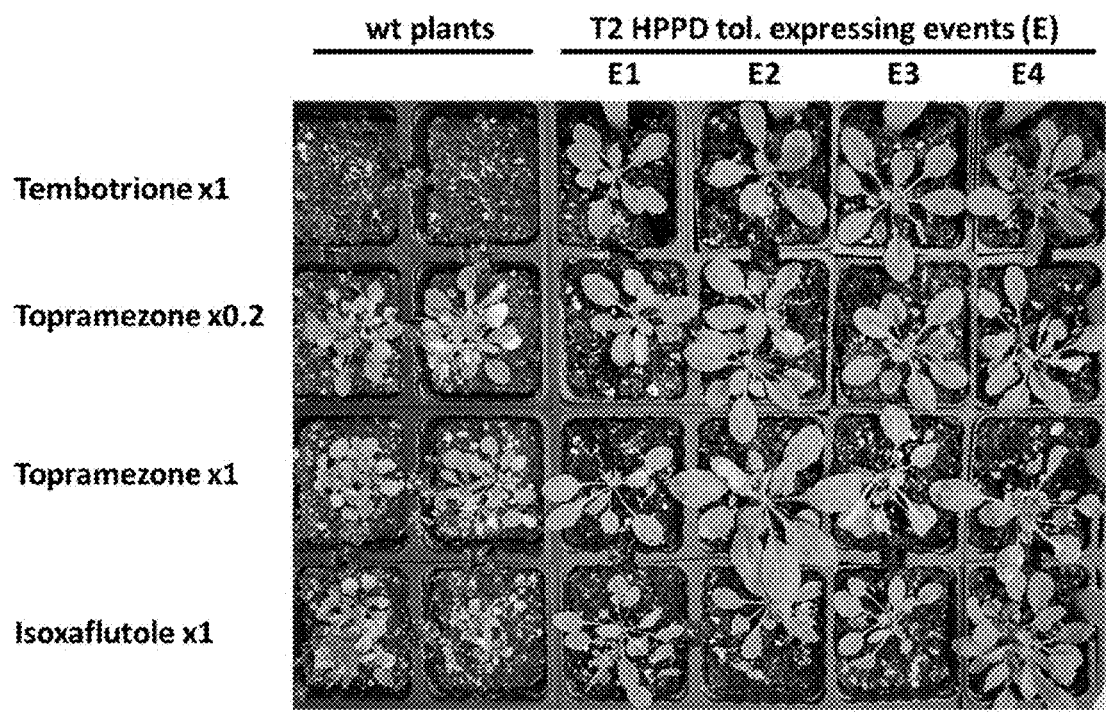

As seen from FIG. 3, T2 generation transformed seeds of *Arabidopsis* plants with the herein disclosed *Trichoderma* spp-HPPD gene enabled growth in the presences of the Tembotrione (x1=2500 µg/ml and x0.2=500 µg/ml), Mesotrione (x1=50 µg/ml), Topramezon (x1=150 µg/ml and x0.2=30 µg/ml) and Isoxaflutole (x1=50 µg/ml) herbicides, while no plant growth or an acute growth inhibition and leaf bleaching were observed in the control (wt plants). This shows that transformation of plant to express the herein disclosed *Trichoderma* spp-HPPD gene enables its growth in the presence of the herbicide Tembotrione, Mesotrione, Topramezon and Isoxaflutole, which are highly effective in weed control of plants, in particular broad leaf plants. This results emphasis the advantageous tolerance of plant transformed to express the herein-disclosed *Trichoderma* spp-HPPD gene to different HPPD inhibitors.

Structure

Structural prediction of SEQ ID NO: 1 was performed using MODELLER (Webb B, Sali A. Curr Protoc Protein Sci. 2016 Nov. 1; 86:2.9.1-2.9.37) via the hhpred server (Zimmermann L et al. J Mol Biol. 2018 Jul. 20. S0022-2836 (17)30587-9) using PDB entries 1T47, 1SP8 and 1FTZ as best fit templates (48.1%, 31.7% and 33.8% seq ID respectively).

The predicted structure was fitted on the HPPD structure of *A. thaliana* (PDB: 5YWG) with ExPASy Swiss-PdbViewer (Guex, N. and Peitsch, M. C. Electrophoresis 1997 18, 2714-2723) iterative magic fit (RMS=1.01 Å).

Figure 4:
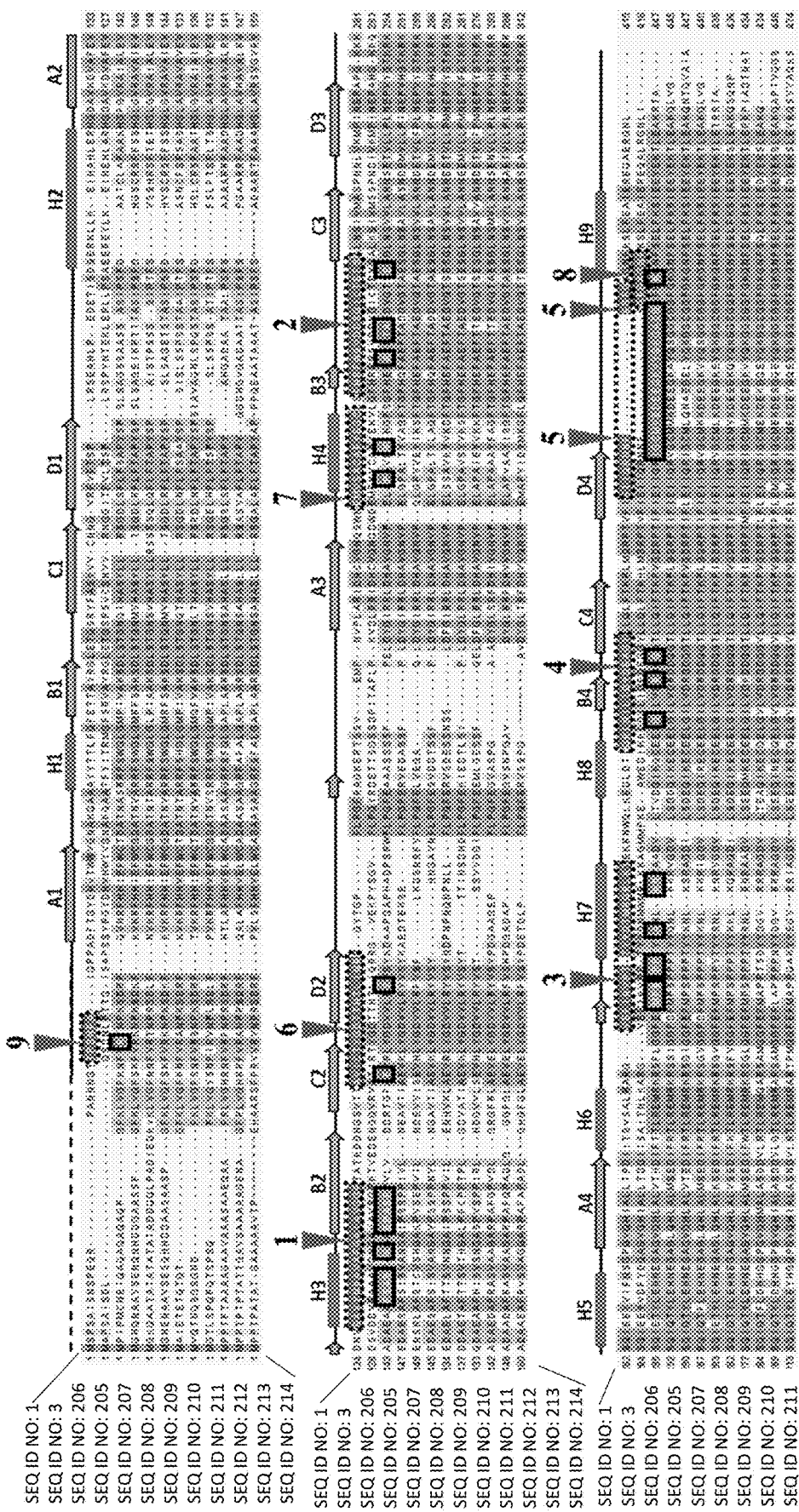
FIG. 4 shows the alignment of twelve different HPPD sequences. The positions of secondary structural elements are shown on top of the alignment. Motifs 1-9 are framed by dashed line boxes. Motif numbers are indicated by triangles and corresponding numbers. Structural elements are indicated by boxes/arrows above the sequences: H indicating α-helix, A-D indicating β-sheets. Mutations designed for soy HPPD are framed by solid line boxes over the soy sequence.

Multiple sequence alignment of SEQ ID NO: 1 with SEQ ID NO: 3 and Plant HPPD sequences of *Arabidopsis thaliana* (At_HPPD), *Brassica napus*—Canola (Bn_HPPD), *Zea mays*—Corn (Zm_HPPD), *Solanum tuberosum*—Potato (St_HPPD), *Glycine max*—Soy (Gm_HPPD), *Medicago sativa*—Alfalfa (Ms_HPPD), *Gossypium hirsutum*—Cotton (Gh_HPPD), *Beta vulgaris*—Sugar beet (Bv_HPPD) *Oryza sativa*—Rice (Os_HPPD) and *Avena sativa*—Oat (As_HPPD) was performed via T-coffee server with expresso mode (Notredame, Higgins, Heringa, JMB, 302 (205-217) 2000). The alignment was verified over the structures fit of SEQ ID NO: 1 model over the *A. thaliana* HPPD structure (PDB: 5YWG), as shown in FIG. 4 (The positions of secondary structural elements are shown on top of the alignment based on the structural elements of the HPPD of *A. thaliana* (PDB: 5YWG)). Motifs 1-9 of SEQ ID NO: 1 and/or 3 (set forth in SEQ ID NOs: 38-46 and SEQ ID NO: 47-54) are indicated by dashed-line boxes indicated by the numbered triangles (the motifs of At_HPPD, Zm_HPPD, Gm_HPPD, St_HPPD, Bn_HPPD, Ms_HPPD, Gh_HPPD, Bv_HPPD, Os_HPPD and AsHPPD are not indicated, but correspond to the motifs indicated for SEQ ID NO: 1).

Based on the 3D model nine structural motifs were recognized on SEQ ID NO: 1:

Motif 1: Glu137-Pro154 (set forth in SEQ ID NO: 38), located on helix-3 (H3) and sheet-B2 (B2).

Motif 2: Phe238-Ser254 (set forth in SEQ ID NO: 39), located on sheet-B3 (B3) and loop between sheet-B3 (B3) and sheet-C3 (C3).

Motif 3: Val318-Tyr337 (set forth in SEQ ID NO: 40), located on a short helix between helix-6 (H6) and helix-7 (H7), includes helix-7 (H7).

Motif 4: Gln352-Tyr365 (set forth in SEQ ID NO: 41), located between helix 8 (H8) and sheet C4 (C4), includes sheet B4 (B4).

Motif 5: Glu383-Gly394 (set forth in SEQ ID NO:42), located on sheet-D4 (D4) and includes loop between sheet-D4 (D4) and helix-9 (H9).

Motif 6: Ala167-Arg182 (set forth in SEQ ID NO:43), located on sheet-C2 (C2) and sheet-C3 (C3)

Motif 7: Glu224-Cys235 (set forth in SEQ ID NO:44), located on helix 7 (H7)

Motif 8: Gly392-Phe398 (set forth in SEQ ID NO:45), located on the loop between sheet-D4 (D4) and helix-9 (H9) and on helix-9 (H9)

Motif 9: Thr21-Ala26 (set forth in SEQ ID NO:46), located on unstructured region at the N-terminal.

Based on the 3D model nine structural motifs were recognized on SEQ ID NO:3:

Motif 1: Glu130-Pro147 (set forth in SEQ ID NO: 47), located on helix-3 (H3) and sheet-B2 (B2).

Motif 2: Phe239-Ser255 (set forth in SEQ ID NO: 48), located on sheet-B3 (B3) and loop between sheet-B3 (B3) and sheet-C3 (C3).

Motif 3: Val319-Lys338 (set forth in SEQ ID NO: 49), located on a short helix between helix-6 (H6) and helix-7 (H7), includes helix-7 (H7).

Motif 4: Lys351-Tyr364 (set forth in SEQ ID NO: 50), located between helix 8 (H8) and sheet C4 (C4), includes sheet B4 (B4).

Motif 5: Glu382-Gly393 (set forth in SEQ ID NO: 51), located on sheet-D4 (D4) and includes loop between sheet-D4 (D4) and helix-9 (H9).

Motif 6: Ala161-Arg176 (set forth in SEQ ID NO:52), located on sheet-C2 (C2) and sheet-C3 (C3)

Motif 7: Glu226-Val237 (set forth in SEQ ID NO:53), located on helix 7 (H7)

Motif 8: Gly392-Phe398 (set forth in SEQ ID NO:45), located on the loop between sheet-D4 (D4) and helix-9 (H9) and on helix-9 (H9)

Motif 9: Gln10-Pro15 (set forth in SEQ ID NO:54), located on unstructured region at the N-terminal.

Figure 5A:
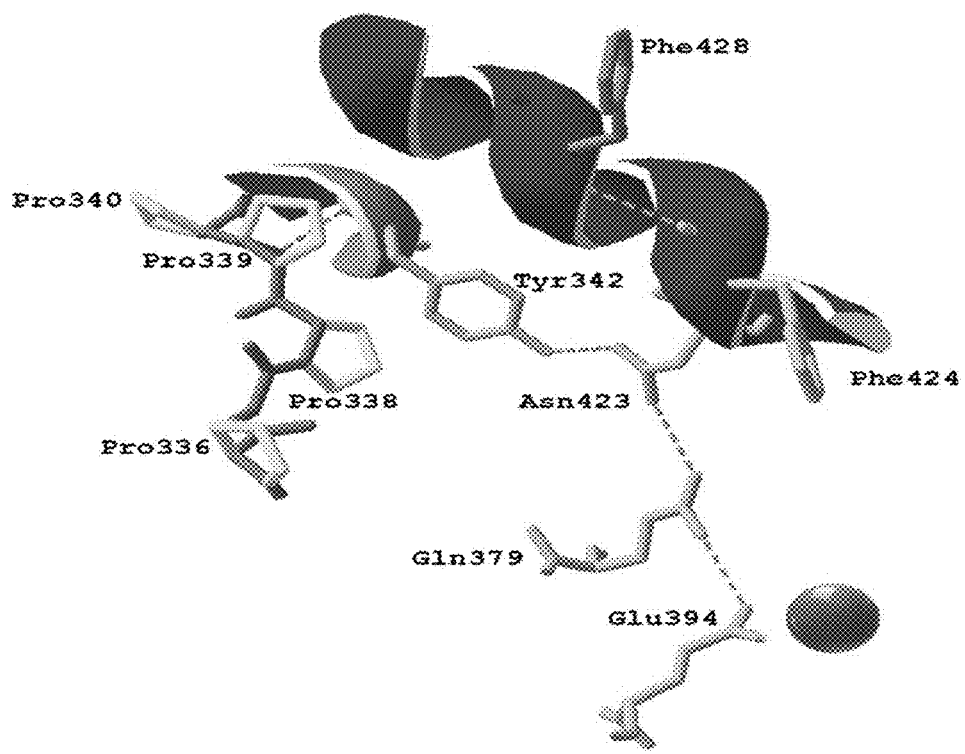
FIG. 5A shows a 3D model of molecular interactions between motifs 3, 5 and 8 in HPPD of *A. thaliana,*
Figure 5B:
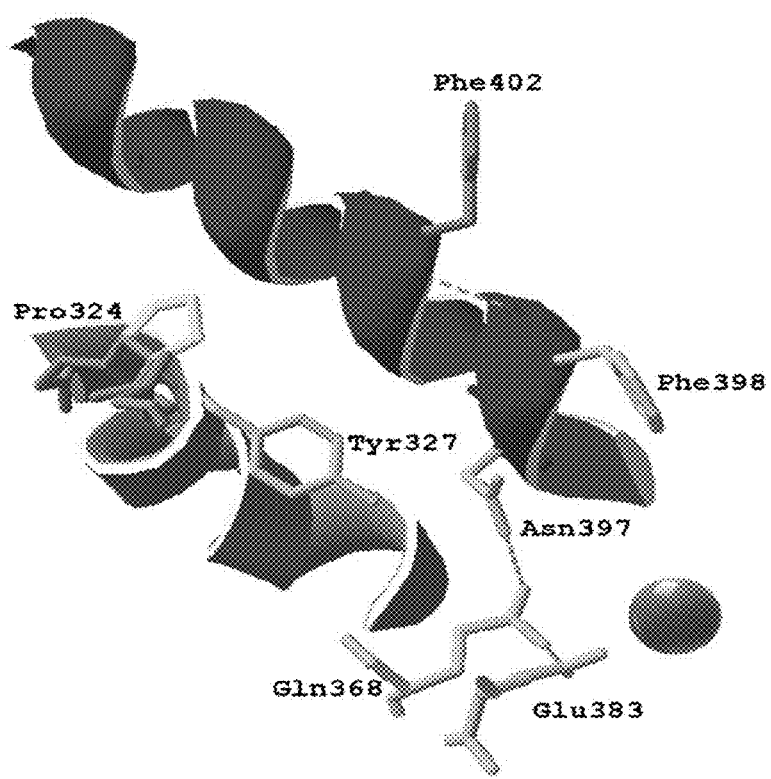
FIG. 5B shows the predicted 3D structure of the HPPD set forth in SEQ ID NO: 1, built based on the 3D structure of FIG. 5A.

The 3D model of HPPD of *A. thaliana* and of that built based on SEQ ID NO: 1, can be seen in FIG. 5A and FIG. 5B, respectively.

The active site metal ion (sphere) of the *A. thaliana* HPPD (FIG. 5A) is linked through three hydrogen bonds to helix 7 (H7) (originally in turquoise) constructing a hydrogen bond chain. Residues of the hydrogen bond chain are originally shown in orange. The bound inhibitor (originally in pink) is stabilized through π-stacking interaction with Phe424. The spatial location of Helix 7 is affected the hydrogen bond of Tyr342 and multiple Proline residues (originally in yellow).

As seen in FIG. 4 motif 3, forming helix 7 of SEQ ID NO: 1 (SEQ ID NO: 40), has less proline residues resulting in a longer helix with low rigidity, as seen in FIG. 5B, affecting weak interaction of Tyr327 with Asn397 in the predicted structure of SEQ ID NO:1, thus destabilizing the interaction with the inhibitor.

Figure 6A:
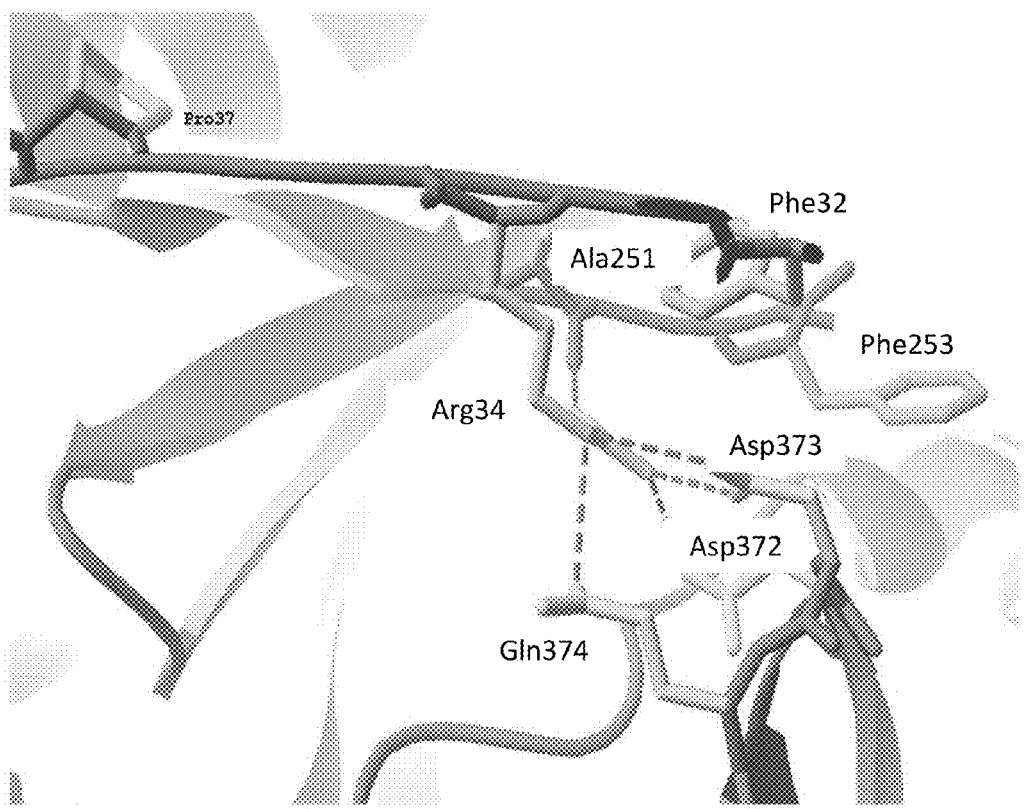
FIG. 6A shows a 3D model of molecular interactions between motifs 2, 4 and 9 in HPPD of *A. thaliana.*
Figure 6B:
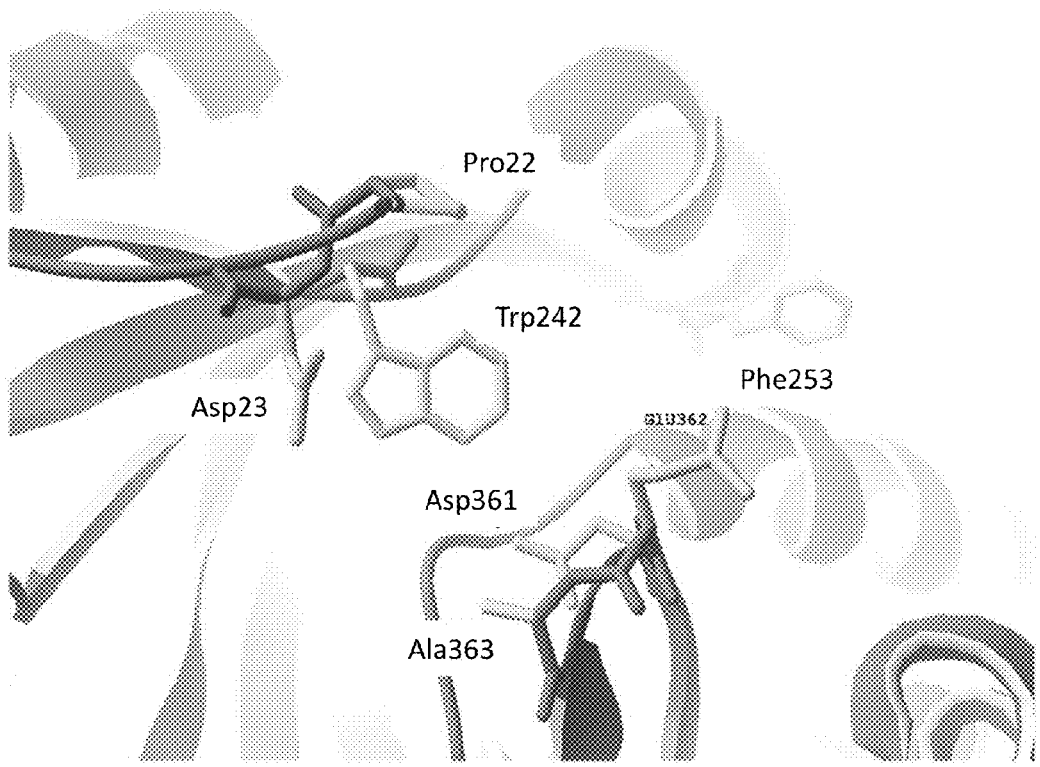
FIG. 6B shows the predicted 3D structure of part of the HPPD set forth in SEQ ID NO: 1.

As further seen from FIG. 6A and FIG. 6B, which show a 3D model of the spatial interactions of the structural elements formed by motifs 2 and 3 of *A. thaliana* and of that built based on SEQ ID NO: 1, respectively.

As seen from FIG. 6A, in the HPPD of *A. thaliana*, Asp372, Asp373 and Gln374 (motif 4 of At_HPPD in FIG. 3) forms hydrogen bonds with Arg34 of the N-terminal loop and Ala251 of motif 2 of At_HPPD. The location of the N-terminal loop is further stabilized through π-stacking interaction of Phe253 and Phe32.

As seen from FIG. 6B, in the predicted SEQ ID NO:1 structure, Trp242 of motif 2 (SEQ ID NO: 39) replaces Ala251, and forms a steric disturbance preventing hydrogen bonds between the motifs. Stabilizing through it-stacking was also not detected.

As further seen from FIG. 7A and FIG. 7B, which show the influence of the differences in motif 5 on the loop and helix 9 (H9) of HPPD of *A. thaliana* and of that built based on SEQ ID NO: 1 (SEQ ID NO: 24), respectively. As seen from FIG. 7A, motif 5 of At_HPPD forms a long loop tightened by an S—S bond formed by Cys401 and Cys416. In the predicted structure of the HPPD, shown in FIG. 7B, no such S—S bond is formed. Instead, a short loop (in orange) is formed and bound by hydrogen bonds to Asp359 and Gln368 of motif 4 (SEQ ID NO: 41) (secondary structure elements in gray). FIG. 7C, shows the superimposition of FIG. 7A and FIG. 7B.

Generation of cTP Chimeric HPPDs

The N-terminal sequence of the HPPD gene of the isolated *Trichoderma* fungus (SEQ ID NO: 1) was aligned over several plant N-terminal chloroplast transit peptide (cTP) sequences. Several chimeric constructs were designed with variations of deletions at the N-terminal region of SEQ ID NO: 1 (deletion of amino acids 1-22 (Δ22) (SEQ ID NO: 5) or of amino acids 1-38 (Δ38) (SEQ ID NO: 6)). The HPPD N-terminal peptides of *Arabidopsis thaliana* (amino acids 1-22 (SEQ ID NO: 104) or amino acids 1-49 (SEQ ID NO: 105) comprising the cTP of *Arabidopsis thaliana*) were added to SEQ ID NO: 1 enzyme as well as to the N-terminal truncated versions of SEQ ID NO: 1 (i.e. SEQ ID NO: 5 and SEQ ID NO: 6) as illustrated in FIG. 8.

HPPD-Activity Screen of cTP Chimeric HPPDs

Figure 8:
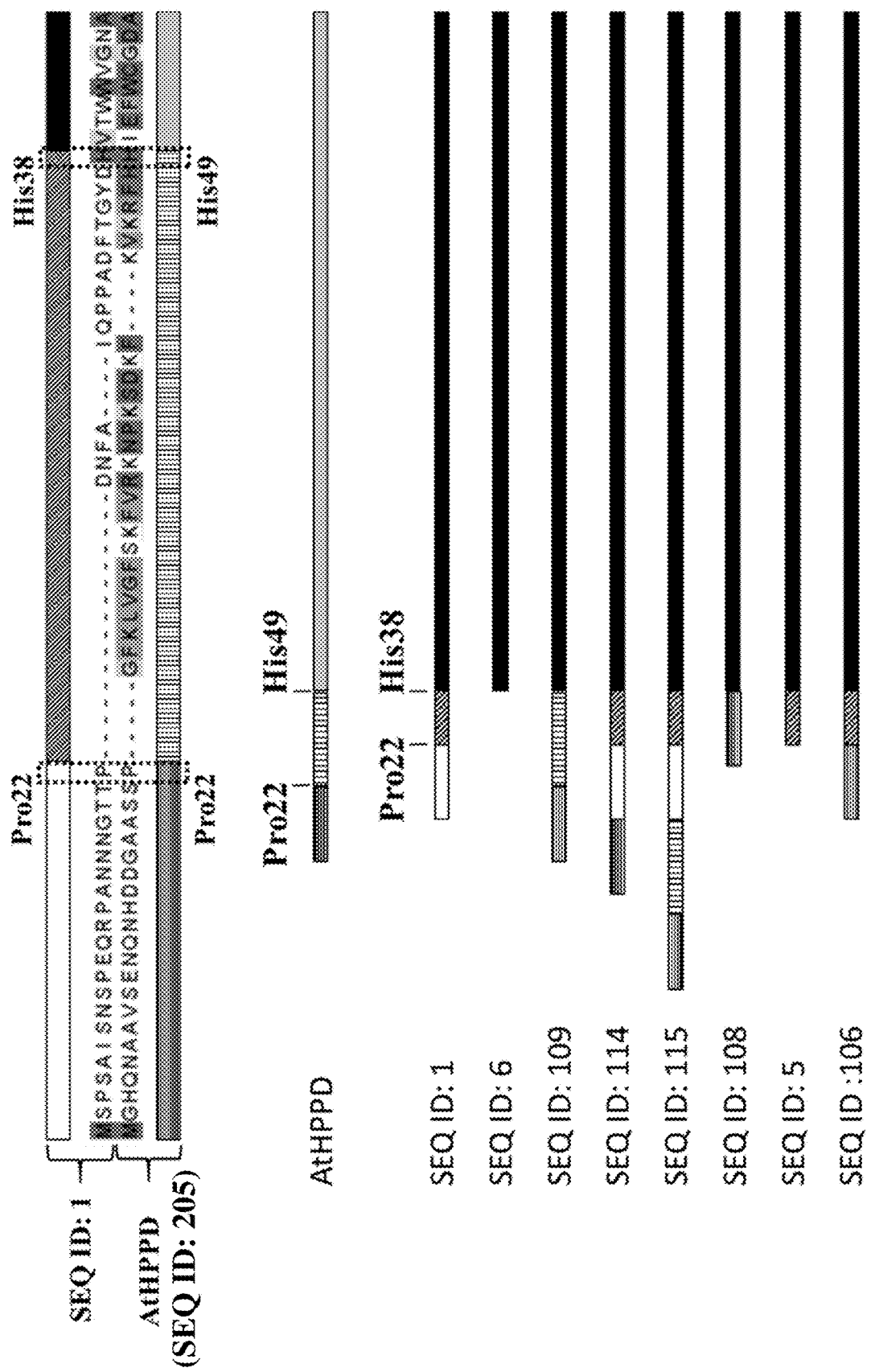
FIG. 8 schematically illustrates chimeric constructs of the N-terminal sequence of the herein disclosed fungal HPPD of truncated HPPD (deletion of amino acids 1-22 (Δ22) or of amino acids 1-38 (Δ38)), optionally fused to a plant derived N-terminal chloroplast transit peptide (cTP) sequence.

The cDNA sequences of the cTP chimeric HPPD set forth in FIG. 8 were amplified by PCR and cloned to a pET16 expression vector. *E. coli* BL21 (DE3) were transformed with the expression vector and monitored for HPPD activity using a colorimetric method as essentially explained in Rocaboy-Faquet. E. et al. (DOI: 10.1007/s00253-014-5793-5) with two minor modifications, namely: 1) The transformed bacteria were inoculated on an agar based medium instead of a liquid medium; 2) The screen was performed at 25° C. for 4 days.

The screen media was prepared with a concentration gradient of Laudis herbicide at the indicated concentrations of the active ingredient Tembotrione and the transformed bacteria were inoculated on the screening agar plates. HPPD activity was detected by a brown halo resulting from the HPPD-mediated conversion of p-hydroxyphenylpyruvate (HPP) into homogentisate (HGA), which later is oxidized to a melanin-like pigment. Tembotrione resistance of the transformed bacteria FIG. 9, was compared to that of plates inoculated with *E. coli* BL21 (DE3) transformed with *Arabidopsis thaliana* hppd cDNA (accession no. AF047834) FIG. 10.

Constructs SEQ ID NO: 6 (HPPD derived from *Trichoderma* fungus, truncated of amino acids 1-38 (Δ38)), SEQ ID NO: 114 (HPPD derived from *Trichoderma* fungus and with the addition of amino acids 1-22 of *Arabidopsis thaliana*) and SEQ ID NO: 108 (HPPD derived from *Trichoderma* fungus, truncated of amino acids 1-38 (Δ38) and with the addition of amino acids 1-22 of *Arabidopsis thaliana*) lost their HPPD enzymatic activity (results not shown).

Figure 9:
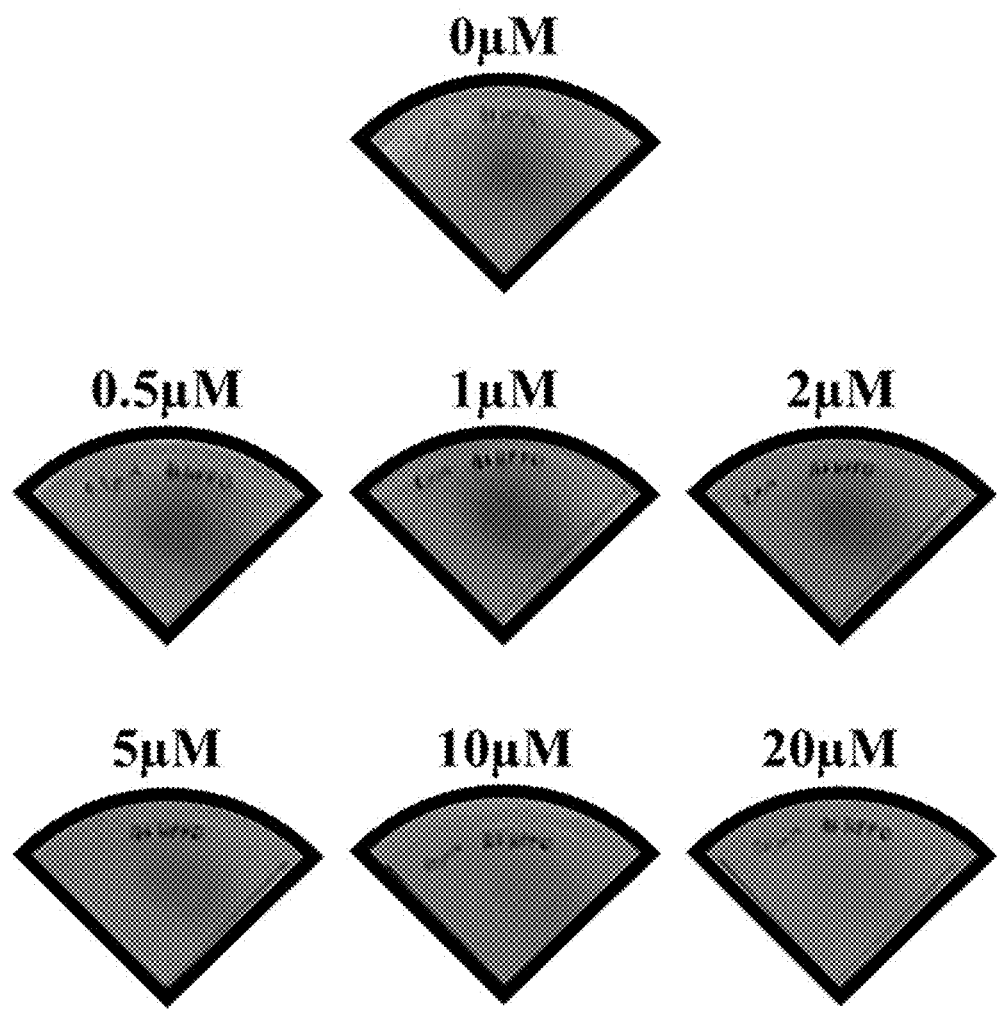
FIG. 9 shows illustrative images obtained from a HPPD-activity screen of *E. coli* BL21 (DE3) transformed with the chimeric *Trichoderma* spp derived HPPD shown in FIG. 8 in the absence or presence of increasing concentrations of tembotrione (Laudis) HPPD inhibitor. A brown halo is indicative of HPPD activity.
Figure 10:
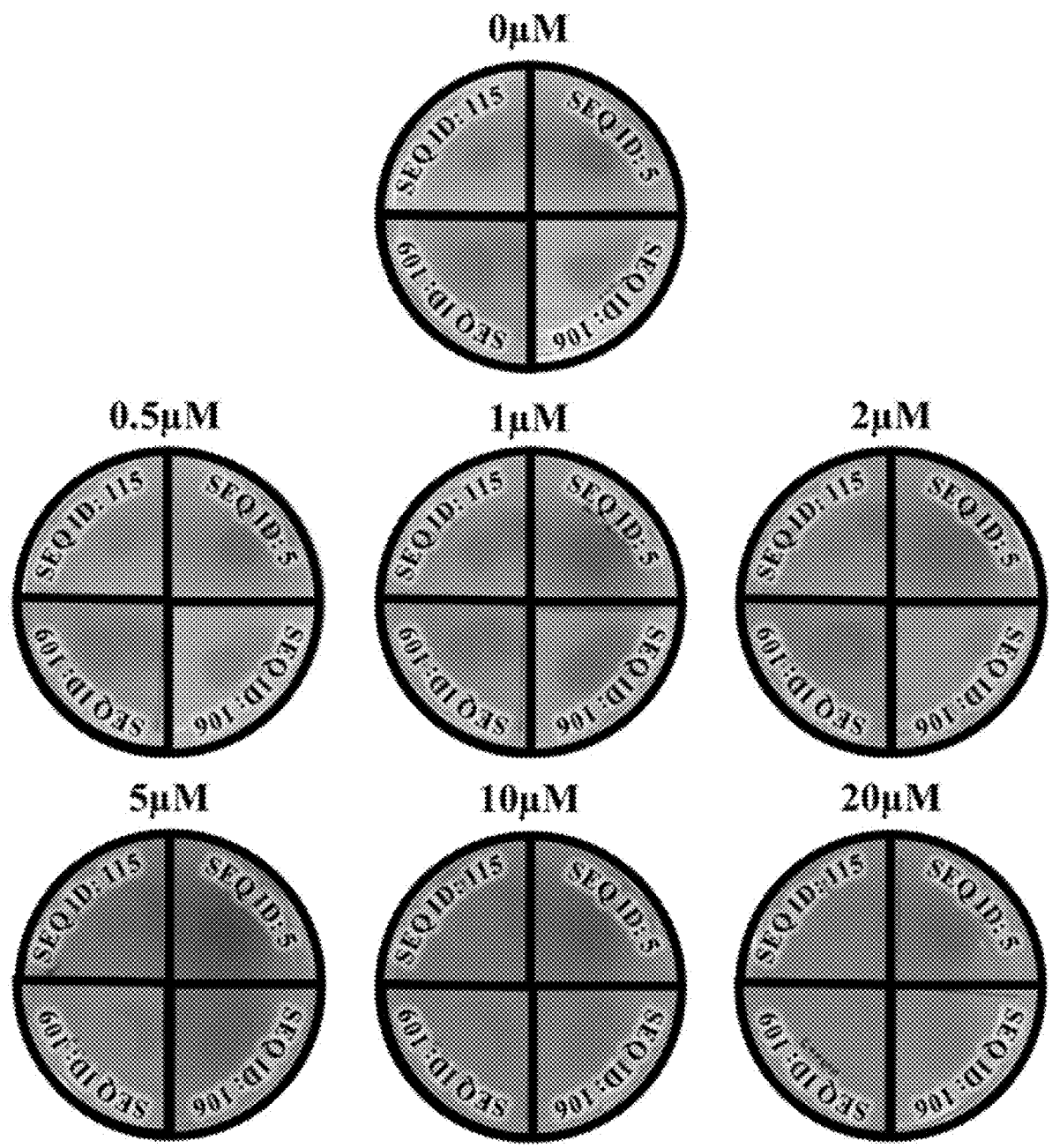
FIG. 10 shows illustrative images obtained from a HPPD-activity screen of *E. coli* BL21 (DE3) transformed with *Arabidopsis thaliana* HPPD cDNA (accession no. AF047834). A brown halo is indicative of HPPD activity.

As seen from FIG. 9, SEQ ID NO: 109 (HPPD derived from *Trichoderma* fungus, truncated of amino acids 1-38 (Δ38) and with the addition of amino acids 1-49 of *Arabidopsis thaliana*) and SEQ ID NO: 115 (HPPD derived from *Trichoderma* fungus and with the addition of amino acids 1-49 of *Arabidopsis thaliana*) were inhibited at tembotrione concentration above 2 μM and 5 μM, respectively, similarly to the endogenous AtHPPD of *Arabidopsis thaliana*—see FIG. 10.

However, surprisingly, the enzyme activity of SEQ ID NO: 5 (HPPD derived from *Trichoderma* fungus, truncated of amino acids 1-22 (Δ22)) and SEQ ID NO: 106 (HPPD derived from *Trichoderma* fungus in which amino acids 1-22 (Δ22) of the fungal HPPD were substituted with amino acids 1-22 of *Arabidopsis thaliana*) was maintained at concentrations as high as to 20 μM. This indicates that amino acids 1-22 (Δ22) of the fungal HPPD have minor if any importance to its enzymatic activity and may be substituted with a plant cTP to confer transport to chloroplasts.

HPPD-Activity Screen of Soy HPPD Mutants

The cDNA sequences of the below listed *G. max* HPPD (SEQ ID NO: 118) and *G. max* HPPD mutants were amplified by PCR and cloned to a pET16 expression vector. *E. coli* BL21 (DE3) were transformed with the expression vectors and monitored for HPPD activity using a colorimetric method as essentially explained in Rocaboy-Faquet. E. et al. (DOI: 10.1007/s00253-014-5793-5) with two minor modifications, namely: 1) The transformed bacteria were inoculated on an agar based medium instead of a liquid medium; 2) The screen was performed at 25° C. for 4 days, in the absence or presence of increasing concentrations of tembotrione (Laudis) HPPD inhibitor. A brown halo is indicative of HPPD activity GmHPPD SEQ ID NO: 118 (MPIPCNEIQAQAQAQAQPGFKLVGFKNFVRTNPKSDRFQVNRFHHIEFW CTDATNASRRFSWGLGMPIVAKSDLSTGNQIHASYLLRSGDLSFLFSAPYS PSLSAGSSAASSASIPSFDAATCLAFAAKHGFGVRAIALEVADAEAAFSAS VAKGAEPASPPVLVDDRTGFAEVRLYGDVVLRYVSYKDAAPQAPHADPS RWFLPGFEAAASSSSFPELDYGIRRLDHAVGNVPELAPAVRYLKGFSGFH EFAEFTAEDVGTSESGLNSVVLANNSETVLLPLNEPVYGTKRKSQIETYLE HNEGAGVQHLALVTHDIFTTLREMRKRSFLGGFEFMPSPPPTYYANLHNR AADVLTVDQIKQCEELGILVDRDDQGTLLQIFTKPVGDRPTIFIXIIQRIGC MVEDEEGKVYQKGACGGFGKGNFSELFKSIEEYEKTLEAKRTA), the native *G. max* HPPD (Accession number: ABQ96868)

GmHPPD.1=GmHPPD (SEQ ID NO: 118) mutated to substitute its motif 1 with motif 1 of SEQ ID NO: 1—i.e. to include amino acid sequences SEQ ID NO: 9-10 or 38;

GmHPPD.2=GmHPPD (SEQ ID NO: 118) mutated to substitute its motif 6.2 (SEQ ID NO: 68) first Y with motif 6.2 of SEQ ID NO: 1 (SEQ ID NO: 20)—i.e. to include the mutation Tyr185Phe to include SEQ ID NO: 157;

GmHPPD.4=GmHPPD (SEQ ID NO: 118) mutated to substitute its motif 2.1 (SEQ ID NO: 57) with motif 2.1 of SEQ ID NO: 1 (SEQ ID NO: 11)—i.e. to include the mutation Ala254Trp to include SEQ ID NO: 129.

Figure 11:
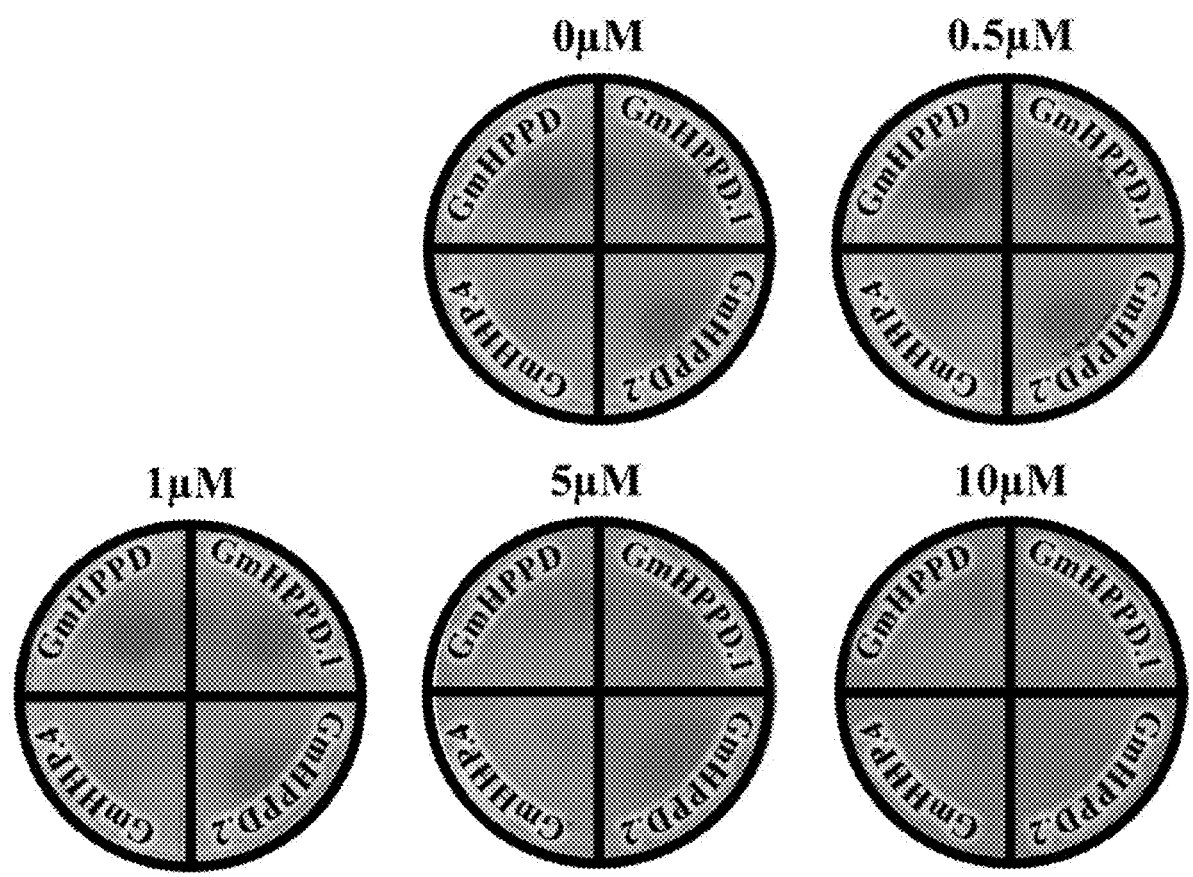
FIG. 11 shows illustrative images obtained from a HPPD-activity screen of *E. coli* BL21 (DE3) transformed with HPPD cDNA derived of mutated HPPD derived from *G. max* (GmHPPD=wt (Accession number: ABQ96868) set forth in SEQ ID NO: 118); GmHPPD.1=GmHPPD (SEQ ID NO: 118) mutated to substitute its motif 1 with motif 1 of SEQ ID NO: 1—i.e. to include amino acid sequences SEQ ID NO: 9-10 or 38; GmHPPD.2=GmHPPD (SEQ ID NO: 118) mutated to substitute its motif 6.2 (SEQ ID NO: 68) first Y with motif 6.2 of SEQ ID NO: 1 (SEQ ID NO: 20)—i.e. to include the mutation Tyr185Phe to include SEQ ID NO: 157; GmHPPD.4=GmHPPD (SEQ ID NO: 118) mutated to substitute its motif 2.1 (SEQ ID NO: 57) with motif 2.1 of SEQ ID NO: 1 (SEQ ID NO: 11)—i.e. to include the mutation Ala254Trp to include SEQ ID NO: 129 in the absence or presence of increasing concentrations of tembotrione (Laudis) HPPD inhibitor. A brown halo is indicative of HPPD activity.

As seen from FIG. 11, tembotrione effects the native soy HPPD (GmHPPD) activity already at concentrations above 11.1M, and only minor enzymatic activity was detected at inhibitor concentration of 5 μM, and essentially no enzymatic activity was observed at 10 μM tembotrione.

However, GmHPPD.1 and GmHPPD.2 showed significant activity at 5 μM tembotrione and some activity was still observed at 10 μM tembotrione.

These results indicate that soy HPPD having its motif 1 or motif's 6.2 first Tyr substituted with motif 1 and motif's 6.2 first Trp of *Trichoderma* HPPD maintained activity even at high concentrations of tembotrione.

In-Planta Screen of Soy HPPD Mutants

T1 generation transformed seeds of Camelina plants with the Soy HPPD (GmHPPD) mutated gene as compared to wt. Plant were treated with Laudis (Tembotrione) 0.075% three days post seeding. EGFP transformed plants were used as control. Images taken 19 days post treatment. The following were tested:

GmHPPD—SEQ ID NO: 118 the native *G. max* HPPD (Accession number: ABQ96868)

GmHPPD.1=GmHPPD (SEQ ID NO: 118) mutated to substitute its motif 1 with motif 1 of SEQ ID NO: 1—i.e. to include amino acid sequences set forth in SEQ ID NO: 9-10 or 38;

GmHPPD.2=GmHPPD (SEQ ID NO: 118) mutated to substitute its motif 6.2 (SEQ ID NO: 68) first Y with motif 6.2 of SEQ ID NO: 1 (SEQ ID NO: 20)—i.e. to include the mutation Tyr185Phe to include SEQ ID NO: 157;

GmHPPD.3=GmHPPD (SEQ ID NO: 118) mutated to substitute its motif 7.2 (SEQ ID NO: 70) first Y with motif 7.2 of SEQ ID NO: 1 (SEQ ID NO: 22)—i.e. to include the mutation Tyr243Phe;

GmHPPD.4=GmHPPD (SEQ ID NO: 118) mutated to substitute its motif 2.1 (SEQ ID NO: 57) with motif 2.1 of SEQ ID NO: 1 (SEQ ID NO: 11)—i.e. to include the mutation Ala254Trp to include SEQ ID NO: 129;

GmHPPD.5=GmHPPD (SEQ ID NO: 118) mutated to substitute its motif 3.1 with motif 3.1 of SEQ ID NO: 1—i.e. to include the replacement mutations 338-MPSPPP-343 to INVPG.

Figure 12:
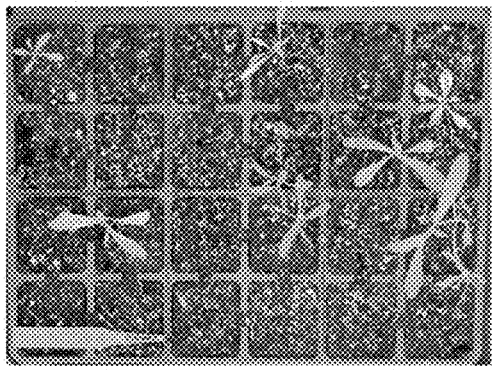
FIG. 12 shows T1 generation transformed seeds of Camelina plants with the Soy HPPD (GmHPPD) mutated gene as compared to wt and EGFP. HPPD derived from *G. max* (GmHPPD=wt (Accession number: ABQ96868) set forth in SEQ ID NO: 118); GmHPPD.1=GmHPPD (SEQ ID NO: 118) mutated to substitute its motif 1 with motif 1 of SEQ ID NO: 1—i.e. to include amino acid sequences SEQ ID NO: 9-10 or 38; GmHPPD.3=GmHPPD (SEQ ID NO: 118) mutated to substitute its motif 7.2 (SEQ ID NO: 70) first Y with motif 7.2 of SEQ ID NO: 1 (SEQ ID NO: 22)—i.e. to include the mutation Tyr243Phe to include SEQ ID NO: 154; GmHPPD.4=GmHPPD (SEQ ID NO: 118) mutated to substitute its motif 2.1 (SEQ ID NO: 57) with motif 2.1 of SEQ ID NO: 1 (SEQ ID NO: 11)—i.e. to include the mutation Ala254Trp to include SEQ ID NO: 129; GmHPPD.5=GmHPPD (SEQ ID NO: 118) mutated to substitute its motif 3.1 with motif 3.1 of SEQ ID NO: 1—i.e. to include the replacement mutations 338-MPSPPP-343 to INVPG to include amino acid sequences SEQ ID NO: 29.
Figure 12:
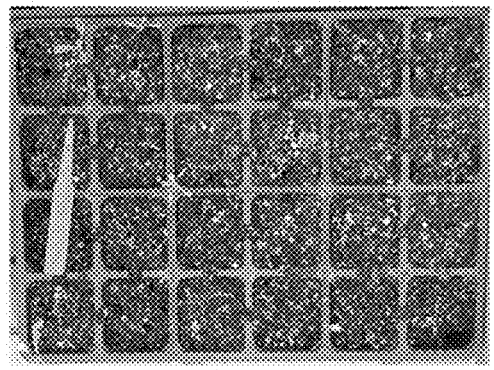
Figure 12:
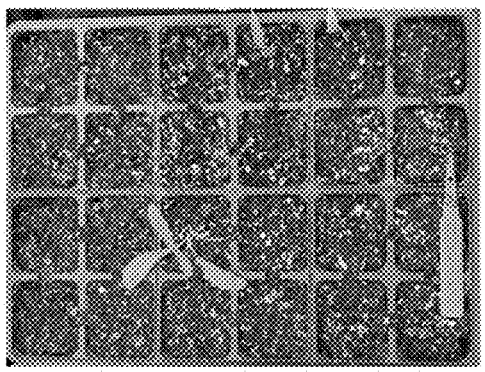
Figure 12:
Figure 12:
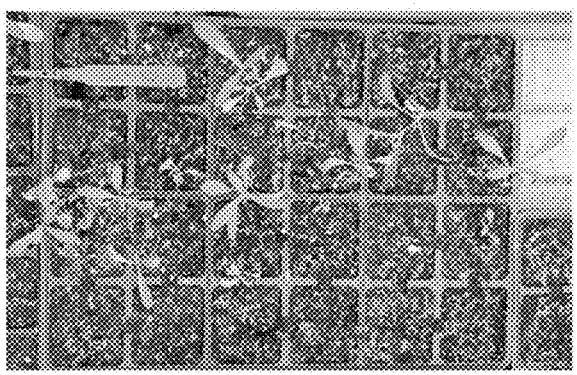
Figure 12:

As seen from FIG. 12, Control (EGFP), WT GmHPPD and GmHPPD.5 plants were highly damaged with the recognizable bleaching effects of the herbicide.

However, for GmHPPD.1 and GmHPPD.4 seeds, numerous tolerant plants were generated, clearly indicating that these HPPD mutants are herbicide resistant. The GmHPPD.3 mutant although producing a single plant only its recovery from the treatment was pronounced.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

What we claim is:

1. A method for selectively controlling weeds at a locus comprising a crop plant and said weeds, said method comprising applying to the locus one or more HPPD inhibitors, wherein the crop plant comprises a nucleic acid molecule encoding a polypeptide comprising any one of the amino acid sequences set forth in SEQ ID NO: 1, SEQ ID NO: 3, or SEQ ID NO: 5, wherein the crop plant is resistant to pre- and post-emergence application of said one or more HPPD inhibitors at a concentration sufficient to kill said weeds.

2. The method of claim 1, wherein the polypeptide further comprises a plant chloroplast transit peptide.

3. The method of claim 1, wherein the crop plant is selected from the group consisting of: soybean, cotton, maize, wheat, rice, barley, cowpea, chickpea, sorghum, beans, canola, alfalfa, flax, sunflower, safflower, millet, rye, sugarcane, sugar beet, cocoa, tea, *Brassica*, cotton, camelina, coffee, sweet potato, flax, peanut, clover; lettuce, tomato, cucurbits, cassava, potato, carrot, radish, pea, lentils, cabbage, cauliflower, broccoli, Brussels sprouts, peppers, pineapple, citrus, apples, pears, peaches, apricots, walnuts, avocado, banana, palm, eucalyptus, poplar, pine, coconut, orchids, petunia, carnations, roses, switchgrass, prairie grasses, indiangrass, and big bluestem grass.

4. The method of claim 3, wherein the crop plant is a soybean or cotton plant.

5. The method of claim 1, wherein the one or more HPPD inhibitors is selected from the group consisting of isoxaflutole, mesotrione, tembotrione, and topramezone.

* * * * *

SEQUENCE LISTING

<160> NUMBER OF SEQ ID NOS: 214

<210> SEQ ID NO 1
<211> LENGTH: 415
<212> TYPE: PRT
<213> ORGANISM: Trichoderma harzianum

```
<400> SEQUENCE: 1

Met Ser Pro Ser Ala Ile Ser Asn Ser Pro Glu Gln Arg Pro Ala Asn
1               5                   10                  15

Asn Asn Gly Thr Thr Pro Asp Asn Phe Ala Ile Gln Pro Pro Ala Asp
            20                  25                  30

Phe Thr Gly Tyr Asp His Val Thr Trp Trp Val Gly Asn Ala Lys Gln
            35                  40                  45

Ala Ala Ala Tyr Tyr Thr Thr Leu Phe Gly Phe Glu Thr Thr Ala Tyr
50                  55                  60

Arg Gly Leu Glu Thr Gly Ser Arg Tyr Phe Ala Ser Tyr Val Val Cys
65                  70                  75                  80

Asn Asn Gly Val Arg Phe Val Phe Thr Ser Pro Leu Arg Ser Glu Ala
            85                  90                  95

His Leu Pro Glu Asp Glu Thr Ile Ser Asp Ser Glu Arg Lys Leu Leu
            100                 105                 110

Lys Glu Ile His Ala His Leu Glu Arg His Gly Asp Ala Val Lys Asp
            115                 120                 125

Val Ala Phe Glu Val Asp Asn Val Glu Ala Val Tyr Asn Lys Ala Val
130                 135                 140

Ala Glu Gly Ala Ile Ala Val Gln Gly Pro Thr Ala Thr Lys Asp Asp
145                 150                 155                 160

His Gly Ser Val Thr Thr Ala Val Ile Cys Thr Tyr Gly Asp Thr Thr
                165                 170                 175

His Thr Leu Ile Asn Arg Arg Gly Tyr Thr Gly Pro Phe Leu Pro Gly
            180                 185                 190

Phe Arg Ala Gly Lys Glu Arg Thr Ser Ser Val Glu Met Pro Asn Val
            195                 200                 205

Pro Leu Ala Arg Ile Asp His Cys Val Gly Asn Gln Ser Trp Asn Glu
210                 215                 220

Met Val Ser Ala Cys Ala Phe Tyr Glu Gln Cys Leu Ser Phe His Arg
225                 230                 235                 240

Phe Trp Ser Val Asp Asp Ser Gln Ile Cys Thr Glu Phe Ser Ala Leu
                245                 250                 255

Asn Ser Ile Val Met Ala Ser Pro Asn Asn Leu Val Lys Met Pro Ile
            260                 265                 270

Asn Glu Pro Ala Pro Gly Lys Lys Lys Ser Gln Ile Glu Glu Tyr Val
            275                 280                 285

Ile Phe Asn Ser Gly Pro Gly Val Gln His Ile Ala Leu Leu Thr Pro
290                 295                 300

Asp Ile Ile Thr Ser Val Ser Ala Leu Arg Ala Arg Gly Val Glu Phe
305                 310                 315                 320

Ile Asn Val Pro Thr Thr Tyr Tyr Asp Thr Met Arg Gln Arg Leu Lys
                325                 330                 335

Thr Glu Lys Arg Asn Trp Gln Leu Lys Glu Asp Leu Thr Ile Gln
            340                 345                 350

Arg Leu Asn Ile Leu Ile Asp Tyr Asp Glu Ala Gly Tyr Leu Leu Gln
            355                 360                 365

Leu Phe Thr Lys Pro Leu Met Asp Arg Pro Thr Val Phe Ile Glu Ile
            370                 375                 380

Ile Gln Arg Asn Asn Phe Glu Gly Phe Ala Gly Asn Phe Lys Ser
385                 390                 395                 400

Leu Phe Glu Ala Ile Glu Arg Glu Gln Ala Glu Arg Gly Asn Leu
```

<210> SEQ ID NO 2
<211> LENGTH: 1248
<212> TYPE: DNA
<213> ORGANISM: Trichoderma harzianum

<400> SEQUENCE: 2

```
atgtccccgt ctgctatcag caactcccca gagcagcgac ctgcaaacaa caacggcacc      60
acccccgaca acttcgctat ccagcctccc gccgacttca ccggctatga ccacgtaacg     120
tggtgggttg caacgccaa gcaggcggcc gcttattaca ccaccctctt tgggttcgag     180
actacggcct atcgtggact cgagactgga agccgatact tcgcttccta tgtcgtctgc     240
aacaatggcg tccgcttcgt cttcacgtcg cctctgcgat cggaggctca cctccctgaa     300
gatgagacca tctctgattc tgagcggaag ctcctgaagg agattcacgc tcacctcgag     360
agacacggcg atgccgtcaa ggacgttgcc tttgaagttg acaacgtcga ggccgtatac     420
aacaaggccg tggctgaggg cgccatcgcc gtccaaggcc caaccgccac caaggatgat     480
cacggctccg tcaccacggc cgtcatctgc acctatggcg ataccaccca cactctcatc     540
aaccgccggg gctacacggg acctttcctg cccggcttcc gcgccggcaa ggagcgcacc     600
tcgtccgtgg agatgcccaa cgtgcccctt gcccgcatcg accactgcgt cggcaaccag     660
tcgtggaacg aaatggtctc ggcctgcgcc ttttacgagc agtgcctgtc cttccaccgt     720
ttctggtccg tcgacgactc ccagatctgc accgagttct cggccctcaa ctccatcgtc     780
atggcctcgc caacaacct cgtcaagatg cccatcaacg agcccgcccc gggcaagaag     840
aagtcccaga tcgaggagta cgtcatcttc aactccggcc cgggcgtcca gcacatcgcc     900
ctcctcaccc cggacatcat cacctccgtc tcggccctcc gcgcccgcgg cgtcgagttc     960
atcaacgtgc ccaccactta ctacgacacc atgcgccagc gcctcaagac ggagaagcgc    1020
aactggcagc tcaaggagga cctggacacc atccagcgcc tcaacatcct catcgactac    1080
gacgaggccg gctacctcct gcagctcttc accaagccgc tcatggaccg ccctaccgtc    1140
ttcattgaga ttatccagag aaacaacttt gagggcttcg cgccggcaa cttcaagagc    1200
ttgttcgagg ccattgagcg cgagcaggcc gagcgaggaa acctgtaa              1248
```

<210> SEQ ID NO 3
<211> LENGTH: 415
<212> TYPE: PRT
<213> ORGANISM: Unknown
<220> FEATURE:
<223> OTHER INFORMATION: Talaromyces spp.

<400> SEQUENCE: 3

```
Met Ala Pro Ser Ala Ile Ser Asp Leu Gln Ser Asp Asn Leu Pro Thr
1               5                   10                  15

Thr Gln Ser Ala Leu Ser Ser Tyr Arg Gly Tyr Asp His Val His Trp
            20                  25                  30

Tyr Val Gly Asn Ala Lys Gln Ala Ala Thr Phe Tyr Ile Thr Arg Met
        35                  40                  45

Gly Phe Ser Arg Val Ala Tyr Arg Gly Leu Glu Thr Gly Ser Arg Ser
    50                  55                  60

Val Cys Ser His Val Val Arg Asn Gly Gly Ile Thr Phe Val Leu Thr
65                  70                  75                  80

Ser Pro Leu Arg Ser Pro Tyr Asn Thr Glu Lys Leu Glu Arg Leu Leu
                85                  90                  95
```

Pro Ser Ala Glu Glu Arg Glu Tyr Leu Lys Glu Ile His Glu His Leu
                100                 105                 110

Ala Arg His Gly Asp Ala Val Lys Asp Val Ala Phe Glu Val Asp Ser
            115                 120                 125

Val Asp Asp Val Phe Ala Ala Val Gln Asn Gly Ala Val Ala Val
130                 135                 140

Ser Gln Pro Lys Thr Val Glu Asp Glu Asn Gly Gln Val Arg Val Ala
145                 150                 155                 160

Thr Ile Arg Thr Tyr Gly Asp Thr Thr His Thr Leu Ile Gln Arg Arg
                165                 170                 175

Gly Val Glu Lys Pro Tyr Ser Gly Val Phe Leu Pro Gly Tyr Arg Asp
            180                 185                 190

Glu Thr Thr Ser Gly Ser Ser Asp Pro Ile Thr Ala Phe Leu Pro Lys
        195                 200                 205

Val Asp Leu Arg Arg Ile Asp His Cys Val Gly Asn Gln Asp Trp Asp
210                 215                 220

Glu Met Glu Lys Val Cys Ala Tyr Tyr Glu Lys Val Leu Gly Phe His
225                 230                 235                 240

Arg Phe Arg Ser Val Asp Asp Lys Asp Ile Cys Thr Asp Tyr Ser Ala
                245                 250                 255

Leu Lys Ser Ile Val Met Ser Ser Pro Asn Asp Ile Val Lys Met Pro
            260                 265                 270

Ile Asn Glu Pro Ala His Gly Lys Lys Gln Ser Gln Ile Glu Glu Tyr
        275                 280                 285

Val Asp Phe Tyr Asp Gly Ala Gly Val Gln His Ile Ala Leu Leu Thr
290                 295                 300

Asp Asp Ile Ile Ser Ala Ile Thr Asn Leu Lys Ala Arg Gly Val Glu
305                 310                 315                 320

Phe Ile Lys Val Pro Pro Thr Tyr Tyr Asp Asn Met Trp Met Arg Leu
                325                 330                 335

Lys Lys Ala Gly Met Met Pro Lys Glu Ala Trp Glu Asp Ile Lys Lys
            340                 345                 350

Leu Asp Ile Leu Ile Asp Phe Asp Glu Gly Gly Tyr Leu Leu Gln Leu
        355                 360                 365

Phe Thr Lys His Leu Met Asp Arg Pro Thr Val Phe Ile Glu Ile Ile
370                 375                 380

Gln Arg Asn Asn Phe Ser Gly Phe Gly Ala Gly Asn Phe Lys Ser Leu
385                 390                 395                 400

Phe Glu Ala Ile Glu Arg Glu Gln Ala Leu Arg Gly Asn Leu Ile
                405                 410                 415

<210> SEQ ID NO 4
<211> LENGTH: 1248
<212> TYPE: DNA
<213> ORGANISM: Unknown
<220> FEATURE:
<223> OTHER INFORMATION: Talaromyces spp.

<400> SEQUENCE: 4
atggcaccat cagccatctc agacctccaa tccgacaacc tacccacaac ccaatccgcc      60
ctctcctcct accgcggcta cgaccatgta cactggtacg tcggcaacgc caaacaggcc     120
gcaaccttct acataacgcg catgggattt tctcgtgtcg cctaccgcgg tctcgaaacc     180
ggctctcgca gcgtctgctc acacgtcgtg cgcaacggcg gtataacttt tgtcctgacc     240

-continued

```
tcgccgcttc gatcacccta caacactgag aaactcgagc gcctacttcc cagtgctgaa    300
gagcgggagt atttgaaaga gattcatgag catttggcac gacatggtga tgcagtcaaa    360
gacgtcgcgt ttgaggtcga ttccgtcgat gatgtgttcg ctgctgcggt gcagaatggc    420
gccgttgcgg tctcgcaacc caagaccgtg gaggatgaga atggtcaagt gagggttgcc    480
acgattcgga cgtatgggga tacgacgcat actttgattc agcgacgggg ggtcgaaaag    540
ccgtattcgg gcgttttctt gccagggtac agggatgaga cgacttctgg tagcagtgat    600
cctatcacgg cgttcctgcc caaggttgat ttgaggagga ttgatcattg tgtggggaat    660
caggattggg atgaaatgga aaggtctgc gcgtactacg aaaaagtcct cggattccac    720
cgtttccggt ccgtagacga caaagacatc tgcacagact actccgccct gaaatcaatc    780
gtcatgtcct cgcccaacga cattgtcaaa atgcccatca acgaacccgc ccacggcaaa    840
aaacaatccc aaatcgaaga atacgtcgac ttttacgacg gcgccggcgt ccaacacatt    900
gccctgctga cagacgacat aatcagcgcg atcacgaatc tcaaagcgcg cggggtggag    960
tttatcaaag tgccgcctac gtattacgat aacatgtgga tgcggctgaa gaaagcgggc   1020
atgatgccca aggaggcgtg ggaggatatt aagaagttgg atattctgat cgattttgat   1080
gagggagggt atttgttgca gctcttcaca aagcatctca tggatcggcc gactgttttc   1140
attgagatta ttcagcgcaa taacttctca ggctttggtg ctggtaattt caagtcgctg   1200
ttcgaagcta ttgaacgtga gcaggctctt agaggaaacc tgatctga                 1248
```

<210> SEQ ID NO 5
<211> LENGTH: 393
<212> TYPE: PRT
<213> ORGANISM: Trichoderma harzianum

<400> SEQUENCE: 5

```
Asp Asn Phe Ala Ile Gln Pro Pro Ala Asp Phe Thr Gly Tyr Asp His
1               5                   10                  15

Val Thr Trp Trp Val Gly Asn Ala Lys Gln Ala Ala Tyr Tyr Thr
            20                  25                  30

Thr Leu Phe Gly Phe Glu Thr Thr Ala Tyr Arg Gly Leu Glu Thr Gly
        35                  40                  45

Ser Arg Tyr Phe Ala Ser Tyr Val Val Cys Asn Asn Gly Val Arg Phe
    50                  55                  60

Val Phe Thr Ser Pro Leu Arg Ser Glu Ala His Leu Pro Glu Asp Glu
65                  70                  75                  80

Thr Ile Ser Asp Ser Glu Arg Lys Leu Leu Lys Glu Ile His Ala His
                85                  90                  95

Leu Glu Arg His Gly Asp Ala Val Lys Asp Val Ala Phe Glu Val Asp
            100                 105                 110

Asn Val Glu Ala Val Tyr Asn Lys Ala Val Ala Glu Gly Ala Ile Ala
        115                 120                 125

Val Gln Gly Pro Thr Ala Thr Lys Asp Asp His Gly Ser Val Thr Thr
    130                 135                 140

Ala Val Ile Cys Thr Tyr Gly Asp Thr Thr His Thr Leu Ile Asn Arg
145                 150                 155                 160

Arg Gly Tyr Thr Gly Pro Phe Leu Pro Gly Phe Arg Ala Gly Lys Glu
                165                 170                 175

Arg Thr Ser Ser Val Glu Met Pro Asn Val Pro Leu Ala Arg Ile Asp
            180                 185                 190

His Cys Val Gly Asn Gln Ser Trp Asn Glu Met Val Ser Ala Cys Ala
```

```
                 195                 200                 205

Phe Tyr Glu Gln Cys Leu Ser Phe His Arg Phe Trp Ser Val Asp Asp
210                 215                 220

Ser Gln Ile Cys Thr Glu Phe Ser Ala Leu Asn Ser Ile Val Met Ala
225                 230                 235                 240

Ser Pro Asn Asn Leu Val Lys Met Pro Ile Asn Glu Pro Ala Pro Gly
                245                 250                 255

Lys Lys Lys Ser Gln Ile Glu Glu Tyr Val Ile Phe Asn Ser Gly Pro
                260                 265                 270

Gly Val Gln His Ile Ala Leu Leu Thr Pro Asp Ile Ile Thr Ser Val
                275                 280                 285

Ser Ala Leu Arg Ala Arg Gly Val Glu Phe Ile Asn Val Pro Thr Thr
290                 295                 300

Tyr Tyr Asp Thr Met Arg Gln Arg Leu Lys Thr Glu Lys Arg Asn Trp
305                 310                 315                 320

Gln Leu Lys Glu Asp Leu Asp Thr Ile Gln Arg Leu Asn Ile Leu Ile
                325                 330                 335

Asp Tyr Asp Glu Ala Gly Tyr Leu Leu Gln Leu Phe Thr Lys Pro Leu
                340                 345                 350

Met Asp Arg Pro Thr Val Phe Ile Glu Ile Gln Arg Asn Asn Phe
                355                 360                 365

Glu Gly Phe Gly Ala Gly Asn Phe Lys Ser Leu Phe Glu Ala Ile Glu
370                 375                 380

Arg Glu Gln Ala Glu Arg Gly Asn Leu
385                 390

<210> SEQ ID NO 6
<211> LENGTH: 377
<212> TYPE: PRT
<213> ORGANISM: Trichoderma harzianum

<400> SEQUENCE: 6

Val Thr Trp Trp Val Gly Asn Ala Lys Gln Ala Ala Ala Tyr Tyr Thr
1               5                   10                  15

Thr Leu Phe Gly Phe Glu Thr Thr Ala Tyr Arg Gly Leu Glu Thr Gly
                20                  25                  30

Ser Arg Tyr Phe Ala Ser Tyr Val Val Cys Asn Asn Gly Val Arg Phe
            35                  40                  45

Val Phe Thr Ser Pro Leu Arg Ser Glu Ala His Leu Pro Glu Asp Glu
50                  55                  60

Thr Ile Ser Asp Ser Glu Arg Lys Leu Leu Lys Glu Ile His Ala His
65                  70                  75                  80

Leu Glu Arg His Gly Asp Ala Val Lys Asp Val Ala Phe Glu Val Asp
                85                  90                  95

Asn Val Glu Ala Val Tyr Asn Lys Ala Val Ala Glu Gly Ala Ile Ala
                100                 105                 110

Val Gln Gly Pro Thr Ala Thr Lys Asp Asp His Gly Ser Val Thr Thr
            115                 120                 125

Ala Val Ile Cys Thr Tyr Gly Asp Thr Thr His Thr Leu Ile Asn Arg
130                 135                 140

Arg Gly Tyr Thr Gly Pro Phe Leu Pro Gly Phe Arg Ala Gly Lys Glu
145                 150                 155                 160

Arg Thr Ser Ser Val Glu Met Pro Asn Val Pro Leu Ala Arg Ile Asp
                165                 170                 175
```

```
His Cys Val Gly Asn Gln Ser Trp Asn Glu Met Val Ser Ala Cys Ala
            180                 185                 190

Phe Tyr Glu Gln Cys Leu Ser Phe His Arg Phe Trp Ser Val Asp Asp
        195                 200                 205

Ser Gln Ile Cys Thr Glu Phe Ser Ala Leu Asn Ser Ile Val Met Ala
    210                 215                 220

Ser Pro Asn Asn Leu Val Lys Met Pro Ile Asn Glu Pro Ala Pro Gly
225                 230                 235                 240

Lys Lys Lys Ser Gln Ile Glu Glu Tyr Val Ile Phe Asn Ser Gly Pro
                245                 250                 255

Gly Val Gln His Ile Ala Leu Leu Thr Pro Asp Ile Ile Thr Ser Val
            260                 265                 270

Ser Ala Leu Arg Ala Arg Gly Val Glu Phe Ile Asn Val Pro Thr Thr
        275                 280                 285

Tyr Tyr Asp Thr Met Arg Gln Arg Leu Lys Thr Glu Lys Arg Asn Trp
    290                 295                 300

Gln Leu Lys Glu Asp Leu Asp Thr Ile Gln Arg Leu Asn Ile Leu Ile
305                 310                 315                 320

Asp Tyr Asp Glu Ala Gly Tyr Leu Leu Gln Leu Phe Thr Lys Pro Leu
                325                 330                 335

Met Asp Arg Pro Thr Val Phe Ile Glu Ile Ile Gln Arg Asn Asn Phe
            340                 345                 350

Glu Gly Phe Gly Ala Gly Asn Phe Lys Ser Leu Phe Glu Ala Ile Glu
        355                 360                 365

Arg Glu Gln Ala Glu Arg Gly Asn Leu
    370                 375

<210> SEQ ID NO 7
<211> LENGTH: 401
<212> TYPE: PRT
<213> ORGANISM: Unknown
<220> FEATURE:
<223> OTHER INFORMATION: Talaromyces spp. truncated

<400> SEQUENCE: 7

Pro Thr Thr Gln Ser Ala Leu Ser Ser Tyr Arg Gly Tyr Asp His Val
1               5                   10                  15

His Trp Tyr Val Gly Asn Ala Lys Gln Ala Ala Thr Phe Tyr Ile Thr
            20                  25                  30

Arg Met Gly Phe Ser Arg Val Ala Tyr Arg Gly Leu Glu Thr Gly Ser
        35                  40                  45

Arg Ser Val Cys Ser His Val Val Arg Asn Gly Ile Thr Phe Val
    50                  55                  60

Leu Thr Ser Pro Leu Arg Ser Pro Tyr Asn Thr Glu Lys Leu Glu Arg
65                  70                  75                  80

Leu Leu Pro Ser Ala Glu Glu Arg Glu Tyr Leu Lys Glu Ile His Glu
                85                  90                  95

His Leu Ala Arg His Gly Asp Ala Val Lys Asp Val Ala Phe Glu Val
            100                 105                 110

Asp Ser Val Asp Asp Val Phe Ala Ala Ala Val Gln Asn Gly Ala Val
        115                 120                 125

Ala Val Ser Gln Pro Lys Thr Val Glu Asp Glu Asn Gly Gln Val Arg
    130                 135                 140

Val Ala Thr Ile Arg Thr Tyr Gly Asp Thr Thr His Thr Leu Ile Gln
145                 150                 155                 160
```

Arg Arg Gly Val Glu Lys Pro Tyr Ser Gly Val Phe Leu Pro Gly Tyr
                165                 170                 175

Arg Asp Glu Thr Thr Ser Gly Ser Ser Asp Pro Ile Thr Ala Phe Leu
            180                 185                 190

Pro Lys Val Asp Leu Arg Arg Ile Asp His Cys Val Gly Asn Gln Asp
        195                 200                 205

Trp Asp Glu Met Glu Lys Val Cys Ala Tyr Tyr Glu Lys Val Leu Gly
210                 215                 220

Phe His Arg Phe Arg Ser Val Asp Asp Lys Ile Cys Thr Asp Tyr
225                 230                 235                 240

Ser Ala Leu Lys Ser Ile Val Met Ser Ser Pro Asn Asp Ile Val Lys
            245                 250                 255

Met Pro Ile Asn Glu Pro Ala His Gly Lys Lys Gln Ser Gln Ile Glu
        260                 265                 270

Glu Tyr Val Asp Phe Tyr Asp Gly Ala Gly Val Gln His Ile Ala Leu
    275                 280                 285

Leu Thr Asp Asp Ile Ile Ser Ala Ile Thr Asn Leu Lys Ala Arg Gly
290                 295                 300

Val Glu Phe Ile Lys Val Pro Pro Thr Tyr Tyr Asp Asn Met Trp Met
305                 310                 315                 320

Arg Leu Lys Lys Ala Gly Met Met Pro Lys Glu Ala Trp Glu Asp Ile
            325                 330                 335

Lys Lys Leu Asp Ile Leu Ile Asp Phe Asp Glu Gly Tyr Leu Leu
        340                 345                 350

Gln Leu Phe Thr Lys His Leu Met Asp Arg Pro Thr Val Phe Ile Glu
    355                 360                 365

Ile Ile Gln Arg Asn Asn Phe Ser Gly Phe Gly Ala Gly Asn Phe Lys
370                 375                 380

Ser Leu Phe Glu Ala Ile Glu Arg Glu Gln Ala Leu Arg Gly Asn Leu
385                 390                 395                 400

Ile

<210> SEQ ID NO 8
<211> LENGTH: 386
<212> TYPE: PRT
<213> ORGANISM: Unknown
<220> FEATURE:
<223> OTHER INFORMATION: Talaromyces spp. truncated

<400> SEQUENCE: 8

Val His Trp Tyr Val Gly Asn Ala Lys Gln Ala Thr Phe Tyr Ile
1               5                   10                  15

Thr Arg Met Gly Phe Ser Arg Val Ala Tyr Arg Gly Leu Glu Thr Gly
            20                  25                  30

Ser Arg Ser Val Cys Ser His Val Val Arg Asn Gly Ile Thr Phe
        35                  40                  45

Val Leu Thr Ser Pro Leu Arg Ser Pro Tyr Asn Thr Glu Lys Leu Glu
    50                  55                  60

Arg Leu Leu Pro Ser Ala Glu Glu Arg Glu Tyr Leu Lys Glu Ile His
65                  70                  75                  80

Glu His Leu Ala Arg His Gly Asp Ala Val Lys Asp Val Ala Phe Glu
                85                  90                  95

Val Asp Ser Val Asp Asp Val Phe Ala Ala Val Gln Asn Gly Ala
            100                 105                 110

Val Ala Val Ser Gln Pro Lys Thr Val Glu Asp Glu Asn Gly Gln Val

```
            115                 120                 125
Arg Val Ala Thr Ile Arg Thr Tyr Gly Asp Thr Thr His Thr Leu Ile
    130                 135                 140

Gln Arg Arg Gly Val Glu Lys Pro Tyr Ser Gly Val Phe Leu Pro Gly
145                 150                 155                 160

Tyr Arg Asp Glu Thr Thr Ser Gly Ser Ser Asp Pro Ile Thr Ala Phe
                165                 170                 175

Leu Pro Lys Val Asp Leu Arg Arg Ile Asp His Cys Val Gly Asn Gln
            180                 185                 190

Asp Trp Asp Glu Met Glu Lys Val Cys Ala Tyr Tyr Glu Lys Val Leu
        195                 200                 205

Gly Phe His Arg Phe Arg Ser Val Asp Asp Lys Asp Ile Cys Thr Asp
    210                 215                 220

Tyr Ser Ala Leu Lys Ser Ile Val Met Ser Ser Pro Asn Asp Ile Val
225                 230                 235                 240

Lys Met Pro Ile Asn Glu Pro Ala His Gly Lys Lys Gln Ser Gln Ile
                245                 250                 255

Glu Glu Tyr Val Asp Phe Tyr Asp Gly Ala Gly Val Gln His Ile Ala
            260                 265                 270

Leu Leu Thr Asp Asp Ile Ile Ser Ala Ile Thr Asn Leu Lys Ala Arg
        275                 280                 285

Gly Val Glu Phe Ile Lys Val Pro Pro Thr Tyr Tyr Asp Asn Met Trp
    290                 295                 300

Met Arg Leu Lys Lys Ala Gly Met Met Pro Lys Glu Ala Trp Glu Asp
305                 310                 315                 320

Ile Lys Lys Leu Asp Ile Leu Asp Phe Asp Glu Gly Gly Tyr Leu
                325                 330                 335

Leu Gln Leu Phe Thr Lys His Leu Met Asp Arg Pro Thr Val Phe Ile
            340                 345                 350

Glu Ile Ile Gln Arg Asn Asn Phe Ser Gly Phe Gly Ala Gly Asn Phe
        355                 360                 365

Lys Ser Leu Phe Glu Ala Ile Glu Arg Glu Gln Ala Leu Arg Gly Asn
    370                 375                 380

Leu Ile
385

<210> SEQ ID NO 9
<211> LENGTH: 12
<212> TYPE: PRT
<213> ORGANISM: Trichoderma harzianum

<400> SEQUENCE: 9

Glu Ala Val Tyr Asn Lys Ala Val Ala Glu Gly Ala
1               5                   10

<210> SEQ ID NO 10
<211> LENGTH: 11
<212> TYPE: PRT
<213> ORGANISM: Trichoderma harzianum

<400> SEQUENCE: 10

Val Ala Glu Gly Ala Ile Ala Val Gln Gly Pro
1               5                   10

<210> SEQ ID NO 11
<211> LENGTH: 9
<212> TYPE: PRT
```

<213> ORGANISM: Trichoderma harzianum

<400> SEQUENCE: 11

Phe His Arg Phe Trp Ser Val Asp Asp
1               5

<210> SEQ ID NO 12
<211> LENGTH: 10
<212> TYPE: PRT
<213> ORGANISM: Trichoderma harzianum

<400> SEQUENCE: 12

Asp Asp Ser Gln Ile Cys Thr Glu Phe Ser
1               5                   10

<210> SEQ ID NO 13
<211> LENGTH: 11
<212> TYPE: PRT
<213> ORGANISM: Trichoderma harzianum

<400> SEQUENCE: 13

Val Glu Phe Ile Asn Val Pro Thr Thr Tyr Tyr
1               5                   10

<210> SEQ ID NO 14
<211> LENGTH: 12
<212> TYPE: PRT
<213> ORGANISM: Trichoderma harzianum

<400> SEQUENCE: 14

Thr Tyr Tyr Asp Thr Met Arg Gln Arg Leu Lys Thr
1               5                   10

<210> SEQ ID NO 15
<211> LENGTH: 8
<212> TYPE: PRT
<213> ORGANISM: Trichoderma harzianum

<400> SEQUENCE: 15

Gln Arg Leu Asn Ile Leu Ile Asp
1               5

<210> SEQ ID NO 16
<211> LENGTH: 8
<212> TYPE: PRT
<213> ORGANISM: Trichoderma harzianum

<400> SEQUENCE: 16

Ile Asp Tyr Asp Glu Ala Gly Tyr
1               5

<210> SEQ ID NO 17
<211> LENGTH: 8
<212> TYPE: PRT
<213> ORGANISM: Trichoderma harzianum

<400> SEQUENCE: 17

Glu Ile Ile Gln Arg Asn Asn Phe
1               5

<210> SEQ ID NO 18
<211> LENGTH: 7
<212> TYPE: PRT
<213> ORGANISM: Trichoderma harzianum

```
<400> SEQUENCE: 18

Asn Asn Phe Glu Gly Phe Gly
1               5

<210> SEQ ID NO 19
<211> LENGTH: 9
<212> TYPE: PRT
<213> ORGANISM: Trichoderma harzianum

<400> SEQUENCE: 19

Ala Val Ile Cys Thr Tyr Gly Asp Thr
1               5

<210> SEQ ID NO 20
<211> LENGTH: 9
<212> TYPE: PRT
<213> ORGANISM: Trichoderma harzianum

<400> SEQUENCE: 20

Asp Thr Thr His Thr Leu Ile Asn Arg
1               5

<210> SEQ ID NO 21
<211> LENGTH: 7
<212> TYPE: PRT
<213> ORGANISM: Trichoderma harzianum

<400> SEQUENCE: 21

Glu Met Val Ser Ala Cys Ala
1               5

<210> SEQ ID NO 22
<211> LENGTH: 7
<212> TYPE: PRT
<213> ORGANISM: Trichoderma harzianum

<400> SEQUENCE: 22

Cys Ala Phe Tyr Glu Gln Cys
1               5

<210> SEQ ID NO 23
<211> LENGTH: 7
<212> TYPE: PRT
<213> ORGANISM: Trichoderma harzianum

<400> SEQUENCE: 23

Gly Phe Gly Ala Gly Asn Phe
1               5

<210> SEQ ID NO 24
<211> LENGTH: 6
<212> TYPE: PRT
<213> ORGANISM: Trichoderma harzianum

<400> SEQUENCE: 24

Thr Pro Asp Asn Phe Ala
1               5

<210> SEQ ID NO 25
<211> LENGTH: 12
<212> TYPE: PRT
<213> ORGANISM: Unknown
<220> FEATURE:
<223> OTHER INFORMATION: Talaromyces spp
```

```
<400> SEQUENCE: 25

Asp Asp Val Phe Ala Ala Ala Val Gln Asn Gly Ala
1               5                   10

<210> SEQ ID NO 26
<211> LENGTH: 11
<212> TYPE: PRT
<213> ORGANISM: Unknown
<220> FEATURE:
<223> OTHER INFORMATION: Talaromyces spp

<400> SEQUENCE: 26

Val Gln Asn Gly Ala Val Ala Val Ser Gln Pro
1               5                   10

<210> SEQ ID NO 27
<211> LENGTH: 9
<212> TYPE: PRT
<213> ORGANISM: Unknown
<220> FEATURE:
<223> OTHER INFORMATION: Talaromyces spp

<400> SEQUENCE: 27

Phe His Arg Phe Arg Ser Val Asp Asp
1               5

<210> SEQ ID NO 28
<211> LENGTH: 10
<212> TYPE: PRT
<213> ORGANISM: Unknown
<220> FEATURE:
<223> OTHER INFORMATION: Talaromyces spp

<400> SEQUENCE: 28

Asp Asp Lys Asp Ile Cys Thr Asp Tyr Ser
1               5                   10

<210> SEQ ID NO 29
<211> LENGTH: 11
<212> TYPE: PRT
<213> ORGANISM: Unknown
<220> FEATURE:
<223> OTHER INFORMATION: Talaromyces spp

<400> SEQUENCE: 29

Val Glu Phe Ile Lys Val Pro Pro Thr Tyr Tyr
1               5                   10

<210> SEQ ID NO 30
<211> LENGTH: 12
<212> TYPE: PRT
<213> ORGANISM: Unknown
<220> FEATURE:
<223> OTHER INFORMATION: Talaromyces spp

<400> SEQUENCE: 30

Thr Tyr Tyr Asp Asn Met Trp Met Arg Leu Lys Lys
1               5                   10

<210> SEQ ID NO 31
<211> LENGTH: 8
<212> TYPE: PRT
<213> ORGANISM: Unknown
<220> FEATURE:
<223> OTHER INFORMATION: Talaromyces spp

<400> SEQUENCE: 31
```

```
Lys Lys Leu Asp Ile Leu Ile Asp
1               5

<210> SEQ ID NO 32
<211> LENGTH: 8
<212> TYPE: PRT
<213> ORGANISM: Unknown
<220> FEATURE:
<223> OTHER INFORMATION: Talaromyces spp

<400> SEQUENCE: 32

Ile Asp Phe Asp Glu Gly Gly Tyr
1               5

<210> SEQ ID NO 33
<211> LENGTH: 7
<212> TYPE: PRT
<213> ORGANISM: Unknown
<220> FEATURE:
<223> OTHER INFORMATION: Talaromyces spp

<400> SEQUENCE: 33

Asn Asn Phe Ser Gly Phe Gly
1               5

<210> SEQ ID NO 34
<211> LENGTH: 9
<212> TYPE: PRT
<213> ORGANISM: Artificial Sequence
<220> FEATURE:
<223> OTHER INFORMATION: Talaromyces spp

<400> SEQUENCE: 34

Ala Thr Ile Arg Thr Tyr Gly Asp Thr
1               5

<210> SEQ ID NO 35
<211> LENGTH: 9
<212> TYPE: PRT
<213> ORGANISM: Unknown
<220> FEATURE:
<223> OTHER INFORMATION: Talaromyces spp

<400> SEQUENCE: 35

Asp Thr Thr His Thr Leu Ile Gln Arg
1               5

<210> SEQ ID NO 36
<211> LENGTH: 7
<212> TYPE: PRT
<213> ORGANISM: Unknown
<220> FEATURE:
<223> OTHER INFORMATION: Talaromyces spp

<400> SEQUENCE: 36

Cys Ala Tyr Tyr Glu Lys Val
1               5

<210> SEQ ID NO 37
<211> LENGTH: 6
<212> TYPE: PRT
<213> ORGANISM: Unknown
<220> FEATURE:
<223> OTHER INFORMATION: Talaromyces spp

<400> SEQUENCE: 37
```

```
Gln Ser Asp Asn Leu Pro
1               5
```

<210> SEQ ID NO 38
<211> LENGTH: 18
<212> TYPE: PRT
<213> ORGANISM: Trichoderma harzianum

<400> SEQUENCE: 38

```
Glu Ala Val Tyr Asn Lys Ala Val Ala Glu Gly Ala Ile Ala Val Gln
1               5                   10                  15

Gly Pro
```

<210> SEQ ID NO 39
<211> LENGTH: 17
<212> TYPE: PRT
<213> ORGANISM: Trichoderma harzianum

<400> SEQUENCE: 39

```
Phe His Arg Phe Trp Ser Val Asp Asp Ser Gln Ile Cys Thr Glu Phe
1               5                   10                  15

Ser
```

<210> SEQ ID NO 40
<211> LENGTH: 20
<212> TYPE: PRT
<213> ORGANISM: Trichoderma harzianum

<400> SEQUENCE: 40

```
Val Glu Phe Ile Asn Val Pro Thr Thr Tyr Tyr Asp Thr Met Arg Gln
1               5                   10                  15

Arg Leu Lys Thr
            20
```

<210> SEQ ID NO 41
<211> LENGTH: 14
<212> TYPE: PRT
<213> ORGANISM: Trichoderma harzianum

<400> SEQUENCE: 41

```
Gln Arg Leu Asn Ile Leu Ile Asp Tyr Asp Glu Ala Gly Tyr
1               5                   10
```

<210> SEQ ID NO 42
<211> LENGTH: 12
<212> TYPE: PRT
<213> ORGANISM: Trichoderma harzianum

<400> SEQUENCE: 42

```
Glu Ile Ile Gln Arg Asn Asn Phe Glu Gly Phe Gly
1               5                   10
```

<210> SEQ ID NO 43
<211> LENGTH: 16
<212> TYPE: PRT
<213> ORGANISM: Trichoderma harzianum

<400> SEQUENCE: 43

```
Ala Val Ile Cys Thr Tyr Gly Asp Thr Thr His Thr Leu Ile Asn Arg
1               5                   10                  15
```

<210> SEQ ID NO 44
<211> LENGTH: 12

```
<212> TYPE: PRT
<213> ORGANISM: Trichoderma harzianum

<400> SEQUENCE: 44

Glu Met Val Ser Ala Cys Ala Phe Tyr Glu Gln Cys
1               5                   10

<210> SEQ ID NO 45
<211> LENGTH: 7
<212> TYPE: PRT
<213> ORGANISM: Trichoderma harzianum

<400> SEQUENCE: 45

Gly Phe Gly Ala Gly Asn Phe
1               5

<210> SEQ ID NO 46
<211> LENGTH: 6
<212> TYPE: PRT
<213> ORGANISM: Trichoderma harzianum

<400> SEQUENCE: 46

Thr Pro Asp Asn Phe Ala
1               5

<210> SEQ ID NO 47
<211> LENGTH: 18
<212> TYPE: PRT
<213> ORGANISM: Unknown
<220> FEATURE:
<223> OTHER INFORMATION: Talaromyces spp

<400> SEQUENCE: 47

Asp Asp Val Phe Ala Ala Ala Val Gln Asn Gly Ala Val Ala Val Ser
1               5                   10                  15

Gln Pro

<210> SEQ ID NO 48
<211> LENGTH: 17
<212> TYPE: PRT
<213> ORGANISM: Unknown
<220> FEATURE:
<223> OTHER INFORMATION: Talaromyces spp

<400> SEQUENCE: 48

Phe His Arg Phe Arg Ser Val Asp Asp Lys Asp Ile Cys Thr Asp Tyr
1               5                   10                  15

Ser

<210> SEQ ID NO 49
<211> LENGTH: 20
<212> TYPE: PRT
<213> ORGANISM: Unknown
<220> FEATURE:
<223> OTHER INFORMATION: Talaromyces spp

<400> SEQUENCE: 49

Val Glu Phe Ile Lys Val Pro Pro Thr Tyr Tyr Asp Asn Met Trp Met
1               5                   10                  15

Arg Leu Lys Lys
            20

<210> SEQ ID NO 50
<211> LENGTH: 14
```

```
<212> TYPE: PRT
<213> ORGANISM: Unknown
<220> FEATURE:
<223> OTHER INFORMATION: Talaromyces spp

<400> SEQUENCE: 50

Lys Lys Leu Asp Ile Leu Ile Asp Phe Asp Glu Gly Gly Tyr
1               5                   10

<210> SEQ ID NO 51
<211> LENGTH: 12
<212> TYPE: PRT
<213> ORGANISM: Unknown
<220> FEATURE:
<223> OTHER INFORMATION: Talaromyces spp

<400> SEQUENCE: 51

Glu Ile Ile Gln Arg Asn Asn Phe Ser Gly Phe Gly
1               5                   10

<210> SEQ ID NO 52
<211> LENGTH: 16
<212> TYPE: PRT
<213> ORGANISM: Unknown
<220> FEATURE:
<223> OTHER INFORMATION: Talaromyces spp

<400> SEQUENCE: 52

Ala Thr Ile Arg Thr Tyr Gly Asp Thr Thr His Thr Leu Ile Gln Arg
1               5                   10                  15

<210> SEQ ID NO 53
<211> LENGTH: 12
<212> TYPE: PRT
<213> ORGANISM: Unknown
<220> FEATURE:
<223> OTHER INFORMATION: Talaromyces spp

<400> SEQUENCE: 53

Glu Met Glu Lys Val Cys Ala Tyr Tyr Glu Lys Val
1               5                   10

<210> SEQ ID NO 54
<211> LENGTH: 6
<212> TYPE: PRT
<213> ORGANISM: Unknown
<220> FEATURE:
<223> OTHER INFORMATION: Talaromyces spp

<400> SEQUENCE: 54

Gln Ser Asp Asn Leu Pro
1               5

<210> SEQ ID NO 55
<211> LENGTH: 12
<212> TYPE: PRT
<213> ORGANISM: Glycine max

<400> SEQUENCE: 55

Glu Ala Ala Phe Ser Ala Ser Val Ala Lys Gly Ala
1               5                   10

<210> SEQ ID NO 56
<211> LENGTH: 11
<212> TYPE: PRT
<213> ORGANISM: Glycine max
```

-continued

```
<400> SEQUENCE: 56

Val Ala Lys Gly Ala Glu Pro Ala Ser Pro Pro
1               5                   10

<210> SEQ ID NO 57
<211> LENGTH: 9
<212> TYPE: PRT
<213> ORGANISM: Glycine max

<400> SEQUENCE: 57

Phe His Glu Phe Ala Glu Phe Thr Ala
1               5

<210> SEQ ID NO 58
<211> LENGTH: 10
<212> TYPE: PRT
<213> ORGANISM: Glycine max

<400> SEQUENCE: 58

Thr Ala Glu Asp Val Gly Thr Ser Glu Ser
1               5                   10

<210> SEQ ID NO 59
<211> LENGTH: 12
<212> TYPE: PRT
<213> ORGANISM: Glycine max

<400> SEQUENCE: 59

Phe Glu Phe Met Pro Ser Pro Pro Thr Tyr Tyr
1               5                   10

<210> SEQ ID NO 60
<211> LENGTH: 10
<212> TYPE: PRT
<213> ORGANISM: Glycine max

<400> SEQUENCE: 60

Thr Tyr Tyr Ala Asn Leu His Asn Arg Ala
1               5                   10

<210> SEQ ID NO 61
<211> LENGTH: 8
<212> TYPE: PRT
<213> ORGANISM: Glycine max

<400> SEQUENCE: 61

Glu Glu Leu Gly Ile Leu Val Asp
1               5

<210> SEQ ID NO 62
<211> LENGTH: 8
<212> TYPE: PRT
<213> ORGANISM: Glycine max

<400> SEQUENCE: 62

Val Asp Arg Asp Asp Gln Gly Thr
1               5

<210> SEQ ID NO 63
<211> LENGTH: 9
<212> TYPE: PRT
<213> ORGANISM: Glycine max

<400> SEQUENCE: 63
```

```
Glu Ile Ile Gln Arg Ile Gly Cys Met
1               5

<210> SEQ ID NO 64
<211> LENGTH: 9
<212> TYPE: PRT
<213> ORGANISM: Glycine max

<400> SEQUENCE: 64

Cys Met Val Glu Asp Glu Glu Gly Lys
1               5

<210> SEQ ID NO 65
<211> LENGTH: 8
<212> TYPE: PRT
<213> ORGANISM: Glycine max

<400> SEQUENCE: 65

Gly Lys Val Tyr Gln Lys Gly Ala
1               5

<210> SEQ ID NO 66
<211> LENGTH: 10
<212> TYPE: PRT
<213> ORGANISM: Glycine max

<400> SEQUENCE: 66

Tyr Gln Lys Gly Ala Cys Gly Gly Phe Gly
1               5                   10

<210> SEQ ID NO 67
<211> LENGTH: 9
<212> TYPE: PRT
<213> ORGANISM: Glycine max

<400> SEQUENCE: 67

Ala Glu Val Arg Leu Tyr Gly Asp Val
1               5

<210> SEQ ID NO 68
<211> LENGTH: 9
<212> TYPE: PRT
<213> ORGANISM: Glycine max

<400> SEQUENCE: 68

Asp Val Val Leu Arg Tyr Val Ser Tyr
1               5

<210> SEQ ID NO 69
<211> LENGTH: 7
<212> TYPE: PRT
<213> ORGANISM: Glycine max

<400> SEQUENCE: 69

Glu Leu Ala Pro Ala Val Arg
1               5

<210> SEQ ID NO 70
<211> LENGTH: 7
<212> TYPE: PRT
<213> ORGANISM: Glycine max

<400> SEQUENCE: 70

Val Arg Tyr Leu Lys Gly Phe
1               5
```

```
<210> SEQ ID NO 71
<211> LENGTH: 7
<212> TYPE: PRT
<213> ORGANISM: Glycine max

<400> SEQUENCE: 71

Gly Phe Gly Lys Gly Asn Phe
1               5

<210> SEQ ID NO 72
<211> LENGTH: 6
<212> TYPE: PRT
<213> ORGANISM: Glycine max

<400> SEQUENCE: 72

Phe Val Arg Thr Asn Pro
1               5

<210> SEQ ID NO 73
<211> LENGTH: 12
<212> TYPE: PRT
<213> ORGANISM: Artificial Sequence
<220> FEATURE:
<223> OTHER INFORMATION: Dicot plant HPPD consensus sequence
<220> FEATURE:
<221> NAME/KEY: X
<222> LOCATION: (1)..(1)
<223> OTHER INFORMATION: X= E or R
<220> FEATURE:
<221> NAME/KEY: MISC_FEATURE
<222> LOCATION: (1)..(1)
<220> FEATURE:
<221> NAME/KEY: X
<222> LOCATION: (2)..(2)
<223> OTHER INFORMATION: X= any amino acid
<220> FEATURE:
<221> NAME/KEY: X
<222> LOCATION: (5)..(5)
<223> OTHER INFORMATION: X= S or T
<220> FEATURE:
<221> NAME/KEY: X
<222> LOCATION: (6)..(6)
<223> OTHER INFORMATION: X= A, I or T
<220> FEATURE:
<221> NAME/KEY: X
<222> LOCATION: (9)..(9)
<223> OTHER INFORMATION: X= any amino acid
<220> FEATURE:
<221> NAME/KEY: X
<222> LOCATION: (10)..(10)
<223> OTHER INFORMATION: X= K, N or H

<400> SEQUENCE: 73

Xaa Xaa Ala Phe Xaa Xaa Ser Val Xaa Xaa Gly Ala
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Dicot plant HPPD consensus sequence
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = K, N or H
<220> FEATURE:
```

```
<221> NAME/KEY: MISC_FEATURE
<222> LOCATION: (8)..(8)
<223> OTHER INFORMATION: X = A or S
<220> FEATURE:
<221> NAME/KEY: MISC_FEATURE
<222> LOCATION: (10)..(10)
<223> OTHER INFORMATION: X = P or E

<400> SEQUENCE: 74

Val Xaa Xaa Gly Ala Glu Pro Xaa Ser Xaa Pro
1               5                   10

<210> SEQ ID NO 75
<211> LENGTH: 9
<212> TYPE: PRT
<213> ORGANISM: Artificial Sequence
<220> FEATURE:
<223> OTHER INFORMATION: Dicot plant HPPD consensus sequence
<220> FEATURE:
<221> NAME/KEY: MISC_FEATURE
<222> LOCATION: (3)..(3)
<223> OTHER INFORMATION: X = E or Q
<220> FEATURE:
<221> NAME/KEY: MISC_FEATURE
<222> LOCATION: (9)..(9)
<223> OTHER INFORMATION: X = A or T

<400> SEQUENCE: 75

Phe His Xaa Phe Ala Glu Phe Thr Xaa
1               5

<210> SEQ ID NO 76
<211> LENGTH: 10
<212> TYPE: PRT
<213> ORGANISM: Artificial Sequence
<220> FEATURE:
<223> OTHER INFORMATION: Dicot plant HPPD consensus sequence
<220> FEATURE:
<221> NAME/KEY: MISC_FEATURE
<222> LOCATION: (2)..(2)
<223> OTHER INFORMATION: X = A or T
<220> FEATURE:
<221> NAME/KEY: MISC_FEATURE
<222> LOCATION: (3)..(3)
<223> OTHER INFORMATION: X = E or D
<220> FEATURE:
<221> NAME/KEY: MISC_FEATURE
<222> LOCATION: (8)..(8)
<223> OTHER INFORMATION: X = A or S

<400> SEQUENCE: 76

Thr Xaa Xaa Asp Val Gly Thr Xaa Glu Ser
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Dicot plant HPPD consensus sequence
<220> FEATURE:
<221> NAME/KEY: MISC_FEATURE
<222> LOCATION: (2)..(2)
<223> OTHER INFORMATION: X = E or D
<220> FEATURE:
<221> NAME/KEY: MISC_FEATURE
<222> LOCATION: (9)..(9)
<223> OTHER INFORMATION: X = P or V

<400> SEQUENCE: 77

Phe Xaa Phe Met Pro Ser Pro Pro Xaa Thr Tyr Tyr
1               5                   10
```

```
<210> SEQ ID NO 78
<211> LENGTH: 10
<212> TYPE: PRT
<213> ORGANISM: Artificial Sequence
<220> FEATURE:
<223> OTHER INFORMATION: Dicot plant HPPD consensus sequence
<220> FEATURE:
<221> NAME/KEY: MISC_FEATURE
<222> LOCATION: (4)..(4)
<223> OTHER INFORMATION: X = any amino acid
<220> FEATURE:
<221> NAME/KEY: MISC_FEATURE
<222> LOCATION: (5)..(5)
<223> OTHER INFORMATION: X = N or K
<220> FEATURE:
<221> NAME/KEY: MISC_FEATURE
<222> LOCATION: (7)..(7)
<223> OTHER INFORMATION: X = H, K or R
<220> FEATURE:
<221> NAME/KEY: MISC_FEATURE
<222> LOCATION: (8)..(8)
<223> OTHER INFORMATION: X = any amino acid
<220> FEATURE:
<221> NAME/KEY: MISC_FEATURE
<222> LOCATION: (9)..(9)
<223> OTHER INFORMATION: X = A or G

<400> SEQUENCE: 78

Thr Tyr Tyr Xaa Xaa Leu Xaa Xaa Xaa Leu
1               5                   10

<210> SEQ ID NO 79
<211> LENGTH: 8
<212> TYPE: PRT
<213> ORGANISM: Artificial Sequence
<220> FEATURE:
<223> OTHER INFORMATION: Dicot plant HPPD consensus sequence
<220> FEATURE:
<221> NAME/KEY: MISC_FEATURE
<222> LOCATION: (3)..(3)
<223> OTHER INFORMATION: X = R or K

<400> SEQUENCE: 79

Val Asp Xaa Asp Asp Gln Gly Thr
1               5

<210> SEQ ID NO 80
<211> LENGTH: 9
<212> TYPE: PRT
<213> ORGANISM: Artificial Sequence
<220> FEATURE:
<223> OTHER INFORMATION: Dicot plant HPPD consensus sequence
<220> FEATURE:
<221> NAME/KEY: MISC_FEATURE
<222> LOCATION: (6)..(6)
<223> OTHER INFORMATION: X = I or V

<400> SEQUENCE: 80

Glu Ile Ile Gln Arg Xaa Gly Cys Met
1               5

<210> SEQ ID NO 81
<211> LENGTH: 9
<212> TYPE: PRT
<213> ORGANISM: Artificial Sequence
<220> FEATURE:
<223> OTHER INFORMATION: Dicot plant HPPD consensus sequence
<220> FEATURE:
<221> NAME/KEY: MISC_FEATURE
<222> LOCATION: (3)..(3)
<223> OTHER INFORMATION: X = any amino acid
```

```
<220> FEATURE:
<221> NAME/KEY: MISC_FEATURE
<222> LOCATION: (4)..(4)
<223> OTHER INFORMATION: X = E, K or Q
<220> FEATURE:
<221> NAME/KEY: MISC_FEATURE
<222> LOCATION: (5)..(5)
<223> OTHER INFORMATION: X = D or N
<220> FEATURE:
<221> NAME/KEY: MISC_FEATURE
<222> LOCATION: (6)..(6)
<223> OTHER INFORMATION: X = E or A
<220> FEATURE:
<221> NAME/KEY: MISC_FEATURE
<222> LOCATION: (9)..(9)
<223> OTHER INFORMATION: X = K or E

<400> SEQUENCE: 81

Cys Met Xaa Xaa Xaa Xaa Glu Gly Xaa
1               5

<210> SEQ ID NO 82
<211> LENGTH: 8
<212> TYPE: PRT
<213> ORGANISM: Artificial Sequence
<220> FEATURE:
<223> OTHER INFORMATION: Dicot plant HPPD consensus sequence
<220> FEATURE:
<221> NAME/KEY: MISC_FEATURE
<222> LOCATION: (2)..(2)
<223> OTHER INFORMATION: X = K or E
<220> FEATURE:
<221> NAME/KEY: MISC_FEATURE
<222> LOCATION: (3)..(3)
<223> OTHER INFORMATION: X = X = any amino acid
<220> FEATURE:
<221> NAME/KEY: MISC_FEATURE
<222> LOCATION: (6)..(6)
<223> OTHER INFORMATION: X = K or S
<220> FEATURE:
<221> NAME/KEY: MISC_FEATURE
<222> LOCATION: (8)..(8)
<223> OTHER INFORMATION: X = G or A

<400> SEQUENCE: 82

Gly Xaa Xaa Tyr Gln Xaa Gly Xaa
1               5

<210> SEQ ID NO 83
<211> LENGTH: 10
<212> TYPE: PRT
<213> ORGANISM: Artificial Sequence
<220> FEATURE:
<223> OTHER INFORMATION: Dicot plant HPPD consensus sequence
<220> FEATURE:
<221> NAME/KEY: MISC_FEATURE
<222> LOCATION: (3)..(3)
<223> OTHER INFORMATION: X = K or S
<220> FEATURE:
<221> NAME/KEY: MISC_FEATURE
<222> LOCATION: (5)..(5)
<223> OTHER INFORMATION: X = G or A

<400> SEQUENCE: 83

Tyr Gln Xaa Gly Xaa Cys Gly Gly Phe Gly
1               5                   10

<210> SEQ ID NO 84
<211> LENGTH: 9
<212> TYPE: PRT
<213> ORGANISM: Artificial Sequence
<220> FEATURE:
<223> OTHER INFORMATION: Dicot plant HPPD consensus sequence
```

```
<220> FEATURE:
<221> NAME/KEY: MISC_FEATURE
<222> LOCATION: (1)..(1)
<223> OTHER INFORMATION: X = A or S
<220> FEATURE:
<221> NAME/KEY: MISC_FEATURE
<222> LOCATION: (4)..(4)
<223> OTHER INFORMATION: X = R, H or K

<400> SEQUENCE: 84

Xaa Glu Val Xaa Leu Tyr Gly Asp Val
1               5

<210> SEQ ID NO 85
<211> LENGTH: 7
<212> TYPE: PRT
<213> ORGANISM: Artificial Sequence
<220> FEATURE:
<223> OTHER INFORMATION: Dicot plant HPPD consensus sequence
<220> FEATURE:
<221> NAME/KEY: MISC_FEATURE
<222> LOCATION: (1)..(1)
<223> OTHER INFORMATION: X = E or Q
<220> FEATURE:
<221> NAME/KEY: MISC_FEATURE
<222> LOCATION: (3)..(3)
<223> OTHER INFORMATION: X = A, G or S
<220> FEATURE:
<221> NAME/KEY: MISC_FEATURE
<222> LOCATION: (5)..(5)
<223> OTHER INFORMATION: X = A or V
<220> FEATURE:
<221> NAME/KEY: MISC_FEATURE
<222> LOCATION: (6)..(6)
<223> OTHER INFORMATION: X = V, L or I
<220> FEATURE:
<221> NAME/KEY: MISC_FEATURE
<222> LOCATION: (7)..(7)
<223> OTHER INFORMATION: X = any amino acid

<400> SEQUENCE: 85

Xaa Leu Xaa Pro Xaa Xaa Xaa
1               5

<210> SEQ ID NO 86
<211> LENGTH: 7
<212> TYPE: PRT
<213> ORGANISM: Artificial Sequence
<220> FEATURE:
<223> OTHER INFORMATION: Dicot plant HPPD consensus sequence
<220> FEATURE:
<221> NAME/KEY: MISC_FEATURE
<222> LOCATION: (1)..(1)
<223> OTHER INFORMATION: X = V, L or I
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (4)..(4)
<223> OTHER INFORMATION: X = L, V or I
<220> FEATURE:
<221> NAME/KEY: MISC_FEATURE
<222> LOCATION: (5)..(5)
<223> OTHER INFORMATION: X = K or A
<220> FEATURE:
<221> NAME/KEY: MISC_FEATURE
<222> LOCATION: (6)..(6)
<223> OTHER INFORMATION: X = any amino acid

<400> SEQUENCE: 86

Xaa Xaa Tyr Xaa Xaa Xaa Phe
1               5
```

```
<210> SEQ ID NO 87
<211> LENGTH: 6
<212> TYPE: PRT
<213> ORGANISM: Artificial Sequence
<220> FEATURE:
<223> OTHER INFORMATION: Dicot plant HPPD consensus sequence
<220> FEATURE:
<221> NAME/KEY: MISC_FEATURE
<222> LOCATION: (2)..(2)
<223> OTHER INFORMATION: X = V or I
<220> FEATURE:
<221> NAME/KEY: MISC_FEATURE
<222> LOCATION: (4)..(4)
<223> OTHER INFORMATION: X = any amino acid

<400> SEQUENCE: 87

Phe Xaa Arg Xaa Asn Pro
1               5

<210> SEQ ID NO 88
<211> LENGTH: 12
<212> TYPE: PRT
<213> ORGANISM: Artificial Sequence
<220> FEATURE:
<223> OTHER INFORMATION: Monocot plant HPPD consensus sequence
<220> FEATURE:
<221> NAME/KEY: MISC_FEATURE
<222> LOCATION: (1)..(1)
<223> OTHER INFORMATION: X = E or A
<220> FEATURE:
<221> NAME/KEY: MISC_FEATURE
<222> LOCATION: (2)..(2)
<223> OTHER INFORMATION: X = D or E
<220> FEATURE:
<221> NAME/KEY: MISC_FEATURE
<222> LOCATION: (6)..(6)
<223> OTHER INFORMATION: X = A or V
<220> FEATURE:
<221> NAME/KEY: MISC_FEATURE
<222> LOCATION: (10)..(10)
<223> OTHER INFORMATION: X = A or G

<400> SEQUENCE: 88

Xaa Xaa Ala Phe Arg Xaa Ser Val Ala Xaa Gly Ala
1               5                   10

<210> SEQ ID NO 89
<211> LENGTH: 11
<212> TYPE: PRT
<213> ORGANISM: Artificial Sequence
<220> FEATURE:
<223> OTHER INFORMATION: Monocot plant HPPD consensus sequence
<220> FEATURE:
<221> NAME/KEY: MISC_FEATURE
<222> LOCATION: (3)..(3)
<223> OTHER INFORMATION: X = A or G
<220> FEATURE:
<221> NAME/KEY: MISC_FEATURE
<222> LOCATION: (10)..(10)
<223> OTHER INFORMATION: X = Q or A

<400> SEQUENCE: 89

Val Ala Xaa Gly Ala Arg Pro Ala Phe Xaa Pro
1               5                   10

<210> SEQ ID NO 90
<211> LENGTH: 9
<212> TYPE: PRT
<213> ORGANISM: Artificial Sequence
<220> FEATURE:
<223> OTHER INFORMATION: Monocot plant HPPD consensus sequence
```

```
<220> FEATURE:
<221> NAME/KEY: MISC_FEATURE
<222> LOCATION: (9)..(9)
<223> OTHER INFORMATION: X = A or T

<400> SEQUENCE: 90

Phe His Glu Phe Ala Glu Phe Thr Xaa
1               5

<210> SEQ ID NO 91
<211> LENGTH: 10
<212> TYPE: PRT
<213> ORGANISM: Artificial Sequence
<220> FEATURE:
<223> OTHER INFORMATION: Monocot plant HPPD consensus sequence
<220> FEATURE:
<221> NAME/KEY: MISC_FEATURE
<222> LOCATION: (2)..(2)
<223> OTHER INFORMATION: X = A or T
<220> FEATURE:
<221> NAME/KEY: MISC_FEATURE
<222> LOCATION: (8)..(8)
<223> OTHER INFORMATION: X = A or T

<400> SEQUENCE: 91

Thr Xaa Glu Asp Val Gly Thr Xaa Glu Ser
1               5                   10

<210> SEQ ID NO 92
<211> LENGTH: 13
<212> TYPE: PRT
<213> ORGANISM: Artificial Sequence
<220> FEATURE:
<223> OTHER INFORMATION: Monocot plant HPPD consensus sequence
<220> FEATURE:
<221> NAME/KEY: MISC_FEATURE
<222> LOCATION: (4)..(4)
<223> OTHER INFORMATION: X = L or M
<220> FEATURE:
<221> NAME/KEY: MISC_FEATURE
<222> LOCATION: (8)..(8)
<223> OTHER INFORMATION: X = P, T or Q
<220> FEATURE:
<221> NAME/KEY: MISC_FEATURE
<222> LOCATION: (9)..(9)
<223> OTHER INFORMATION: X = S, P or A
<220> FEATURE:
<221> NAME/KEY: MISC_FEATURE
<222> LOCATION: (10)..(10)
<223> OTHER INFORMATION: X = D, N or K

<400> SEQUENCE: 92

Phe Glu Phe Xaa Ala Pro Pro Xaa Xaa Xaa Tyr Tyr Trp
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Monocot plant HPPD consensus sequence
<220> FEATURE:
<221> NAME/KEY: MISC_FEATURE
<222> LOCATION: (1)..(1)
<223> OTHER INFORMATION: X = D, N or K
<220> FEATURE:
<221> NAME/KEY: MISC_FEATURE
<222> LOCATION: (4)..(4)
<223> OTHER INFORMATION: X = D or E

<400> SEQUENCE: 93

Xaa Tyr Tyr Xaa Gly Val Arg Arg Gly Val
```

<210> SEQ ID NO 94
<211> LENGTH: 8
<212> TYPE: PRT
<213> ORGANISM: Artificial Sequence
<220> FEATURE:
<223> OTHER INFORMATION: Monocot plant HPPD consensus sequence

<400> SEQUENCE: 94

Gln Glu Leu Gly Val Leu Val Asp
1               5

<210> SEQ ID NO 95
<211> LENGTH: 8
<212> TYPE: PRT
<213> ORGANISM: Artificial Sequence
<220> FEATURE:
<223> OTHER INFORMATION: Monocot plant HPPD consensus sequence

<400> SEQUENCE: 95

Val Asp Arg Asp Asp Gln Gly Val
1               5

<210> SEQ ID NO 96
<211> LENGTH: 9
<212> TYPE: PRT
<213> ORGANISM: Artificial Sequence
<220> FEATURE:
<223> OTHER INFORMATION: Monocot plant HPPD consensus sequence

<400> SEQUENCE: 96

Glu Met Ile Gln Arg Ile Gly Cys Met
1               5

<210> SEQ ID NO 97
<211> LENGTH: 9
<212> TYPE: PRT
<213> ORGANISM: Artificial Sequence
<220> FEATURE:
<223> OTHER INFORMATION: Monocot plant HPPD consensus sequence
<220> FEATURE:
<221> NAME/KEY: MISC_FEATURE
<222> LOCATION: (7)..(7)
<223> OTHER INFORMATION: X = K, S or V

<400> SEQUENCE: 97

Cys Met Glu Lys Asp Glu Xaa Gly Gln
1               5

<210> SEQ ID NO 98
<211> LENGTH: 8
<212> TYPE: PRT
<213> ORGANISM: Artificial Sequence
<220> FEATURE:
<223> OTHER INFORMATION: Monocot plant HPPD consensus sequence

<400> SEQUENCE: 98

Gly Gln Glu Tyr Gln Lys Gly Ala
1               5

<210> SEQ ID NO 99
<211> LENGTH: 9
<212> TYPE: PRT
<213> ORGANISM: Artificial Sequence
<220> FEATURE:
<223> OTHER INFORMATION: AEVELYGDV

```
<400> SEQUENCE: 99

Ala Glu Val Glu Leu Tyr Gly Asp Val
1               5

<210> SEQ ID NO 100
<211> LENGTH: 7
<212> TYPE: PRT
<213> ORGANISM: Artificial Sequence
<220> FEATURE:
<223> OTHER INFORMATION: Monocot plant HPPD consensus sequence
<220> FEATURE:
<221> NAME/KEY: MISC_FEATURE
<222> LOCATION: (2)..(2)
<223> OTHER INFORMATION: X = L or M
<220> FEATURE:
<221> NAME/KEY: MISC_FEATURE
<222> LOCATION: (5)..(5)
<223> OTHER INFORMATION: X = A or V
<220> FEATURE:
<221> NAME/KEY: MISC_FEATURE
<222> LOCATION: (6)..(6)
<223> OTHER INFORMATION: X = A or I
<220> FEATURE:
<221> NAME/KEY: MISC_FEATURE
<222> LOCATION: (7)..(7)
<223> OTHER INFORMATION: X = A or D

<400> SEQUENCE: 100

Glu Xaa Ala Pro Xaa Xaa Xaa
1               5

<210> SEQ ID NO 101
<211> LENGTH: 7
<212> TYPE: PRT
<213> ORGANISM: Artificial Sequence
<220> FEATURE:
<223> OTHER INFORMATION: Monocot plant HPPD consensus sequence
<220> FEATURE:
<221> NAME/KEY: MISC_FEATURE
<222> LOCATION: (1)..(1)
<223> OTHER INFORMATION: X = A or I
<220> FEATURE:
<221> NAME/KEY: MISC_FEATURE
<222> LOCATION: (2)..(2)
<223> OTHER INFORMATION: X = A or D
<220> FEATURE:
<221> NAME/KEY: MISC_FEATURE
<222> LOCATION: (4)..(4)
<223> OTHER INFORMATION: X = F, I or M
<220> FEATURE:
<221> NAME/KEY: MISC_FEATURE
<222> LOCATION: (5)..(5)
<223> OTHER INFORMATION: X = A, S or K

<400> SEQUENCE: 101

Xaa Xaa Tyr Xaa Xaa Gly Phe
1               5

<210> SEQ ID NO 102
<211> LENGTH: 6
<212> TYPE: PRT
<213> ORGANISM: Artificial Sequence
<220> FEATURE:
<223> OTHER INFORMATION: Monocot plant HPPD consensus sequence
<220> FEATURE:
<221> NAME/KEY: MISC_FEATURE
<222> LOCATION: (1)..(1)
<223> OTHER INFORMATION: X = F or V
<220> FEATURE:
<221> NAME/KEY: MISC_FEATURE
<222> LOCATION: (4)..(4)
<223> OTHER INFORMATION: X = F, A or V
```

```
<400> SEQUENCE: 102

Xaa Val Arg Xaa Asn Pro
1               5

<210> SEQ ID NO 103
<211> LENGTH: 28
<212> TYPE: PRT
<213> ORGANISM: Arabidopsis thaliana

<400> SEQUENCE: 103

Met Pro Pro Thr Pro Thr Thr Ala Ala Ala Thr Gly Ala Gly Ala Ala
1               5                   10                  15

Ala Val Thr Pro Glu His Ala Ala Phe Arg Leu Val
            20                  25

<210> SEQ ID NO 104
<211> LENGTH: 22
<212> TYPE: PRT
<213> ORGANISM: Arabidopsis thaliana

<400> SEQUENCE: 104

Met Gly His Gln Asn Ala Ala Val Ser Glu Asn Gln Asn His Asp Asp
1               5                   10                  15

Gly Ala Ala Ser Ser Pro
            20

<210> SEQ ID NO 105
<211> LENGTH: 49
<212> TYPE: PRT
<213> ORGANISM: Arabidopsis thaliana

<400> SEQUENCE: 105

Met Gly His Gln Asn Ala Ala Val Ser Glu Asn Gln Asn His Asp Asp
1               5                   10                  15

Gly Ala Ala Ser Ser Pro Gly Phe Lys Leu Val Gly Phe Ser Lys Phe
            20                  25                  30

Val Arg Lys Asn Pro Lys Ser Asp Lys Phe Lys Val Lys Arg Phe His
        35                  40                  45

His

<210> SEQ ID NO 106
<211> LENGTH: 415
<212> TYPE: PRT
<213> ORGANISM: Artificial Sequence
<220> FEATURE:
<223> OTHER INFORMATION: Trichoderma HPPD wherein aa 1-22 are
      substituted w aa 1-22 of Arabidopsis thaliana

<400> SEQUENCE: 106

Met Gly His Gln Asn Ala Ala Val Ser Glu Asn Gln Asn His Asp Asp
1               5                   10                  15

Gly Ala Ala Ser Ser Pro Asp Asn Phe Ala Ile Gln Pro Pro Ala Asp
            20                  25                  30

Phe Thr Gly Tyr Asp His Val Thr Trp Trp Val Gly Asn Ala Lys Gln
        35                  40                  45

Ala Ala Ala Tyr Tyr Thr Thr Leu Phe Gly Phe Glu Thr Thr Ala Tyr
    50                  55                  60

Arg Gly Leu Glu Thr Gly Ser Arg Tyr Phe Ala Ser Tyr Val Val Cys
65                  70                  75                  80

Asn Asn Gly Val Arg Phe Val Phe Thr Ser Pro Leu Arg Ser Glu Ala
```

```
                    85                  90                  95
His Leu Pro Glu Asp Glu Thr Ile Ser Asp Ser Glu Arg Lys Leu Leu
                100                 105                 110

Lys Glu Ile His Ala His Leu Glu Arg His Gly Asp Ala Val Lys Asp
            115                 120                 125

Val Ala Phe Glu Val Asp Asn Val Glu Ala Val Tyr Asn Lys Ala Val
        130                 135                 140

Ala Glu Gly Ala Ile Ala Val Gln Gly Pro Thr Ala Thr Lys Asp Asp
145                 150                 155                 160

His Gly Ser Val Thr Thr Ala Val Ile Cys Thr Tyr Gly Asp Thr Thr
                165                 170                 175

His Thr Leu Ile Asn Arg Arg Gly Tyr Thr Gly Pro Phe Leu Pro Gly
                180                 185                 190

Phe Arg Ala Gly Lys Glu Arg Thr Ser Ser Val Glu Met Pro Asn Val
            195                 200                 205

Pro Leu Ala Arg Ile Asp His Cys Val Gly Asn Gln Ser Trp Asn Glu
        210                 215                 220

Met Val Ser Ala Cys Ala Phe Tyr Glu Gln Cys Leu Ser Phe His Arg
225                 230                 235                 240

Phe Trp Ser Val Asp Asp Ser Gln Ile Cys Thr Glu Phe Ser Ala Leu
                245                 250                 255

Asn Ser Ile Val Met Ala Ser Pro Asn Asn Leu Val Lys Met Pro Ile
                260                 265                 270

Asn Glu Pro Ala Pro Gly Lys Lys Lys Ser Gln Ile Glu Glu Tyr Val
            275                 280                 285

Ile Phe Asn Ser Gly Pro Gly Val Gln His Ile Ala Leu Leu Thr Pro
        290                 295                 300

Asp Ile Ile Thr Ser Val Ser Ala Leu Arg Ala Arg Gly Val Glu Phe
305                 310                 315                 320

Ile Asn Val Pro Thr Thr Tyr Tyr Asp Thr Met Arg Gln Arg Leu Lys
                325                 330                 335

Thr Glu Lys Arg Asn Trp Gln Leu Lys Glu Asp Leu Asp Thr Ile Gln
            340                 345                 350

Arg Leu Asn Ile Leu Ile Asp Tyr Asp Glu Ala Gly Tyr Leu Leu Gln
        355                 360                 365

Leu Phe Thr Lys Pro Leu Met Asp Arg Pro Thr Val Phe Ile Glu Ile
370                 375                 380

Ile Gln Arg Asn Asn Phe Glu Gly Phe Gly Ala Gly Asn Phe Lys Ser
385                 390                 395                 400

Leu Phe Glu Ala Ile Glu Arg Glu Gln Ala Glu Arg Gly Asn Leu
            405                 410                 415
```

<210> SEQ ID NO 107
<211> LENGTH: 442
<212> TYPE: PRT
<213> ORGANISM: Artificial Sequence
<220> FEATURE:
<223> OTHER INFORMATION: Trichoderma HPPD wherein aa 1-22 are
      substituted w aa 1-49 of Arabidopsis thaliana

<400> SEQUENCE: 107

```
Met Gly His Gln Asn Ala Ala Val Ser Glu Asn Gln Asn His Asp Asp
1               5                   10                  15

Gly Ala Ala Ser Ser Pro Gly Phe Lys Leu Val Gly Phe Ser Lys Phe
            20                  25                  30
```

```
Val Arg Lys Asn Pro Lys Ser Asp Lys Phe Lys Val Lys Arg Phe His
         35                  40                  45

His Asp Asn Phe Ala Ile Gln Pro Pro Ala Asp Phe Thr Gly Tyr Asp
 50                  55                  60

His Val Thr Trp Trp Val Gly Asn Ala Lys Gln Ala Ala Tyr Tyr
 65              70                  75                  80

Thr Thr Leu Phe Gly Phe Glu Thr Thr Ala Tyr Arg Gly Leu Glu Thr
             85                  90                  95

Gly Ser Arg Tyr Phe Ala Ser Tyr Val Val Cys Asn Asn Gly Val Arg
             100                 105                 110

Phe Val Phe Thr Ser Pro Leu Arg Ser Glu Ala His Leu Pro Glu Asp
             115                 120                 125

Glu Thr Ile Ser Asp Ser Glu Arg Lys Leu Leu Lys Glu Ile His Ala
 130                 135                 140

His Leu Glu Arg His Gly Asp Ala Val Lys Asp Val Ala Phe Glu Val
 145                 150                 155                 160

Asp Asn Val Glu Ala Val Tyr Asn Lys Ala Val Ala Glu Gly Ala Ile
                 165                 170                 175

Ala Val Gln Gly Pro Thr Ala Thr Lys Asp Asp His Gly Ser Val Thr
             180                 185                 190

Thr Ala Val Ile Cys Thr Tyr Gly Asp Thr Thr His Thr Leu Ile Asn
         195                 200                 205

Arg Arg Gly Tyr Thr Gly Pro Phe Leu Pro Gly Phe Arg Ala Gly Lys
         210                 215                 220

Glu Arg Thr Ser Ser Val Glu Met Pro Asn Val Pro Leu Ala Arg Ile
225                 230                 235                 240

Asp His Cys Val Gly Asn Gln Ser Trp Asn Glu Met Val Ser Ala Cys
                 245                 250                 255

Ala Phe Tyr Glu Gln Cys Leu Ser Phe His Arg Phe Trp Ser Val Asp
             260                 265                 270

Asp Ser Gln Ile Cys Thr Glu Phe Ser Ala Leu Asn Ser Ile Val Met
             275                 280                 285

Ala Ser Pro Asn Asn Leu Val Lys Met Pro Ile Asn Glu Pro Ala Pro
 290                 295                 300

Gly Lys Lys Lys Ser Gln Ile Glu Glu Tyr Val Ile Phe Asn Ser Gly
305                 310                 315                 320

Pro Gly Val Gln His Ile Ala Leu Leu Thr Pro Asp Ile Ile Thr Ser
                 325                 330                 335

Val Ser Ala Leu Arg Ala Arg Gly Val Glu Phe Ile Asn Val Pro Thr
             340                 345                 350

Thr Tyr Tyr Asp Thr Met Arg Gln Arg Leu Lys Thr Glu Lys Arg Asn
             355                 360                 365

Trp Gln Leu Lys Glu Asp Leu Asp Thr Ile Gln Arg Leu Asn Ile Leu
 370                 375                 380

Ile Asp Tyr Asp Glu Ala Gly Tyr Leu Leu Gln Leu Phe Thr Lys Pro
385                 390                 395                 400

Leu Met Asp Arg Pro Thr Val Phe Ile Glu Ile Ile Gln Arg Asn Asn
                 405                 410                 415

Phe Glu Gly Phe Gly Ala Gly Asn Phe Lys Ser Leu Phe Glu Ala Ile
             420                 425                 430

Glu Arg Glu Gln Ala Glu Arg Gly Asn Leu
             435                 440
```

```
<210> SEQ ID NO 108
<211> LENGTH: 399
<212> TYPE: PRT
<213> ORGANISM: Artificial Sequence
<220> FEATURE:
<223> OTHER INFORMATION: Trichoderma HPPD wherein aa 1-38 are
      substituted w aa 1-22 of Arabidopsis thaliana

<400> SEQUENCE: 108

Met Gly His Gln Asn Ala Ala Val Ser Glu Asn Gln Asn His Asp Asp
1               5                   10                  15

Gly Ala Ala Ser Ser Pro Val Thr Trp Trp Val Gly Asn Ala Lys Gln
                20                  25                  30

Ala Ala Ala Tyr Tyr Thr Thr Leu Phe Gly Phe Glu Thr Ala Tyr
            35                  40                  45

Arg Gly Leu Glu Thr Gly Ser Arg Tyr Phe Ala Ser Tyr Val Val Cys
        50                  55                  60

Asn Asn Gly Val Arg Phe Val Phe Thr Ser Pro Leu Arg Ser Glu Ala
65                  70                  75                  80

His Leu Pro Glu Asp Glu Thr Ile Ser Asp Ser Glu Arg Lys Leu Leu
                85                  90                  95

Lys Glu Ile His Ala His Leu Glu Arg His Gly Asp Ala Val Lys Asp
            100                 105                 110

Val Ala Phe Glu Val Asp Asn Val Glu Ala Val Tyr Asn Lys Ala Val
        115                 120                 125

Ala Glu Gly Ala Ile Ala Val Gln Gly Pro Thr Ala Thr Lys Asp Asp
130                 135                 140

His Gly Ser Val Thr Thr Ala Val Ile Cys Thr Tyr Gly Asp Thr Thr
145                 150                 155                 160

His Thr Leu Ile Asn Arg Arg Gly Tyr Thr Gly Pro Phe Leu Pro Gly
                165                 170                 175

Phe Arg Ala Gly Lys Glu Arg Thr Ser Ser Val Glu Met Pro Asn Val
            180                 185                 190

Pro Leu Ala Arg Ile Asp His Cys Val Gly Asn Gln Ser Trp Asn Glu
        195                 200                 205

Met Val Ser Ala Cys Ala Phe Tyr Glu Gln Cys Leu Ser Phe His Arg
210                 215                 220

Phe Trp Ser Val Asp Asp Ser Gln Ile Cys Thr Glu Phe Ser Ala Leu
225                 230                 235                 240

Asn Ser Ile Val Met Ala Ser Pro Asn Asn Leu Val Lys Met Pro Ile
                245                 250                 255

Asn Glu Pro Ala Pro Gly Lys Lys Lys Ser Gln Ile Glu Glu Tyr Val
            260                 265                 270

Ile Phe Asn Ser Gly Pro Gly Val Gln His Ile Ala Leu Leu Thr Pro
        275                 280                 285

Asp Ile Ile Thr Ser Val Ser Ala Leu Arg Ala Arg Gly Val Glu Phe
290                 295                 300

Ile Asn Val Pro Thr Thr Tyr Tyr Asp Thr Met Arg Gln Arg Leu Lys
305                 310                 315                 320

Thr Glu Lys Arg Asn Trp Gln Leu Lys Glu Asp Leu Asp Thr Ile Gln
                325                 330                 335

Arg Leu Asn Ile Leu Ile Asp Tyr Asp Glu Ala Gly Tyr Leu Leu Gln
            340                 345                 350

Leu Phe Thr Lys Pro Leu Met Asp Arg Pro Thr Val Phe Ile Glu Ile
        355                 360                 365
```

```
Ile Gln Arg Asn Asn Phe Glu Gly Phe Gly Ala Gly Asn Phe Lys Ser
    370                 375                 380

Leu Phe Glu Ala Ile Glu Arg Glu Gln Ala Glu Arg Gly Asn Leu
385                 390                 395
```

<210> SEQ ID NO 109
<211> LENGTH: 426
<212> TYPE: PRT
<213> ORGANISM: Artificial Sequence
<220> FEATURE:
<223> OTHER INFORMATION: Trichoderma HPPD wherein aa 1-38 are
      substituted w aa 1-49 of Arabidopsis thaliana

<400> SEQUENCE: 109

```
Met Gly His Gln Asn Ala Ala Val Ser Glu Asn Gln Asn His Asp Asp
1                   5                   10                  15

Gly Ala Ala Ser Ser Pro Gly Phe Lys Leu Val Gly Phe Ser Lys Phe
                20                  25                  30

Val Arg Lys Asn Pro Lys Ser Asp Lys Phe Lys Val Lys Arg Phe His
            35                  40                  45

His Val Thr Trp Trp Val Gly Asn Ala Lys Gln Ala Ala Ala Tyr Tyr
        50                  55                  60

Thr Thr Leu Phe Gly Phe Glu Thr Thr Ala Tyr Arg Gly Leu Glu Thr
65                  70                  75                  80

Gly Ser Arg Tyr Phe Ala Ser Tyr Val Val Cys Asn Asn Gly Val Arg
                85                  90                  95

Phe Val Phe Thr Ser Pro Leu Arg Ser Glu Ala His Leu Pro Glu Asp
            100                 105                 110

Glu Thr Ile Ser Asp Ser Glu Arg Lys Leu Leu Lys Glu Ile His Ala
        115                 120                 125

His Leu Glu Arg His Gly Asp Ala Val Lys Asp Val Ala Phe Glu Val
    130                 135                 140

Asp Asn Val Glu Ala Val Tyr Asn Lys Ala Val Ala Glu Gly Ala Ile
145                 150                 155                 160

Ala Val Gln Gly Pro Thr Ala Thr Lys Asp Asp His Gly Ser Val Thr
                165                 170                 175

Thr Ala Val Ile Cys Thr Tyr Gly Asp Thr Thr His Thr Leu Ile Asn
            180                 185                 190

Arg Arg Gly Tyr Thr Gly Pro Phe Leu Pro Gly Phe Arg Ala Gly Lys
        195                 200                 205

Glu Arg Thr Ser Ser Val Glu Met Pro Asn Val Pro Leu Ala Arg Ile
    210                 215                 220

Asp His Cys Val Gly Asn Gln Ser Trp Asn Glu Met Val Ser Ala Cys
225                 230                 235                 240

Ala Phe Tyr Glu Gln Cys Leu Ser Phe His Arg Phe Trp Ser Val Asp
                245                 250                 255

Asp Ser Gln Ile Cys Thr Glu Phe Ser Ala Leu Asn Ser Ile Val Met
            260                 265                 270

Ala Ser Pro Asn Asn Leu Val Lys Met Pro Ile Asn Glu Pro Ala Pro
        275                 280                 285

Gly Lys Lys Lys Ser Gln Ile Glu Glu Tyr Val Ile Phe Asn Ser Gly
    290                 295                 300

Pro Gly Val Gln His Ile Ala Leu Leu Thr Pro Asp Ile Ile Thr Ser
305                 310                 315                 320

Val Ser Ala Leu Arg Ala Arg Gly Val Glu Phe Ile Asn Val Pro Thr
                325                 330                 335
```

-continued

```
Thr Tyr Tyr Asp Thr Met Arg Gln Arg Leu Lys Thr Glu Lys Arg Asn
            340                 345                 350

Trp Gln Leu Lys Glu Asp Leu Asp Thr Ile Gln Arg Leu Asn Ile Leu
        355                 360                 365

Ile Asp Tyr Asp Glu Ala Gly Tyr Leu Leu Gln Leu Phe Thr Lys Pro
    370                 375                 380

Leu Met Asp Arg Pro Thr Val Phe Ile Glu Ile Ile Gln Arg Asn Asn
385                 390                 395                 400

Phe Glu Gly Phe Gly Ala Gly Asn Phe Lys Ser Leu Phe Glu Ala Ile
                405                 410                 415

Glu Arg Glu Gln Ala Glu Arg Gly Asn Leu
            420                 425

<210> SEQ ID NO 110
<211> LENGTH: 423
<212> TYPE: PRT
<213> ORGANISM: Artificial Sequence
<220> FEATURE:
<223> OTHER INFORMATION: Talaromyces HPPD wherein aa 1-22 are
      substituted w aa 1-22 of Arabidopsis thaliana

<400> SEQUENCE: 110

Met Gly His Gln Asn Ala Ala Val Ser Glu Asn Gln Asn His Asp Asp
1               5                   10                  15

Gly Ala Ala Ser Ser Pro Pro Thr Thr Gln Ser Ala Leu Ser Ser Tyr
            20                  25                  30

Arg Gly Tyr Asp His Val His Trp Tyr Val Gly Asn Ala Lys Gln Ala
        35                  40                  45

Ala Thr Phe Tyr Ile Thr Arg Met Gly Phe Ser Arg Val Ala Tyr Arg
    50                  55                  60

Gly Leu Glu Thr Gly Ser Arg Ser Val Cys Ser His Val Val Arg Asn
65                  70                  75                  80

Gly Gly Ile Thr Phe Val Leu Thr Ser Pro Leu Arg Ser Pro Tyr Asn
                85                  90                  95

Thr Glu Lys Leu Glu Arg Leu Leu Pro Ser Ala Glu Glu Arg Glu Tyr
            100                 105                 110

Leu Lys Glu Ile His Glu His Leu Ala Arg His Gly Asp Ala Val Lys
        115                 120                 125

Asp Val Ala Phe Glu Val Asp Ser Val Asp Asp Val Phe Ala Ala Ala
    130                 135                 140

Val Gln Asn Gly Ala Val Ala Val Ser Gln Pro Lys Thr Val Glu Asp
145                 150                 155                 160

Glu Asn Gly Gln Val Arg Val Ala Thr Ile Arg Thr Tyr Gly Asp Thr
                165                 170                 175

Thr His Thr Leu Ile Gln Arg Arg Gly Val Glu Lys Pro Tyr Ser Gly
            180                 185                 190

Val Phe Leu Pro Gly Tyr Arg Asp Glu Thr Thr Ser Gly Ser Ser Asp
        195                 200                 205

Pro Ile Thr Ala Phe Leu Pro Lys Val Asp Leu Arg Arg Ile Asp His
    210                 215                 220

Cys Val Gly Asn Gln Asp Trp Asp Glu Met Glu Lys Val Cys Ala Tyr
225                 230                 235                 240

Tyr Glu Lys Val Leu Gly Phe His Arg Phe Arg Ser Val Asp Asp Lys
                245                 250                 255

Asp Ile Cys Thr Asp Tyr Ser Ala Leu Lys Ser Ile Val Met Ser Ser
```

```
                  260                 265                 270
Pro Asn Asp Ile Val Lys Met Pro Ile Asn Glu Pro Ala His Gly Lys
            275                 280                 285

Lys Gln Ser Gln Ile Glu Glu Tyr Val Asp Phe Tyr Asp Gly Ala Gly
        290                 295                 300

Val Gln His Ile Ala Leu Leu Thr Asp Asp Ile Ile Ser Ala Ile Thr
305                 310                 315                 320

Asn Leu Lys Ala Arg Gly Val Glu Phe Ile Lys Val Pro Pro Thr Tyr
                325                 330                 335

Tyr Asp Asn Met Trp Met Arg Leu Lys Lys Ala Gly Met Met Pro Lys
            340                 345                 350

Glu Ala Trp Glu Asp Ile Lys Lys Leu Asp Ile Leu Ile Asp Phe Asp
        355                 360                 365

Glu Gly Gly Tyr Leu Leu Gln Leu Phe Thr Lys His Leu Met Asp Arg
    370                 375                 380

Pro Thr Val Phe Ile Glu Ile Ile Gln Arg Asn Asn Phe Ser Gly Phe
385                 390                 395                 400

Gly Ala Gly Asn Phe Lys Ser Leu Phe Glu Ala Ile Glu Arg Glu Gln
                405                 410                 415

Ala Leu Arg Gly Asn Leu Ile
            420

<210> SEQ ID NO 111
<211> LENGTH: 450
<212> TYPE: PRT
<213> ORGANISM: Artificial Sequence
<220> FEATURE:
<223> OTHER INFORMATION: Talaromyces HPPD wherein aa 1-22 are
      substituted w aa 1-49 of Arabidopsis thaliana

<400> SEQUENCE: 111

Met Gly His Gln Asn Ala Ala Val Ser Glu Asn Gln Asn His Asp Asp
1               5                   10                  15

Gly Ala Ala Ser Ser Pro Gly Phe Lys Leu Val Gly Phe Ser Lys Phe
            20                  25                  30

Val Arg Lys Asn Pro Lys Ser Asp Lys Phe Lys Val Lys Arg Phe His
        35                  40                  45

His Pro Thr Thr Gln Ser Ala Leu Ser Ser Tyr Arg Gly Tyr Asp His
    50                  55                  60

Val His Trp Tyr Val Gly Asn Ala Lys Gln Ala Ala Thr Phe Tyr Ile
65                  70                  75                  80

Thr Arg Met Gly Phe Ser Arg Val Ala Tyr Arg Gly Leu Glu Thr Gly
                85                  90                  95

Ser Arg Ser Val Cys Ser His Val Arg Asn Gly Gly Ile Thr Phe
            100                 105                 110

Val Leu Thr Ser Pro Leu Arg Ser Pro Tyr Asn Thr Glu Lys Leu Glu
        115                 120                 125

Arg Leu Leu Pro Ser Ala Glu Glu Arg Glu Tyr Leu Lys Glu Ile His
    130                 135                 140

Glu His Leu Ala Arg His Gly Asp Ala Val Lys Asp Val Ala Phe Glu
145                 150                 155                 160

Val Asp Ser Val Asp Asp Val Phe Ala Ala Ala Val Gln Asn Gly Ala
                165                 170                 175

Val Ala Val Ser Gln Pro Lys Thr Val Glu Asp Glu Asn Gly Gln Val
            180                 185                 190
```

```
Arg Val Ala Thr Ile Arg Thr Tyr Gly Asp Thr Thr His Thr Leu Ile
            195                 200                 205

Gln Arg Arg Gly Val Glu Lys Pro Tyr Ser Gly Val Phe Leu Pro Gly
        210                 215                 220

Tyr Arg Asp Glu Thr Thr Ser Gly Ser Ser Asp Pro Ile Thr Ala Phe
225                 230                 235                 240

Leu Pro Lys Val Asp Leu Arg Arg Ile Asp His Cys Val Gly Asn Gln
                245                 250                 255

Asp Trp Asp Glu Met Glu Lys Val Cys Ala Tyr Tyr Glu Lys Val Leu
            260                 265                 270

Gly Phe His Arg Phe Arg Ser Val Asp Asp Lys Asp Ile Cys Thr Asp
        275                 280                 285

Tyr Ser Ala Leu Lys Ser Ile Val Met Ser Ser Pro Asn Asp Ile Val
    290                 295                 300

Lys Met Pro Ile Asn Glu Pro Ala His Gly Lys Lys Gln Ser Gln Ile
305                 310                 315                 320

Glu Glu Tyr Val Asp Phe Tyr Asp Gly Ala Gly Val Gln His Ile Ala
                325                 330                 335

Leu Leu Thr Asp Asp Ile Ile Ser Ala Ile Thr Asn Leu Lys Ala Arg
            340                 345                 350

Gly Val Glu Phe Ile Lys Val Pro Pro Thr Tyr Tyr Asp Asn Met Trp
        355                 360                 365

Met Arg Leu Lys Lys Ala Gly Met Met Pro Lys Glu Ala Trp Glu Asp
    370                 375                 380

Ile Lys Lys Leu Asp Ile Leu Ile Asp Phe Asp Glu Gly Gly Tyr Leu
385                 390                 395                 400

Leu Gln Leu Phe Thr Lys His Leu Met Asp Arg Pro Thr Val Phe Ile
                405                 410                 415

Glu Ile Ile Gln Arg Asn Asn Phe Ser Gly Phe Gly Ala Gly Asn Phe
            420                 425                 430

Lys Ser Leu Phe Glu Ala Ile Glu Arg Glu Gln Ala Leu Arg Gly Asn
        435                 440                 445

Leu Ile
    450

<210> SEQ ID NO 112
<211> LENGTH: 408
<212> TYPE: PRT
<213> ORGANISM: Artificial Sequence
<220> FEATURE:
<223> OTHER INFORMATION: Talaromyces HPPD wherein aa 1-30 are
      substituted w aa 1-22 of Arabidopsis thaliana

<400> SEQUENCE: 112

Met Gly His Gln Asn Ala Ala Val Ser Glu Asn Gln Asn His Asp Asp
1               5                   10                  15

Gly Ala Ala Ser Ser Pro Val His Trp Tyr Val Gly Asn Ala Lys Gln
            20                  25                  30

Ala Ala Thr Phe Tyr Ile Thr Arg Met Gly Phe Ser Arg Val Ala Tyr
        35                  40                  45

Arg Gly Leu Glu Thr Gly Ser Arg Ser Val Cys Ser His Val Val Arg
    50                  55                  60

Asn Gly Gly Ile Thr Phe Val Leu Thr Ser Pro Leu Arg Ser Pro Tyr
65                  70                  75                  80

Asn Thr Glu Lys Leu Glu Arg Leu Leu Pro Ser Ala Glu Glu Arg Glu
                85                  90                  95
```

Tyr Leu Lys Glu Ile His Glu His Leu Ala Arg His Gly Asp Ala Val
		            100                 105                 110

Lys Asp Val Ala Phe Glu Val Asp Ser Val Asp Val Phe Ala Ala
            115                 120                 125

Ala Val Gln Asn Gly Ala Val Ala Val Ser Gln Pro Lys Thr Val Glu
            130                 135                 140

Asp Glu Asn Gly Gln Val Arg Val Ala Thr Ile Arg Thr Tyr Gly Asp
145                 150                 155                 160

Thr Thr His Thr Leu Ile Gln Arg Arg Gly Val Glu Lys Pro Tyr Ser
                165                 170                 175

Gly Val Phe Leu Pro Gly Tyr Arg Asp Glu Thr Thr Ser Gly Ser Ser
                180                 185                 190

Asp Pro Ile Thr Ala Phe Leu Pro Lys Val Asp Leu Arg Arg Ile Asp
                195                 200                 205

His Cys Val Gly Asn Gln Asp Trp Asp Glu Met Glu Lys Val Cys Ala
                210                 215                 220

Tyr Tyr Glu Lys Val Leu Gly Phe His Arg Phe Arg Ser Val Asp Asp
225                 230                 235                 240

Lys Asp Ile Cys Thr Asp Tyr Ser Ala Leu Lys Ser Ile Val Met Ser
                245                 250                 255

Ser Pro Asn Asp Ile Val Lys Met Pro Ile Asn Glu Pro Ala His Gly
                260                 265                 270

Lys Lys Gln Ser Gln Ile Glu Glu Tyr Val Asp Phe Tyr Asp Gly Ala
                275                 280                 285

Gly Val Gln His Ile Ala Leu Leu Thr Asp Asp Ile Ile Ser Ala Ile
                290                 295                 300

Thr Asn Leu Lys Ala Arg Gly Val Glu Phe Ile Lys Val Pro Pro Thr
305                 310                 315                 320

Tyr Tyr Asp Asn Met Trp Met Arg Leu Lys Lys Ala Gly Met Met Pro
                325                 330                 335

Lys Glu Ala Trp Glu Asp Ile Lys Lys Leu Asp Ile Leu Ile Asp Phe
                340                 345                 350

Asp Glu Gly Gly Tyr Leu Leu Gln Leu Phe Thr Lys His Leu Met Asp
                355                 360                 365

Arg Pro Thr Val Phe Ile Glu Ile Ile Gln Arg Asn Asn Phe Ser Gly
                370                 375                 380

Phe Gly Ala Gly Asn Phe Lys Ser Leu Phe Glu Ala Ile Glu Arg Glu
385                 390                 395                 400

Gln Ala Leu Arg Gly Asn Leu Ile
                405

<210> SEQ ID NO 113
<211> LENGTH: 435
<212> TYPE: PRT
<213> ORGANISM: Artificial Sequence
<220> FEATURE:
<223> OTHER INFORMATION: Talaromyces HPPD wherein aa 1-30 are
      substituted w aa 1-49 of Arabidopsis thaliana

<400> SEQUENCE: 113

Met Gly His Gln Asn Ala Ala Val Ser Glu Asn Gln Asn His Asp Asp
1               5                   10                  15

Gly Ala Ala Ser Ser Pro Gly Phe Lys Leu Val Gly Phe Ser Lys Phe
                20                  25                  30

Val Arg Lys Asn Pro Lys Ser Asp Lys Phe Lys Val Lys Arg Phe His

```
            35                  40                  45
His Val His Trp Tyr Val Gly Asn Ala Lys Gln Ala Ala Thr Phe Tyr
 50                  55                  60

Ile Thr Arg Met Gly Phe Ser Arg Val Ala Tyr Arg Gly Leu Glu Thr
 65                  70                  75                  80

Gly Ser Arg Ser Val Cys Ser His Val Val Arg Asn Gly Gly Ile Thr
                 85                  90                  95

Phe Val Leu Thr Ser Pro Leu Arg Ser Pro Tyr Asn Thr Glu Lys Leu
                100                 105                 110

Glu Arg Leu Leu Pro Ser Ala Glu Glu Arg Glu Tyr Leu Lys Glu Ile
            115                 120                 125

His Glu His Leu Ala Arg His Gly Asp Ala Val Lys Asp Val Ala Phe
130                 135                 140

Glu Val Asp Ser Val Asp Asp Val Phe Ala Ala Val Gln Asn Gly
145                 150                 155                 160

Ala Val Ala Val Ser Gln Pro Lys Thr Val Glu Asp Glu Asn Gly Gln
                165                 170                 175

Val Arg Val Ala Thr Ile Arg Thr Tyr Gly Asp Thr Thr His Thr Leu
            180                 185                 190

Ile Gln Arg Arg Gly Val Glu Lys Pro Tyr Ser Gly Val Phe Leu Pro
            195                 200                 205

Gly Tyr Arg Asp Glu Thr Thr Ser Gly Ser Ser Asp Pro Ile Thr Ala
210                 215                 220

Phe Leu Pro Lys Val Asp Leu Arg Arg Ile Asp His Cys Val Gly Asn
225                 230                 235                 240

Gln Asp Trp Asp Glu Met Glu Lys Val Cys Ala Tyr Tyr Glu Lys Val
                245                 250                 255

Leu Gly Phe His Arg Phe Arg Ser Val Asp Asp Lys Asp Ile Cys Thr
            260                 265                 270

Asp Tyr Ser Ala Leu Lys Ser Ile Val Met Ser Ser Pro Asn Asp Ile
            275                 280                 285

Val Lys Met Pro Ile Asn Glu Pro Ala His Gly Lys Lys Gln Ser Gln
290                 295                 300

Ile Glu Glu Tyr Val Asp Phe Tyr Asp Gly Ala Gly Val Gln His Ile
305                 310                 315                 320

Ala Leu Leu Thr Asp Asp Ile Ile Ser Ala Ile Thr Asn Leu Lys Ala
                325                 330                 335

Arg Gly Val Glu Phe Ile Lys Val Pro Pro Thr Tyr Tyr Asp Asn Met
            340                 345                 350

Trp Met Arg Leu Lys Lys Ala Gly Met Met Pro Lys Glu Ala Trp Glu
            355                 360                 365

Asp Ile Lys Lys Leu Asp Leu Ile Asp Phe Asp Glu Gly Gly Tyr
370                 375                 380

Leu Leu Gln Leu Phe Thr Lys His Leu Met Asp Arg Pro Thr Val Phe
385                 390                 395                 400

Ile Glu Ile Ile Gln Arg Asn Asn Phe Ser Gly Phe Gly Ala Gly Asn
                405                 410                 415

Phe Lys Ser Leu Phe Glu Ala Ile Glu Arg Glu Gln Ala Leu Arg Gly
            420                 425                 430

Asn Leu Ile
        435

<210> SEQ ID NO 114
```

<211> LENGTH: 437
<212> TYPE: PRT
<213> ORGANISM: Artificial Sequence
<220> FEATURE:
<223> OTHER INFORMATION: Trichoderma HPPD + aa 1-22 of Arabidopsis
    thaliana at N'

<400> SEQUENCE: 114

```
Met Gly His Gln Asn Ala Ala Val Ser Glu Asn Gln Asn His Asp Asp
1               5                   10                  15

Gly Ala Ala Ser Ser Pro Met Ser Pro Ser Ala Ile Ser Asn Ser Pro
            20                  25                  30

Glu Gln Arg Pro Ala Asn Asn Asn Gly Thr Thr Pro Asp Asn Phe Ala
        35                  40                  45

Ile Gln Pro Pro Ala Asp Phe Thr Gly Tyr Asp His Val Thr Trp Trp
50                  55                  60

Val Gly Asn Ala Lys Gln Ala Ala Ala Tyr Tyr Thr Thr Leu Phe Gly
65                  70                  75                  80

Phe Glu Thr Thr Ala Tyr Arg Gly Leu Glu Thr Gly Ser Arg Tyr Phe
                85                  90                  95

Ala Ser Tyr Val Val Cys Asn Asn Gly Val Arg Phe Val Phe Thr Ser
            100                 105                 110

Pro Leu Arg Ser Glu Ala His Leu Pro Glu Asp Glu Thr Ile Ser Asp
        115                 120                 125

Ser Glu Arg Lys Leu Leu Lys Glu Ile His Ala His Leu Glu Arg His
130                 135                 140

Gly Asp Ala Val Lys Asp Val Ala Phe Glu Val Asp Asn Val Glu Ala
145                 150                 155                 160

Val Tyr Asn Lys Ala Val Ala Glu Gly Ala Ile Ala Val Gln Gly Pro
                165                 170                 175

Thr Ala Thr Lys Asp Asp His Gly Ser Val Thr Thr Ala Val Ile Cys
            180                 185                 190

Thr Tyr Gly Asp Thr Thr His Thr Leu Ile Asn Arg Arg Gly Tyr Thr
        195                 200                 205

Gly Pro Phe Leu Pro Gly Phe Arg Ala Gly Lys Glu Arg Thr Ser Ser
210                 215                 220

Val Glu Met Pro Asn Val Pro Leu Ala Arg Ile Asp His Cys Val Gly
225                 230                 235                 240

Asn Gln Ser Trp Asn Glu Met Val Ser Ala Cys Ala Phe Tyr Glu Gln
                245                 250                 255

Cys Leu Ser Phe His Arg Phe Trp Ser Val Asp Asp Ser Gln Ile Cys
            260                 265                 270

Thr Glu Phe Ser Ala Leu Asn Ser Ile Val Met Ala Ser Pro Asn Asn
        275                 280                 285

Leu Val Lys Met Pro Ile Asn Glu Pro Ala Pro Gly Lys Lys Lys Ser
290                 295                 300

Gln Ile Glu Glu Tyr Val Ile Phe Asn Ser Gly Pro Gly Val Gln His
305                 310                 315                 320

Ile Ala Leu Leu Thr Pro Asp Ile Ile Thr Ser Val Ser Ala Leu Arg
                325                 330                 335

Ala Arg Gly Val Glu Phe Ile Asn Val Pro Thr Thr Tyr Tyr Asp Thr
            340                 345                 350

Met Arg Gln Arg Leu Lys Thr Glu Lys Arg Asn Trp Gln Leu Lys Glu
        355                 360                 365

Asp Leu Asp Thr Ile Gln Arg Leu Asn Ile Leu Ile Asp Tyr Asp Glu
```

-continued

```
            370                 375                 380
Ala Gly Tyr Leu Leu Gln Leu Phe Thr Lys Pro Leu Met Asp Arg Pro
385                 390                 395                 400

Thr Val Phe Ile Glu Ile Ile Gln Arg Asn Asn Phe Glu Gly Phe Gly
                405                 410                 415

Ala Gly Asn Phe Lys Ser Leu Phe Glu Ala Ile Glu Arg Glu Gln Ala
                420                 425                 430

Glu Arg Gly Asn Leu
            435

<210> SEQ ID NO 115
<211> LENGTH: 464
<212> TYPE: PRT
<213> ORGANISM: Artificial Sequence
<220> FEATURE:
<223> OTHER INFORMATION: Trichoderma HPPD + aa 1-49 of Arabidopsis
      thaliana at N'

<400> SEQUENCE: 115

Met Gly His Gln Asn Ala Ala Val Ser Glu Asn Gln Asn His Asp Asp
1               5                   10                  15

Gly Ala Ala Ser Ser Pro Gly Phe Lys Leu Val Gly Phe Ser Lys Phe
                20                  25                  30

Val Arg Lys Asn Pro Lys Ser Asp Lys Phe Lys Val Lys Arg Phe His
            35                  40                  45

His Met Ser Pro Ser Ala Ile Ser Asn Ser Pro Glu Gln Arg Pro Ala
        50                  55                  60

Asn Asn Asn Gly Thr Thr Pro Asp Asn Phe Ala Ile Gln Pro Pro Ala
65                  70                  75                  80

Asp Phe Thr Gly Tyr Asp His Val Thr Trp Trp Val Gly Asn Ala Lys
                85                  90                  95

Gln Ala Ala Ala Tyr Tyr Thr Thr Leu Phe Gly Phe Glu Thr Thr Ala
                100                 105                 110

Tyr Arg Gly Leu Glu Thr Gly Ser Arg Tyr Phe Ala Ser Tyr Val Val
            115                 120                 125

Cys Asn Asn Gly Val Arg Phe Val Phe Thr Ser Pro Leu Arg Ser Glu
130                 135                 140

Ala His Leu Pro Glu Asp Glu Thr Ile Ser Asp Ser Glu Arg Lys Leu
145                 150                 155                 160

Leu Lys Glu Ile His Ala His Leu Glu Arg His Gly Asp Ala Val Lys
                165                 170                 175

Asp Val Ala Phe Glu Val Asp Asn Val Glu Ala Val Tyr Asn Lys Ala
            180                 185                 190

Val Ala Glu Gly Ala Ile Ala Val Gln Gly Pro Thr Ala Thr Lys Asp
        195                 200                 205

Asp His Gly Ser Val Thr Thr Ala Val Ile Cys Thr Tyr Gly Asp Thr
    210                 215                 220

Thr His Thr Leu Ile Asn Arg Arg Gly Tyr Thr Gly Pro Phe Leu Pro
225                 230                 235                 240

Gly Phe Arg Ala Gly Lys Glu Arg Thr Ser Ser Val Glu Met Pro Asn
                245                 250                 255

Val Pro Leu Ala Arg Ile Asp His Cys Val Gly Asn Gln Ser Trp Asn
            260                 265                 270

Glu Met Val Ser Ala Cys Ala Phe Tyr Glu Gln Cys Leu Ser Phe His
        275                 280                 285
```

```
Arg Phe Trp Ser Val Asp Asp Ser Gln Ile Cys Thr Glu Phe Ser Ala
    290             295                 300

Leu Asn Ser Ile Val Met Ala Ser Pro Asn Asn Leu Val Lys Met Pro
305             310                 315                 320

Ile Asn Glu Pro Ala Pro Gly Lys Lys Ser Gln Ile Glu Glu Tyr
                325                 330                 335

Val Ile Phe Asn Ser Gly Pro Gly Val Gln His Ile Ala Leu Leu Thr
            340             345                 350

Pro Asp Ile Ile Thr Ser Val Ser Ala Leu Arg Ala Arg Gly Val Glu
            355             360                 365

Phe Ile Asn Val Pro Thr Thr Tyr Tyr Asp Thr Met Arg Gln Arg Leu
370             375                 380

Lys Thr Glu Lys Arg Asn Trp Gln Leu Lys Glu Asp Leu Asp Thr Ile
385             390                 395                 400

Gln Arg Leu Asn Ile Leu Ile Asp Tyr Asp Glu Ala Gly Tyr Leu Leu
                405                 410                 415

Gln Leu Phe Thr Lys Pro Leu Met Asp Arg Pro Thr Val Phe Ile Glu
            420                 425                 430

Ile Ile Gln Arg Asn Asn Phe Glu Gly Phe Gly Ala Gly Asn Phe Lys
            435                 440                 445

Ser Leu Phe Glu Ala Ile Glu Arg Glu Gln Ala Glu Arg Gly Asn Leu
450                 455                 460

<210> SEQ ID NO 116
<211> LENGTH: 437
<212> TYPE: PRT
<213> ORGANISM: Artificial Sequence
<220> FEATURE:
<223> OTHER INFORMATION: Talaromyces HPPD + aa 1-22 of Arabidopsis
      thaliana at N'

<400> SEQUENCE: 116

Met Gly His Gln Asn Ala Ala Val Ser Glu Asn Gln Asn His Asp Asp
1               5                   10                  15

Gly Ala Ala Ser Ser Pro Met Ala Pro Ser Ala Ile Ser Asp Leu Gln
            20                  25                  30

Ser Asp Asn Leu Pro Thr Thr Gln Ser Ala Leu Ser Ser Tyr Arg Gly
        35                  40                  45

Tyr Asp His Val His Trp Tyr Val Gly Asn Ala Lys Gln Ala Ala Thr
50                  55                  60

Phe Tyr Ile Thr Arg Met Gly Phe Ser Arg Val Ala Tyr Arg Gly Leu
65                  70                  75                  80

Glu Thr Gly Ser Arg Ser Val Cys Ser His Val Val Arg Asn Gly Gly
                85                  90                  95

Ile Thr Phe Val Leu Thr Ser Pro Leu Arg Ser Pro Tyr Asn Thr Glu
            100                 105                 110

Lys Leu Glu Arg Leu Leu Pro Ser Ala Glu Glu Arg Glu Tyr Leu Lys
        115                 120                 125

Glu Ile His Glu His Leu Ala Arg His Gly Asp Ala Val Lys Asp Val
130                 135                 140

Ala Phe Glu Val Asp Ser Val Asp Val Phe Ala Ala Val Gln
145                 150                 155             160

Asn Gly Ala Val Ala Val Ser Gln Pro Lys Thr Val Glu Asp Glu Asn
                165                 170                 175

Gly Gln Val Arg Val Ala Thr Ile Arg Thr Tyr Gly Asp Thr Thr His
            180                 185                 190
```

```
Thr Leu Ile Gln Arg Arg Gly Val Glu Lys Pro Tyr Ser Gly Val Phe
            195                 200                 205

Leu Pro Gly Tyr Arg Asp Glu Thr Thr Ser Gly Ser Ser Asp Pro Ile
    210                 215                 220

Thr Ala Phe Leu Pro Lys Val Asp Leu Arg Arg Ile Asp His Cys Val
225                 230                 235                 240

Gly Asn Gln Asp Trp Asp Glu Met Glu Lys Val Cys Ala Tyr Tyr Glu
                245                 250                 255

Lys Val Leu Gly Phe His Arg Phe Arg Ser Val Asp Asp Lys Asp Ile
            260                 265                 270

Cys Thr Asp Tyr Ser Ala Leu Lys Ser Ile Val Met Ser Ser Pro Asn
            275                 280                 285

Asp Ile Val Lys Met Pro Ile Asn Glu Pro Ala His Gly Lys Lys Gln
            290                 295                 300

Ser Gln Ile Glu Glu Tyr Val Asp Phe Tyr Asp Gly Ala Gly Val Gln
305                 310                 315                 320

His Ile Ala Leu Leu Thr Asp Asp Ile Ile Ser Ala Ile Thr Asn Leu
                325                 330                 335

Lys Ala Arg Gly Val Glu Phe Ile Lys Val Pro Pro Thr Tyr Tyr Asp
            340                 345                 350

Asn Met Trp Met Arg Leu Lys Lys Ala Gly Met Met Pro Lys Glu Ala
            355                 360                 365

Trp Glu Asp Ile Lys Lys Leu Asp Ile Leu Ile Asp Phe Asp Glu Gly
            370                 375                 380

Gly Tyr Leu Leu Gln Leu Phe Thr Lys His Leu Met Asp Arg Pro Thr
385                 390                 395                 400

Val Phe Ile Glu Ile Ile Gln Arg Asn Asn Phe Ser Gly Phe Gly Ala
                405                 410                 415

Gly Asn Phe Lys Ser Leu Phe Glu Ala Ile Glu Arg Glu Gln Ala Leu
            420                 425                 430

Arg Gly Asn Leu Ile
        435

<210> SEQ ID NO 117
<211> LENGTH: 464
<212> TYPE: PRT
<213> ORGANISM: Artificial Sequence
<220> FEATURE:
<223> OTHER INFORMATION: Talaromyces HPPD + aa 1-49 of Arabidopsis
      thaliana at N'

<400> SEQUENCE: 117

Met Gly His Gln Asn Ala Ala Val Ser Glu Asn Gln Asn His Asp Asp
1               5                   10                  15

Gly Ala Ala Ser Ser Pro Gly Phe Lys Leu Val Gly Phe Ser Lys Phe
            20                  25                  30

Val Arg Lys Asn Pro Lys Ser Asp Lys Phe Lys Val Lys Arg Phe His
            35                  40                  45

His Met Ala Pro Ser Ala Ile Ser Asp Leu Gln Ser Asp Asn Leu Pro
        50                  55                  60

Thr Thr Gln Ser Ala Leu Ser Ser Tyr Arg Gly Tyr Asp His Val His
65                  70                  75                  80

Trp Tyr Val Gly Asn Ala Lys Gln Ala Ala Thr Phe Tyr Ile Thr Arg
                85                  90                  95

Met Gly Phe Ser Arg Val Ala Tyr Arg Gly Leu Glu Thr Gly Ser Arg
```

```
            100                 105                 110
Ser Val Cys Ser His Val Val Arg Asn Gly Gly Ile Thr Phe Val Leu
            115                 120                 125

Thr Ser Pro Leu Arg Ser Pro Tyr Asn Thr Glu Lys Leu Glu Arg Leu
    130                 135                 140

Leu Pro Ser Ala Glu Arg Glu Tyr Leu Lys Glu Ile His Glu His
145                 150                 155                 160

Leu Ala Arg His Gly Asp Ala Val Lys Asp Val Ala Phe Glu Val Asp
                165                 170                 175

Ser Val Asp Asp Val Phe Ala Ala Val Gln Asn Gly Ala Val Ala
                180                 185                 190

Val Ser Gln Pro Lys Thr Val Glu Asp Glu Asn Gly Gln Val Arg Val
            195                 200                 205

Ala Thr Ile Arg Thr Tyr Gly Asp Thr Thr His Thr Leu Ile Gln Arg
210                 215                 220

Arg Gly Val Glu Lys Pro Tyr Ser Gly Val Phe Leu Pro Gly Tyr Arg
225                 230                 235                 240

Asp Glu Thr Thr Ser Gly Ser Ser Asp Pro Ile Thr Ala Phe Leu Pro
                245                 250                 255

Lys Val Asp Leu Arg Arg Ile Asp His Cys Val Gly Asn Gln Asp Trp
                260                 265                 270

Asp Glu Met Glu Lys Val Cys Ala Tyr Tyr Glu Lys Val Leu Gly Phe
            275                 280                 285

His Arg Phe Arg Ser Val Asp Asp Lys Asp Ile Cys Thr Asp Tyr Ser
    290                 295                 300

Ala Leu Lys Ser Ile Val Met Ser Ser Pro Asn Asp Ile Val Lys Met
305                 310                 315                 320

Pro Ile Asn Glu Pro Ala His Gly Lys Lys Gln Ser Gln Ile Glu Glu
                325                 330                 335

Tyr Val Asp Phe Tyr Asp Gly Ala Gly Val Gln His Ile Ala Leu Leu
                340                 345                 350

Thr Asp Asp Ile Ile Ser Ala Ile Thr Asn Leu Lys Ala Arg Gly Val
            355                 360                 365

Glu Phe Ile Lys Val Pro Pro Thr Tyr Tyr Asp Asn Met Trp Met Arg
370                 375                 380

Leu Lys Lys Ala Gly Met Met Pro Lys Glu Ala Trp Glu Asp Ile Lys
385                 390                 395                 400

Lys Leu Asp Ile Leu Ile Asp Phe Asp Glu Gly Gly Tyr Leu Leu Gln
                405                 410                 415

Leu Phe Thr Lys His Leu Met Asp Arg Pro Thr Val Phe Ile Glu Ile
            420                 425                 430

Ile Gln Arg Asn Asn Phe Ser Gly Phe Gly Ala Gly Asn Phe Lys Ser
            435                 440                 445

Leu Phe Glu Ala Ile Glu Arg Glu Gln Ala Leu Arg Gly Asn Leu Ile
450                 455                 460
```

<210> SEQ ID NO 118
<211> LENGTH: 446
<212> TYPE: PRT
<213> ORGANISM: Glycine max
<220> FEATURE:
<221> NAME/KEY: MISC_FEATURE
<222> LOCATION: (396)..(396)
<223> OTHER INFORMATION: X = any amino acid

<400> SEQUENCE: 118

```
Met Pro Ile Pro Cys Asn Glu Ile Gln Ala Gln Ala Gln Ala
1               5                   10                  15

Gln Pro Gly Phe Lys Leu Val Gly Phe Lys Asn Phe Val Arg Thr Asn
            20                  25                  30

Pro Lys Ser Asp Arg Phe Gln Val Asn Arg Phe His His Ile Glu Phe
        35                  40                  45

Trp Cys Thr Asp Ala Thr Asn Ala Ser Arg Arg Phe Ser Trp Gly Leu
    50                  55                  60

Gly Met Pro Ile Val Ala Lys Ser Asp Leu Ser Thr Gly Asn Gln Ile
65                  70                  75                  80

His Ala Ser Tyr Leu Leu Arg Ser Gly Asp Leu Ser Phe Leu Phe Ser
                85                  90                  95

Ala Pro Tyr Ser Pro Ser Leu Ser Ala Gly Ser Ser Ala Ala Ser Ser
            100                 105                 110

Ala Ser Ile Pro Ser Phe Asp Ala Ala Thr Cys Leu Ala Phe Ala Ala
        115                 120                 125

Lys His Gly Phe Gly Val Arg Ala Ile Ala Leu Glu Val Ala Asp Ala
    130                 135                 140

Glu Ala Ala Phe Ser Ala Ser Val Ala Lys Gly Ala Glu Pro Ala Ser
145                 150                 155                 160

Pro Pro Val Leu Val Asp Asp Arg Thr Gly Phe Ala Glu Val Arg Leu
            165                 170                 175

Tyr Gly Asp Val Val Leu Arg Tyr Val Ser Tyr Lys Asp Ala Ala Pro
        180                 185                 190

Gln Ala Pro His Ala Asp Pro Ser Arg Trp Phe Leu Pro Gly Phe Glu
    195                 200                 205

Ala Ala Ala Ser Ser Ser Ser Phe Pro Glu Leu Asp Tyr Gly Ile Arg
210                 215                 220

Arg Leu Asp His Ala Val Gly Asn Val Pro Glu Leu Ala Pro Ala Val
225                 230                 235                 240

Arg Tyr Leu Lys Gly Phe Ser Gly Phe His Glu Phe Ala Glu Phe Thr
            245                 250                 255

Ala Glu Asp Val Gly Thr Ser Glu Ser Gly Leu Asn Ser Val Val Leu
        260                 265                 270

Ala Asn Asn Ser Glu Thr Val Leu Leu Pro Leu Asn Glu Pro Val Tyr
    275                 280                 285

Gly Thr Lys Arg Lys Ser Gln Ile Glu Thr Tyr Leu Glu His Asn Glu
290                 295                 300

Gly Ala Gly Val Gln His Leu Ala Leu Val Thr His Asp Ile Phe Thr
305                 310                 315                 320

Thr Leu Arg Glu Met Arg Lys Arg Ser Phe Leu Gly Gly Phe Glu Phe
            325                 330                 335

Met Pro Ser Pro Pro Thr Tyr Tyr Ala Asn Leu His Asn Arg Ala
        340                 345                 350

Ala Asp Val Leu Thr Val Asp Gln Ile Lys Gln Cys Glu Glu Leu Gly
    355                 360                 365

Ile Leu Val Asp Arg Asp Asp Gln Gly Thr Leu Leu Gln Ile Phe Thr
370                 375                 380

Lys Pro Val Gly Asp Arg Pro Thr Ile Phe Ile Xaa Ile Ile Gln Arg
385                 390                 395                 400

Ile Gly Cys Met Val Glu Asp Glu Glu Gly Lys Val Tyr Gln Lys Gly
            405                 410                 415
```

```
Ala Cys Gly Gly Phe Gly Lys Gly Asn Phe Ser Glu Leu Phe Lys Ser
                420                 425                 430

Ile Glu Glu Tyr Glu Lys Thr Leu Glu Ala Lys Arg Thr Ala
        435                 440                 445

<210> SEQ ID NO 119
<211> LENGTH: 12
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (1)..(1)
<223> OTHER INFORMATION: X= E or R
<220> FEATURE:
<221> NAME/KEY: MISC_FEATURE
<222> LOCATION: (2)..(2)
<223> OTHER INFORMATION: X= any amino acid
<220> FEATURE:
<221> NAME/KEY: MISC_FEATURE
<222> LOCATION: (5)..(5)
<223> OTHER INFORMATION: X= S or T
<220> FEATURE:
<221> NAME/KEY: MISC_FEATURE
<222> LOCATION: (6)..(6)
<223> OTHER INFORMATION: X= A, I or T
<220> FEATURE:
<221> NAME/KEY: MISC_FEATURE
<222> LOCATION: (9)..(9)
<223> OTHER INFORMATION: X= any amino acid
<220> FEATURE:
<221> NAME/KEY: MISC_FEATURE
<222> LOCATION: (10)..(10)
<223> OTHER INFORMATION: X= K, N or H

<400> SEQUENCE: 119

Xaa Xaa Ala Tyr Xaa Xaa Ser Val Xaa Xaa Gly Ala
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (1)..(1)
<223> OTHER INFORMATION: X = E or R
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (6)..(6)
<223> OTHER INFORMATION: X = A, I or T
<220> FEATURE:
<221> NAME/KEY: MISC_FEATURE
<222> LOCATION: (9)..(9)
<223> OTHER INFORMATION: X = any amino acid
<220> FEATURE:
<221> NAME/KEY: MISC_FEATURE
<222> LOCATION: (10)..(10)
<223> OTHER INFORMATION: X = K, N or H

<400> SEQUENCE: 120

Xaa Xaa Ala Phe Asn Xaa Ser Val Xaa Xaa Gly Ala
1               5                   10

<210> SEQ ID NO 121
<211> LENGTH: 12
```

```
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (1)..(1)
<223> OTHER INFORMATION: X= E or R
<220> FEATURE:
<221> NAME/KEY: MISC_FEATURE
<222> LOCATION: (2)..(2)
<223> OTHER INFORMATION: X= any amino acid
<220> FEATURE:
<221> NAME/KEY: MISC_FEATURE
<222> LOCATION: (5)..(5)
<223> OTHER INFORMATION: X= S or T
<220> FEATURE:
<221> NAME/KEY: MISC_FEATURE
<222> LOCATION: (9)..(9)
<223> OTHER INFORMATION: X= any amino acid
<220> FEATURE:
<221> NAME/KEY: MISC_FEATURE
<222> LOCATION: (10)..(10)
<223> OTHER INFORMATION: X= K, N, H

<400> SEQUENCE: 121

Xaa Xaa Ala Phe Xaa Lys Ser Val Xaa Xaa Gly Ala
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (1)..(1)
<223> OTHER INFORMATION: X = E or R
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (5)..(5)
<223> OTHER INFORMATION: X = S or T
<220> FEATURE:
<221> NAME/KEY: MISC_FEATURE
<222> LOCATION: (6)..(6)
<223> OTHER INFORMATION: X = A, I or T
<220> FEATURE:
<221> NAME/KEY: MISC_FEATURE
<222> LOCATION: (9)..(9)
<223> OTHER INFORMATION: X = any amino acid
<220> FEATURE:
<221> NAME/KEY: MISC_FEATURE
<222> LOCATION: (10)..(10)
<223> OTHER INFORMATION: X = K, N or H

<400> SEQUENCE: 122

Xaa Xaa Ala Phe Xaa Xaa Ala Val Xaa Xaa Gly Ala
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (1)..(1)
<223> OTHER INFORMATION: X = E or R
<220> FEATURE:
```

```
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (5)..(5)
<223> OTHER INFORMATION: X = S or T
<220> FEATURE:
<221> NAME/KEY: MISC_FEATURE
<222> LOCATION: (6)..(6)
<223> OTHER INFORMATION: X = A, I or T
<220> FEATURE:
<221> NAME/KEY: MISC_FEATURE
<222> LOCATION: (9)..(9)
<223> OTHER INFORMATION: X = any amino acid

<400> SEQUENCE: 123

Xaa Xaa Ala Phe Xaa Xaa Ser Val Xaa Glu Gly Ala
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (8)..(8)
<223> OTHER INFORMATION: X = A or S
<220> FEATURE:
<221> NAME/KEY: MISC_FEATURE
<222> LOCATION: (10)..(10)
<223> OTHER INFORMATION: X = P or E

<400> SEQUENCE: 124

Val Xaa Glu Gly Ala Glu Pro Xaa Ser Xaa Pro
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = K, N or H
<220> FEATURE:
<221> NAME/KEY: MISC_FEATURE
<222> LOCATION: (8)..(8)
<223> OTHER INFORMATION: X = A or S
<220> FEATURE:
<221> NAME/KEY: MISC_FEATURE
<222> LOCATION: (10)..(10)
<223> OTHER INFORMATION: X = P or E

<400> SEQUENCE: 125

Val Xaa Xaa Gly Ala Ile Pro Xaa Ser Xaa Pro
1               5                   10

<210> SEQ ID NO 126
<211> LENGTH: 11
<212> TYPE: PRT
```

```
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = K, N or H
<220> FEATURE:
<221> NAME/KEY: MISC_FEATURE
<222> LOCATION: (8)..(8)
<223> OTHER INFORMATION: X = A or S
<220> FEATURE:
<221> NAME/KEY: MISC_FEATURE
<222> LOCATION: (10)..(10)
<223> OTHER INFORMATION: X = P or E

<400> SEQUENCE: 126

Val Xaa Xaa Gly Ala Glu Ala Xaa Ser Xaa Pro
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = K, N or H
<220> FEATURE:
<221> NAME/KEY: MISC_FEATURE
<222> LOCATION: (8)..(8)
<223> OTHER INFORMATION: X = A or S
<220> FEATURE:
<221> NAME/KEY: MISC_FEATURE
<222> LOCATION: (10)..(10)
<223> OTHER INFORMATION: X = P or E

<400> SEQUENCE: 127

Val Xaa Xaa Gly Ala Glu Pro Xaa Gln Xaa Pro
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (3)..(3)
<223> OTHER INFORMATION: X = K, N or H
<220> FEATURE:
<221> NAME/KEY: MISC_FEATURE
<222> LOCATION: (8)..(8)
<223> OTHER INFORMATION: X = A or S

<400> SEQUENCE: 128

Val Xaa Xaa Gly Ala Glu Pro Xaa Ser Gly Pro
1               5                   10
```

```
<210> SEQ ID NO 129
<211> LENGTH: 9
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (3)..(3)
<223> OTHER INFORMATION: X = E or Q
<220> FEATURE:
<221> NAME/KEY: MISC_FEATURE
<222> LOCATION: (5)..(5)
<223> OTHER INFORMATION: X = W or R
<220> FEATURE:
<221> NAME/KEY: MISC_FEATURE
<222> LOCATION: (9)..(9)
<223> OTHER INFORMATION: X = A or T

<400> SEQUENCE: 129

Phe His Xaa Phe Xaa Glu Phe Thr Xaa
1               5

<210> SEQ ID NO 130
<211> LENGTH: 9
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (3)..(3)
<223> OTHER INFORMATION: X = E or Q
<220> FEATURE:
<221> NAME/KEY: MISC_FEATURE
<222> LOCATION: (9)..(9)
<223> OTHER INFORMATION: X = A or T

<400> SEQUENCE: 130

Phe His Xaa Phe Ala Glu Phe Asp Xaa
1               5

<210> SEQ ID NO 131
<211> LENGTH: 9
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (3)..(3)
<223> OTHER INFORMATION: X = E or Q

<400> SEQUENCE: 131

Phe His Xaa Phe Ala Glu Phe Thr Asp
1               5

<210> SEQ ID NO 132
<211> LENGTH: 10
<212> TYPE: PRT
<213> ORGANISM: Artificial Sequence
<220> FEATURE:
<223> OTHER INFORMATION: DXXDVGTXES
<220> FEATURE:
<221> NAME/KEY: MISC_FEATURE
<222> LOCATION: (2)..(2)
<223> OTHER INFORMATION: X = A or T
<220> FEATURE:
<221> NAME/KEY: MISC_FEATURE
<222> LOCATION: (3)..(3)
<223> OTHER INFORMATION: X = E or D
<220> FEATURE:
```

```
<221> NAME/KEY: MISC_FEATURE
<222> LOCATION: (8)..(8)
<223> OTHER INFORMATION: X = A or S

<400> SEQUENCE: 132

Asp Xaa Xaa Asp Val Gly Thr Xaa Glu Ser
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (3)..(3)
<223> OTHER INFORMATION: X = E or D
<220> FEATURE:
<221> NAME/KEY: MISC_FEATURE
<222> LOCATION: (8)..(8)
<223> OTHER INFORMATION: X = A or S

<400> SEQUENCE: 133

Thr Asp Xaa Asp Val Gly Thr Xaa Glu Ser
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (2)..(2)
<223> OTHER INFORMATION: X = A or T
<220> FEATURE:
<221> NAME/KEY: MISC_FEATURE
<222> LOCATION: (3)..(3)
<223> OTHER INFORMATION: X = E or D
<220> FEATURE:
<221> NAME/KEY: MISC_FEATURE
<222> LOCATION: (8)..(8)
<223> OTHER INFORMATION: X = A or S
<220> FEATURE:
<221> NAME/KEY: MISC_FEATURE
<222> LOCATION: (9)..(9)
<223> OTHER INFORMATION: X = F or Y

<400> SEQUENCE: 134

Thr Xaa Xaa Asp Val Gly Thr Xaa Xaa Ser
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (2)..(2)
<223> OTHER INFORMATION: X = E or D
<220> FEATURE:
<221> NAME/KEY: MISC_FEATURE
<222> LOCATION: (9)..(9)
<223> OTHER INFORMATION: X = P or V

<400> SEQUENCE: 135

Phe Xaa Phe Ile Pro Ser Pro Pro Xaa Thr Tyr Tyr
1               5                   10
```

```
<210> SEQ ID NO 136
<211> LENGTH: 12
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (2)..(2)
<223> OTHER INFORMATION: X = E or D
<220> FEATURE:
<221> NAME/KEY: MISC_FEATURE
<222> LOCATION: (9)..(9)
<223> OTHER INFORMATION: X = P or V

<400> SEQUENCE: 136

Phe Xaa Phe Met Asn Ser Pro Pro Xaa Thr Tyr Tyr
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (2)..(2)
<223> OTHER INFORMATION: X = E or D
<220> FEATURE:
<221> NAME/KEY: MISC_FEATURE
<222> LOCATION: (9)..(9)
<223> OTHER INFORMATION: X = P or V

<400> SEQUENCE: 137

Phe Xaa Phe Met Pro Val Pro Pro Xaa Thr Tyr Tyr
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (2)..(2)
<223> OTHER INFORMATION: X = E or D
<220> FEATURE:
<221> NAME/KEY: MISC_FEATURE
<222> LOCATION: (8)..(8)
<223> OTHER INFORMATION: X = G or T
<220> FEATURE:
<221> NAME/KEY: MISC_FEATURE
<222> LOCATION: (9)..(9)
<223> OTHER INFORMATION: X = P or V

<400> SEQUENCE: 138

Phe Xaa Phe Met Pro Ser Pro Xaa Xaa Thr Tyr Tyr
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (2)..(2)
<223> OTHER INFORMATION: X = E or D
```

<400> SEQUENCE: 139

Phe Xaa Phe Met Pro Ser Pro Pro Gly Thr Tyr Tyr
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (2)..(2)
<223> OTHER INFORMATION: X = E or D

<400> SEQUENCE: 140

Phe Xaa Phe Met Pro Ser Pro Pro Thr Tyr Tyr
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (5)..(5)
<223> OTHER INFORMATION: X = N or K
<220> FEATURE:
<221> NAME/KEY: MISC_FEATURE
<222> LOCATION: (7)..(7)
<223> OTHER INFORMATION: X = H, K or R
<220> FEATURE:
<221> NAME/KEY: MISC_FEATURE
<222> LOCATION: (8)..(8)
<223> OTHER INFORMATION: X = any amino acid
<220> FEATURE:
<221> NAME/KEY: MISC_FEATURE
<222> LOCATION: (9)..(9)
<223> OTHER INFORMATION: X = A or G

<400> SEQUENCE: 141

Thr Tyr Tyr Asp Xaa Leu Xaa Xaa Xaa Leu
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (4)..(4)
<223> OTHER INFORMATION: X = any amino acid
<220> FEATURE:
<221> NAME/KEY: MISC_FEATURE
<222> LOCATION: (5)..(5)
<223> OTHER INFORMATION: X = N or K
<220> FEATURE:
<221> NAME/KEY: MISC_FEATURE
<222> LOCATION: (7)..(7)
<223> OTHER INFORMATION: X = H, K or R
<220> FEATURE:
<221> NAME/KEY: MISC_FEATURE
<222> LOCATION: (9)..(9)
<223> OTHER INFORMATION: X = A or G

<400> SEQUENCE: 142

Thr Tyr Tyr Xaa Xaa Leu Xaa Leu Xaa Leu

```
1               5                   10
```

<210> SEQ ID NO 143
<211> LENGTH: 8
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (3)..(3)
<223> OTHER INFORMATION: X = Fo r Y

<400> SEQUENCE: 143

```
Val Asp Xaa Asp Asp Gln Gly Thr
1               5
```

<210> SEQ ID NO 144
<211> LENGTH: 8
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (3)..(3)
<223> OTHER INFORMATION: X = R or K
<220> FEATURE:
<221> NAME/KEY: MISC_FEATURE
<222> LOCATION: (6)..(6)
<223> OTHER INFORMATION: X = A or G

<400> SEQUENCE: 144

```
Val Asp Xaa Asp Asp Xaa Gly Thr
1               5
```

<210> SEQ ID NO 145
<211> LENGTH: 9
<212> TYPE: PRT
<213> ORGANISM: Artificial Sequence
<220> FEATURE:
<223> OTHER INFORMATION: Dicot plant HPPD modified consensus sequence

<400> SEQUENCE: 145

```
Glu Ile Ile Gln Arg Asn Gly Cys Met
1               5
```

<210> SEQ ID NO 146
<211> LENGTH: 9
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (6)..(6)
<223> OTHER INFORMATION: X = I or V

<400> SEQUENCE: 146

```
Glu Ile Ile Gln Arg Xaa Asn Cys Met
1               5
```

<210> SEQ ID NO 147
<211> LENGTH: 9
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE

```
<222> LOCATION: (6)..(6)
<223> OTHER INFORMATION: X = I or V

<400> SEQUENCE: 147

Glu Ile Ile Gln Arg Xaa Gly Phe Met
1               5

<210> SEQ ID NO 148
<211> LENGTH: 9
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (6)..(6)
<223> OTHER INFORMATION: X = I or V

<400> SEQUENCE: 148

Glu Ile Ile Gln Arg Xaa Gly Cys Gly
1               5

<210> SEQ ID NO 149
<211> LENGTH: 8
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (6)..(6)
<223> OTHER INFORMATION: X = I or V

<400> SEQUENCE: 149

Glu Ile Ile Gln Arg Xaa Gly Cys
1               5

<210> SEQ ID NO 150
<211> LENGTH: 9
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (3)..(3)
<223> OTHER INFORMATION: X = any amino acid
<220> FEATURE:
<221> NAME/KEY: MISC_FEATURE
<222> LOCATION: (4)..(4)
<223> OTHER INFORMATION: X = E, K or Q
<220> FEATURE:
<221> NAME/KEY: MISC_FEATURE
<222> LOCATION: (5)..(5)
<223> OTHER INFORMATION: X = X = D or N
<220> FEATURE:
<221> NAME/KEY: MISC_FEATURE
<222> LOCATION: (6)..(6)
<223> OTHER INFORMATION: X = E or A
<220> FEATURE:
<221> NAME/KEY: MISC_FEATURE
<222> LOCATION: (9)..(9)
<223> OTHER INFORMATION: X = K or E

<400> SEQUENCE: 150

Phe Met Xaa Xaa Xaa Xaa Glu Gly Xaa
1               5

<210> SEQ ID NO 151
<211> LENGTH: 10
<212> TYPE: PRT
```

<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (3)..(3)
<223> OTHER INFORMATION: X = K or S
<220> FEATURE:
<221> NAME/KEY: MISC_FEATURE
<222> LOCATION: (5)..(5)
<223> OTHER INFORMATION: X = G or A
<220> FEATURE:
<221> NAME/KEY: MISC_FEATURE
<222> LOCATION: (7)..(7)
<223> OTHER INFORMATION: X = E or S

<400> SEQUENCE: 151

Tyr Gln Xaa Gly Xaa Cys Xaa Gly Phe Gly
1 5 10

<210> SEQ ID NO 152
<211> LENGTH: 9
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (1)..(1)
<223> OTHER INFORMATION: X = A or S
<220> FEATURE:
<221> NAME/KEY: MISC_FEATURE
<222> LOCATION: (2)..(2)
<223> OTHER INFORMATION: X = T or V
<220> FEATURE:
<221> NAME/KEY: MISC_FEATURE
<222> LOCATION: (4)..(4)
<223> OTHER INFORMATION: X = R, H or K

<400> SEQUENCE: 152

Xaa Xaa Val Xaa Leu Tyr Gly Asp Val
1 5

<210> SEQ ID NO 153
<211> LENGTH: 7
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (1)..(1)
<223> OTHER INFORMATION: X = E or Q
<220> FEATURE:
<221> NAME/KEY: MISC_FEATURE
<222> LOCATION: (3)..(3)
<223> OTHER INFORMATION: X = A, G or S
<220> FEATURE:
<221> NAME/KEY: MISC_FEATURE
<222> LOCATION: (4)..(4)
<223> OTHER INFORMATION: X = S or K
<220> FEATURE:
<221> NAME/KEY: MISC_FEATURE
<222> LOCATION: (5)..(5)
<223> OTHER INFORMATION: X = A or V
<220> FEATURE:
<221> NAME/KEY: MISC_FEATURE
<222> LOCATION: (6)..(6)
<223> OTHER INFORMATION: X = V, L or I
<220> FEATURE:
<221> NAME/KEY: MISC_FEATURE
<222> LOCATION: (7)..(7)
<223> OTHER INFORMATION: X = any amino acid

<400> SEQUENCE: 153

```
Xaa Leu Xaa Xaa Xaa Xaa Xaa
1               5

<210> SEQ ID NO 154
<211> LENGTH: 6
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (1)..(1)
<223> OTHER INFORMATION: X = V, L or I
<220> FEATURE:
<221> NAME/KEY: MISC_FEATURE
<222> LOCATION: (2)..(2)
<223> OTHER INFORMATION: X = any amino acid
<220> FEATURE:
<221> NAME/KEY: MISC_FEATURE
<222> LOCATION: (4)..(4)
<223> OTHER INFORMATION: X = L, V or I
<220> FEATURE:
<221> NAME/KEY: MISC_FEATURE
<222> LOCATION: (5)..(5)
<223> OTHER INFORMATION: X = K or A
<220> FEATURE:
<221> NAME/KEY: MISC_FEATURE
<222> LOCATION: (6)..(6)
<223> OTHER INFORMATION: X = any amino acid

<400> SEQUENCE: 154

Xaa Xaa Phe Xaa Xaa Phe
1               5

<210> SEQ ID NO 155
<211> LENGTH: 6
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (2)..(2)
<223> OTHER INFORMATION: X = V or I
<220> FEATURE:
<221> NAME/KEY: MISC_FEATURE
<222> LOCATION: (3)..(3)
<223> OTHER INFORMATION: X = A, D or Q
<220> FEATURE:
<221> NAME/KEY: MISC_FEATURE
<222> LOCATION: (4)..(4)
<223> OTHER INFORMATION: X = any amino acid

<400> SEQUENCE: 155

Phe Xaa Xaa Xaa Asn Pro
1               5

<210> SEQ ID NO 156
<211> LENGTH: 8
<212> TYPE: PRT
<213> ORGANISM: Artificial Sequence
<220> FEATURE:
<223> OTHER INFORMATION: Dicot plant HPPD modified consensus sequence
<220> FEATURE:
<221> NAME/KEY: MISC_FEATURE
<222> LOCATION: (4)..(4)
<223> OTHER INFORMATION: X= N or D

<400> SEQUENCE: 156

Glu Glu Leu Xaa Ile Leu Val Asp
1               5
```

-continued

```
<210> SEQ ID NO 157
<211> LENGTH: 8
<212> TYPE: PRT
<213> ORGANISM: Artificial Sequence
<220> FEATURE:
<223> OTHER INFORMATION: Dicot plant HPPD modified consensus sequence

<400> SEQUENCE: 157

Asp Val Val Leu Arg Phe Val Ser
1               5

<210> SEQ ID NO 158
<211> LENGTH: 7
<212> TYPE: PRT
<213> ORGANISM: Artificial Sequence
<220> FEATURE:
<223> OTHER INFORMATION: Dicot plant HPPD modified consensus sequence

<400> SEQUENCE: 158

Gly Phe Gly Ala Gly Asn Phe
1               5

<210> SEQ ID NO 159
<211> LENGTH: 12
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (1)..(1)
<223> OTHER INFORMATION: X = E or A
<220> FEATURE:
<221> NAME/KEY: MISC_FEATURE
<222> LOCATION: (2)..(2)
<223> OTHER INFORMATION: X = D or E
<220> FEATURE:
<221> NAME/KEY: MISC_FEATURE
<222> LOCATION: (6)..(6)
<223> OTHER INFORMATION: X = A or V
<220> FEATURE:
<221> NAME/KEY: MISC_FEATURE
<222> LOCATION: (10)..(10)
<223> OTHER INFORMATION: X = G or A

<400> SEQUENCE: 159

Xaa Xaa Ala Tyr Arg Xaa Ser Val Ala Xaa Gly Ala
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (1)..(1)
<223> OTHER INFORMATION: X = E or A
<220> FEATURE:
<221> NAME/KEY: MISC_FEATURE
<222> LOCATION: (2)..(2)
<223> OTHER INFORMATION: X = D or E
<220> FEATURE:
<221> NAME/KEY: MISC_FEATURE
<222> LOCATION: (6)..(6)
<223> OTHER INFORMATION: X = A or V
<220> FEATURE:
<221> NAME/KEY: MISC_FEATURE
<222> LOCATION: (10)..(10)
<223> OTHER INFORMATION: X = G or A
```

```
<400> SEQUENCE: 160

Xaa Xaa Ala Phe Asn Xaa Ser Val Ala Xaa Gly Ala
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (1)..(1)
<223> OTHER INFORMATION: X = E or A
<220> FEATURE:
<221> NAME/KEY: MISC_FEATURE
<222> LOCATION: (2)..(2)
<223> OTHER INFORMATION: X = D or E
<220> FEATURE:
<221> NAME/KEY: MISC_FEATURE
<222> LOCATION: (10)..(10)
<223> OTHER INFORMATION: X = G or A

<400> SEQUENCE: 161

Xaa Xaa Ala Phe Arg Lys Ser Val Ala Xaa Gly Ala
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (1)..(1)
<223> OTHER INFORMATION: X = E or A
<220> FEATURE:
<221> NAME/KEY: MISC_FEATURE
<222> LOCATION: (2)..(2)
<223> OTHER INFORMATION: X = D or E
<220> FEATURE:
<221> NAME/KEY: MISC_FEATURE
<222> LOCATION: (6)..(6)
<223> OTHER INFORMATION: X = A or V
<220> FEATURE:
<221> NAME/KEY: MISC_FEATURE
<222> LOCATION: (10)..(10)
<223> OTHER INFORMATION: X = G or A

<400> SEQUENCE: 162

Xaa Xaa Ala Phe Arg Xaa Ser Val Ala Xaa Gly Ala
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (1)..(1)
<223> OTHER INFORMATION: X = A or E
<220> FEATURE:
<221> NAME/KEY: MISC_FEATURE
<222> LOCATION: (2)..(2)
<223> OTHER INFORMATION: X = D or E
<220> FEATURE:
<221> NAME/KEY: MISC_FEATURE
<222> LOCATION: (6)..(6)
<223> OTHER INFORMATION: X = A or V
```

```
<400> SEQUENCE: 163

Xaa Xaa Ala Phe Arg Xaa Ser Val Ala Glu Gly Ala
1               5                   10

<210> SEQ ID NO 164
<211> LENGTH: 11
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (10)..(10)
<223> OTHER INFORMATION: X= Q or A

<400> SEQUENCE: 164

Val Ala Glu Gly Ala Arg Pro Ala Phe Xaa Pro
1               5                   10

<210> SEQ ID NO 165
<211> LENGTH: 11
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (3)..(3)
<223> OTHER INFORMATION: X= A or G
<220> FEATURE:
<221> NAME/KEY: MISC_FEATURE
<222> LOCATION: (10)..(10)
<223> OTHER INFORMATION: X= Q or A

<400> SEQUENCE: 165

Val Ala Xaa Gly Ala Ile Pro Ala Phe Xaa Pro
1               5                   10

<210> SEQ ID NO 166
<211> LENGTH: 11
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (3)..(3)
<223> OTHER INFORMATION: X = A or G
<220> FEATURE:
<221> NAME/KEY: MISC_FEATURE
<222> LOCATION: (10)..(10)
<223> OTHER INFORMATION: X = Q or A

<400> SEQUENCE: 166

Val Ala Xaa Gly Ala Arg Ala Ala Phe Xaa Pro
1               5                   10

<210> SEQ ID NO 167
<211> LENGTH: 11
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (3)..(3)
<223> OTHER INFORMATION: X = A or G
<220> FEATURE:
<221> NAME/KEY: MISC_FEATURE
<222> LOCATION: (10)..(10)
<223> OTHER INFORMATION: X = Q or A
```

```
<400> SEQUENCE: 167

Val Ala Xaa Gly Ala Arg Pro Ala Gln Xaa Pro
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (3)..(3)
<223> OTHER INFORMATION: X = A or G

<400> SEQUENCE: 168

Val Ala Xaa Gly Ala Arg Pro Ala Phe Gly Pro
1               5                   10

<210> SEQ ID NO 169
<211> LENGTH: 9
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (5)..(5)
<223> OTHER INFORMATION: X=  W or R
<220> FEATURE:
<221> NAME/KEY: MISC_FEATURE
<222> LOCATION: (9)..(9)
<223> OTHER INFORMATION: X=  A or T

<400> SEQUENCE: 169

Phe His Glu Phe Xaa Glu Phe Thr Xaa
1               5

<210> SEQ ID NO 170
<211> LENGTH: 9
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (9)..(9)
<223> OTHER INFORMATION: X = A or T

<400> SEQUENCE: 170

Phe His Glu Phe Ala Glu Phe Asp Xaa
1               5

<210> SEQ ID NO 171
<211> LENGTH: 9
<212> TYPE: PRT
<213> ORGANISM: Artificial Sequence
<220> FEATURE:
<223> OTHER INFORMATION: Monocot plant HPPD modified consensus sequence

<400> SEQUENCE: 171

Phe His Glu Phe Ala Glu Phe Thr Asp
1               5

<210> SEQ ID NO 172
<211> LENGTH: 10
<212> TYPE: PRT
<213> ORGANISM: Artificial Sequence
```

```
<220> FEATURE:
<223> OTHER INFORMATION: Monocot plant HPPD modified consensus sequence
<220> FEATURE:
<221> NAME/KEY: MISC_FEATURE
<222> LOCATION: (2)..(2)
<223> OTHER INFORMATION: X= A or T
<220> FEATURE:
<221> NAME/KEY: MISC_FEATURE
<222> LOCATION: (8)..(8)
<223> OTHER INFORMATION: X= A or T

<400> SEQUENCE: 172

Asp Xaa Glu Asp Val Gly Thr Xaa Glu Ser
1               5                   10

<210> SEQ ID NO 173
<211> LENGTH: 10
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (8)..(8)
<223> OTHER INFORMATION: X = A or T

<400> SEQUENCE: 173

Thr Asp Glu Asp Val Gly Thr Xaa Glu Ser
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (2)..(2)
<223> OTHER INFORMATION: X = A or T
<220> FEATURE:
<221> NAME/KEY: MISC_FEATURE
<222> LOCATION: (8)..(8)
<223> OTHER INFORMATION: X = A or T
<220> FEATURE:
<221> NAME/KEY: MISC_FEATURE
<222> LOCATION: (9)..(9)
<223> OTHER INFORMATION: X = F or Y

<400> SEQUENCE: 174

Thr Xaa Glu Asp Val Gly Thr Xaa Xaa Ser
1               5                   10

<210> SEQ ID NO 175
<211> LENGTH: 13
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (8)..(8)
<223> OTHER INFORMATION: X = P, T or Q
<220> FEATURE:
<221> NAME/KEY: MISC_FEATURE
<222> LOCATION: (9)..(9)
<223> OTHER INFORMATION: X = S, P or A
<220> FEATURE:
<221> NAME/KEY: MISC_FEATURE
<222> LOCATION: (10)..(10)
<223> OTHER INFORMATION: X = D, N or K

<400> SEQUENCE: 175
```

```
Phe Glu Phe Ile Ala Pro Pro Xaa Xaa Xaa Tyr Tyr Trp
1               5                   10

<210> SEQ ID NO 176
<211> LENGTH: 13
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (4)..(4)
<223> OTHER INFORMATION: X = L or M
<220> FEATURE:
<221> NAME/KEY: MISC_FEATURE
<222> LOCATION: (8)..(8)
<223> OTHER INFORMATION: X = P, T or Q
<220> FEATURE:
<221> NAME/KEY: MISC_FEATURE
<222> LOCATION: (9)..(9)
<223> OTHER INFORMATION: X = S, P or A
<220> FEATURE:
<221> NAME/KEY: MISC_FEATURE
<222> LOCATION: (10)..(10)
<223> OTHER INFORMATION: X = D, N or K

<400> SEQUENCE: 176

Phe Glu Phe Xaa Asn Pro Pro Xaa Xaa Xaa Tyr Tyr Trp
1               5                   10

<210> SEQ ID NO 177
<211> LENGTH: 13
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (4)..(4)
<223> OTHER INFORMATION: X = L or M
<220> FEATURE:
<221> NAME/KEY: MISC_FEATURE
<222> LOCATION: (8)..(8)
<223> OTHER INFORMATION: X = P ,T or Q
<220> FEATURE:
<221> NAME/KEY: MISC_FEATURE
<222> LOCATION: (9)..(9)
<223> OTHER INFORMATION: X = S, P or A
<220> FEATURE:
<221> NAME/KEY: MISC_FEATURE
<222> LOCATION: (10)..(10)
<223> OTHER INFORMATION: X = D, N or K

<400> SEQUENCE: 177

Phe Glu Phe Xaa Ala Val Pro Xaa Xaa Xaa Tyr Tyr Trp
1               5                   10

<210> SEQ ID NO 178
<211> LENGTH: 13
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (4)..(4)
<223> OTHER INFORMATION: X = L or M
<220> FEATURE:
<221> NAME/KEY: MISC_FEATURE
<222> LOCATION: (9)..(9)
<223> OTHER INFORMATION: X = S, P or A
<220> FEATURE:
<221> NAME/KEY: MISC_FEATURE
```

```
<222> LOCATION: (10)..(10)
<223> OTHER INFORMATION: X = D, N or K

<400> SEQUENCE: 178

Phe Glu Phe Xaa Ala Pro Pro Gly Xaa Xaa Tyr Tyr Trp
1               5                   10

<210> SEQ ID NO 179
<211> LENGTH: 13
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (4)..(4)
<223> OTHER INFORMATION: X = L or M
<220> FEATURE:
<221> NAME/KEY: MISC_FEATURE
<222> LOCATION: (8)..(8)
<223> OTHER INFORMATION: X = P, T or Q
<220> FEATURE:
<221> NAME/KEY: MISC_FEATURE
<222> LOCATION: (10)..(10)
<223> OTHER INFORMATION: X = D, N or K

<400> SEQUENCE: 179

Phe Glu Phe Xaa Ala Pro Pro Xaa Gly Xaa Tyr Tyr Trp
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (4)..(4)
<223> OTHER INFORMATION: X = L or M
<220> FEATURE:
<221> NAME/KEY: MISC_FEATURE
<222> LOCATION: (8)..(8)
<223> OTHER INFORMATION: X = P, T or Q
<220> FEATURE:
<221> NAME/KEY: MISC_FEATURE
<222> LOCATION: (9)..(9)
<223> OTHER INFORMATION: X = D, N or K

<400> SEQUENCE: 180

Phe Glu Phe Xaa Ala Pro Pro Xaa Tyr Tyr Trp
1               5                   10

<210> SEQ ID NO 181
<211> LENGTH: 10
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (1)..(1)
<223> OTHER INFORMATION: X = D, N or K

<400> SEQUENCE: 181

Xaa Tyr Tyr Asp Gly Val Arg Arg Gly Val
1               5                   10

<210> SEQ ID NO 182
<211> LENGTH: 10
<212> TYPE: PRT
```

```
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (1)..(1)
<223> OTHER INFORMATION: X = D, N or K
<220> FEATURE:
<221> NAME/KEY: MISC_FEATURE
<222> LOCATION: (4)..(4)
<223> OTHER INFORMATION: X = D or E

<400> SEQUENCE: 182

Xaa Tyr Tyr Xaa Gly Val Arg Leu Gly Val
1               5                   10

<210> SEQ ID NO 183
<211> LENGTH: 8
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (4)..(4)
<223> OTHER INFORMATION: X = N or D

<400> SEQUENCE: 183

Gln Glu Leu Xaa Val Leu Val Asp
1               5

<210> SEQ ID NO 184
<211> LENGTH: 8
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (3)..(3)
<223> OTHER INFORMATION: X = Y or F

<400> SEQUENCE: 184

Val Asp Xaa Asp Asp Gln Gly Val
1               5

<210> SEQ ID NO 185
<211> LENGTH: 8
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (6)..(6)
<223> OTHER INFORMATION: X = A or G

<400> SEQUENCE: 185

Val Asp Arg Asp Asp Xaa Gly Val
1               5

<210> SEQ ID NO 186
<211> LENGTH: 9
<212> TYPE: PRT
<213> ORGANISM: Artificial Sequence
<220> FEATURE:
<223> OTHER INFORMATION: Monocot plant HPPD modified consensus sequence

<400> SEQUENCE: 186

Glu Met Ile Gln Arg Asn Gly Cys Met
```

```
<210> SEQ ID NO 187
<211> LENGTH: 9
<212> TYPE: PRT
<213> ORGANISM: Artificial Sequence
<220> FEATURE:
<223> OTHER INFORMATION: Monocot plant HPPD modified consensus sequence

<400> SEQUENCE: 187

Glu Met Ile Gln Arg Ile Asn Cys Met
1               5

<210> SEQ ID NO 188
<211> LENGTH: 9
<212> TYPE: PRT
<213> ORGANISM: Artificial Sequence
<220> FEATURE:
<223> OTHER INFORMATION: Monocot plant HPPD modified consensus sequence

<400> SEQUENCE: 188

Glu Met Ile Gln Arg Ile Gly Phe Met
1               5

<210> SEQ ID NO 189
<211> LENGTH: 9
<212> TYPE: PRT
<213> ORGANISM: Artificial Sequence
<220> FEATURE:
<223> OTHER INFORMATION: Monocot plant HPPD modified consensus sequence

<400> SEQUENCE: 189

Glu Met Ile Gln Arg Ile Gly Cys Gly
1               5

<210> SEQ ID NO 190
<211> LENGTH: 8
<212> TYPE: PRT
<213> ORGANISM: Artificial Sequence
<220> FEATURE:
<223> OTHER INFORMATION: Monocot plant HPPD modified consensus sequence

<400> SEQUENCE: 190

Glu Met Ile Gln Arg Ile Gly Cys
1               5

<210> SEQ ID NO 191
<211> LENGTH: 9
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (7)..(7)
<223> OTHER INFORMATION: X = K, S or V

<400> SEQUENCE: 191

Phe Met Glu Lys Asp Glu Xaa Gly Gln
1               5

<210> SEQ ID NO 192
<211> LENGTH: 9
<212> TYPE: PRT
<213> ORGANISM: Artificial Sequence
<220> FEATURE:
<223> OTHER INFORMATION: Monocot plant HPPD modified consensus sequence
<220> FEATURE:
```

```
<221> NAME/KEY: MISC_FEATURE
<222> LOCATION: (2)..(2)
<223> OTHER INFORMATION: X = T or V

<400> SEQUENCE: 192

Ala Xaa Val Glu Leu Tyr Gly Asp Val
1               5

<210> SEQ ID NO 193
<211> LENGTH: 7
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (2)..(2)
<223> OTHER INFORMATION: X = L or M
<220> FEATURE:
<221> NAME/KEY: MISC_FEATURE
<222> LOCATION: (4)..(4)
<223> OTHER INFORMATION: X = S or K
<220> FEATURE:
<221> NAME/KEY: MISC_FEATURE
<222> LOCATION: (5)..(5)
<223> OTHER INFORMATION: X = A or V
<220> FEATURE:
<221> NAME/KEY: MISC_FEATURE
<222> LOCATION: (6)..(6)
<223> OTHER INFORMATION: X = A or I
<220> FEATURE:
<221> NAME/KEY: MISC_FEATURE
<222> LOCATION: (7)..(7)
<223> OTHER INFORMATION: X = A or D

<400> SEQUENCE: 193

Glu Xaa Ala Xaa Xaa Xaa Xaa
1               5

<210> SEQ ID NO 194
<211> LENGTH: 7
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (1)..(1)
<223> OTHER INFORMATION: X = A or I
<220> FEATURE:
<221> NAME/KEY: MISC_FEATURE
<222> LOCATION: (2)..(2)
<223> OTHER INFORMATION: X = A or D
<220> FEATURE:
<221> NAME/KEY: MISC_FEATURE
<222> LOCATION: (4)..(4)
<223> OTHER INFORMATION: X = F, I or M
<220> FEATURE:
<221> NAME/KEY: MISC_FEATURE
<222> LOCATION: (5)..(5)
<223> OTHER INFORMATION: X = A, S or K
<220> FEATURE:
<221> NAME/KEY: MISC_FEATURE
<222> LOCATION: (6)..(6)
<223> OTHER INFORMATION: X = A, S or K

<400> SEQUENCE: 194

Xaa Xaa Phe Xaa Xaa Gly Phe
1               5

<210> SEQ ID NO 195
<211> LENGTH: 6
<212> TYPE: PRT
```

```
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (1)..(1)
<223> OTHER INFORMATION: X = F or V
<220> FEATURE:
<221> NAME/KEY: MISC_FEATURE
<222> LOCATION: (3)..(3)
<223> OTHER INFORMATION: X = A, D or Q
<220> FEATURE:
<221> NAME/KEY: MISC_FEATURE
<222> LOCATION: (4)..(4)
<223> OTHER INFORMATION: X = F, A or V

<400> SEQUENCE: 195

Xaa Val Xaa Xaa Asn Pro
1               5

<210> SEQ ID NO 196
<211> LENGTH: 10
<212> TYPE: PRT
<213> ORGANISM: Artificial Sequence
<220> FEATURE:
<223> OTHER INFORMATION: Monocot plant HPPD modified consensus sequence
<220> FEATURE:
<221> NAME/KEY: MISC_FEATURE
<222> LOCATION: (7)..(7)
<223> OTHER INFORMATION: X = E or S

<400> SEQUENCE: 196

Tyr Gln Lys Gly Ala Cys Xaa Gly Phe Gly
1               5                   10

<210> SEQ ID NO 197
<211> LENGTH: 9
<212> TYPE: PRT
<213> ORGANISM: Artificial Sequence
<220> FEATURE:
<223> OTHER INFORMATION: Monocot plant HPPD modified consensus sequence

<400> SEQUENCE: 197

Asp Val Val Leu Arg Phe Val Ser Tyr
1               5

<210> SEQ ID NO 198
<211> LENGTH: 7
<212> TYPE: PRT
<213> ORGANISM: Artificial Sequence
<220> FEATURE:
<223> OTHER INFORMATION: Monocot plant HPPD modified consensus sequence

<400> SEQUENCE: 198

Gly Phe Gly Ala Gly Asn Phe
1               5

<210> SEQ ID NO 199
<211> LENGTH: 8
<212> TYPE: PRT
<213> ORGANISM: Artificial Sequence
<220> FEATURE:
<223> OTHER INFORMATION: Dicot plant HPPD consensus sequence

<400> SEQUENCE: 199

Glu Glu Leu Gly Ile Leu Val Asp
1               5

<210> SEQ ID NO 200
```

-continued

```
<211> LENGTH: 8
<212> TYPE: PRT
<213> ORGANISM: Artificial Sequence
<220> FEATURE:
<223> OTHER INFORMATION: Dicot plant HPPD consensus sequence

<400> SEQUENCE: 200

Asp Val Val Leu Arg Tyr Val Ser
1               5

<210> SEQ ID NO 201
<211> LENGTH: 7
<212> TYPE: PRT
<213> ORGANISM: Artificial Sequence
<220> FEATURE:
<223> OTHER INFORMATION: Dicot plant HPPD consensus sequence

<400> SEQUENCE: 201

Gly Phe Gly Lys Gly Asn Phe
1               5

<210> SEQ ID NO 202
<211> LENGTH: 10
<212> TYPE: PRT
<213> ORGANISM: Artificial Sequence
<220> FEATURE:
<223> OTHER INFORMATION: Monocot plant HPPD consensus sequence

<400> SEQUENCE: 202

Tyr Gln Lys Gly Ala Cys Gly Gly Phe Gly
1               5                   10

<210> SEQ ID NO 203
<211> LENGTH: 9
<212> TYPE: PRT
<213> ORGANISM: Artificial Sequence
<220> FEATURE:
<223> OTHER INFORMATION: Monocot plant HPPD consensus sequence

<400> SEQUENCE: 203

Asp Val Val Leu Arg Tyr Val Ser Tyr
1               5

<210> SEQ ID NO 204
<211> LENGTH: 7
<212> TYPE: PRT
<213> ORGANISM: Artificial Sequence
<220> FEATURE:
<223> OTHER INFORMATION: Monocot plant HPPD consensus sequence

<400> SEQUENCE: 204

Gly Phe Gly Lys Gly Asn Phe
1               5

<210> SEQ ID NO 205
<211> LENGTH: 445
<212> TYPE: PRT
<213> ORGANISM: Arabidopsis thaliana

<400> SEQUENCE: 205

Met Gly His Gln Asn Ala Ala Val Ser Glu Asn Gln Asn His Asp Asp
1               5                   10                  15

Gly Ala Ala Ser Ser Pro Gly Phe Lys Leu Val Gly Phe Ser Lys Phe
                20                  25                  30

Val Arg Lys Asn Pro Lys Ser Asp Lys Phe Lys Val Lys Arg Phe His
            35                  40                  45
```

His Ile Glu Phe Trp Cys Gly Asp Ala Thr Asn Val Ala Arg Arg Phe
            50                  55                  60

Ser Trp Gly Leu Gly Met Arg Phe Ser Ala Lys Ser Asp Leu Ser Thr
65                  70                  75                  80

Gly Asn Met Val His Ala Ser Tyr Leu Leu Thr Ser Gly Asp Leu Arg
                85                  90                  95

Phe Leu Phe Thr Ala Pro Tyr Ser Pro Ser Leu Ser Ala Gly Glu Ile
                100                 105                 110

Lys Pro Thr Thr Thr Ala Ser Ile Pro Ser Phe Asp His Gly Ser Cys
                115                 120                 125

Arg Ser Phe Phe Ser Ser His Gly Leu Gly Val Arg Ala Val Ala Ile
                130                 135                 140

Glu Val Glu Asp Ala Glu Ser Ala Phe Ser Ile Ser Val Ala Asn Gly
145                 150                 155                 160

Ala Ile Pro Ser Ser Pro Pro Ile Val Leu Asn Glu Ala Val Thr Ile
                165                 170                 175

Ala Glu Val Lys Leu Tyr Gly Asp Val Val Leu Arg Tyr Val Ser Tyr
                180                 185                 190

Lys Ala Glu Asp Thr Glu Lys Ser Glu Phe Leu Pro Gly Phe Glu Arg
                195                 200                 205

Val Glu Asp Ala Ser Ser Phe Pro Leu Asp Tyr Gly Ile Arg Arg Leu
210                 215                 220

Asp His Ala Val Gly Asn Val Pro Glu Leu Gly Pro Ala Leu Thr Tyr
225                 230                 235                 240

Val Ala Gly Phe Thr Gly Phe His Gln Phe Ala Glu Phe Thr Ala Asp
                245                 250                 255

Asp Val Gly Thr Ala Glu Ser Gly Leu Asn Ser Ala Val Leu Ala Ser
                260                 265                 270

Asn Asp Glu Met Val Leu Leu Pro Ile Asn Glu Pro Val His Gly Thr
                275                 280                 285

Lys Arg Lys Ser Gln Ile Gln Thr Tyr Leu Glu His Asn Glu Gly Ala
                290                 295                 300

Gly Leu Gln His Leu Ala Leu Met Ser Glu Asp Ile Phe Arg Thr Leu
305                 310                 315                 320

Arg Glu Met Arg Lys Arg Ser Ser Ile Gly Gly Phe Asp Phe Met Pro
                325                 330                 335

Ser Pro Pro Thr Tyr Tyr Gln Asn Leu Lys Lys Arg Val Gly Asp
                340                 345                 350

Val Leu Ser Asp Asp Gln Ile Lys Glu Cys Glu Glu Leu Gly Ile Leu
                355                 360                 365

Val Asp Arg Asp Asp Gln Gly Thr Leu Leu Gln Ile Phe Thr Lys Pro
                370                 375                 380

Leu Gly Asp Arg Pro Thr Ile Phe Ile Glu Ile Ile Gln Arg Val Gly
385                 390                 395                 400

Cys Met Met Lys Asp Glu Glu Gly Lys Ala Tyr Gln Ser Gly Gly Cys
                405                 410                 415

Gly Gly Phe Gly Lys Gly Asn Phe Ser Glu Leu Phe Lys Ser Ile Glu
                420                 425                 430

Glu Tyr Glu Lys Thr Leu Glu Ala Lys Gln Leu Val Gly
                435                 440                 445

<210> SEQ ID NO 206
<211> LENGTH: 447

```
<212> TYPE: PRT
<213> ORGANISM: Glycine max

<400> SEQUENCE: 206

Met Pro Ile Pro Met Cys Asn Glu Ile Gln Ala Gln Ala Gln Ala Gln
1               5                   10                  15

Ala Gln Pro Gly Phe Lys Leu Val Gly Phe Lys Asn Phe Val Arg Thr
            20                  25                  30

Asn Pro Lys Ser Asp Arg Phe Gln Val Asn Arg Phe His His Ile Glu
        35                  40                  45

Phe Trp Cys Thr Asp Ala Thr Asn Ala Ser Arg Arg Phe Ser Trp Gly
    50                  55                  60

Leu Gly Met Pro Ile Val Ala Lys Ser Asp Leu Ser Thr Gly Asn Gln
65                  70                  75                  80

Ile His Ala Ser Tyr Leu Leu Arg Ser Gly Asp Leu Ser Phe Leu Phe
                85                  90                  95

Ser Ala Pro Tyr Ser Pro Ser Leu Ser Ala Gly Ser Ser Ala Ala Ser
            100                 105                 110

Ser Ala Ser Ile Pro Ser Phe Asp Ala Ala Thr Cys Leu Ala Phe Ala
        115                 120                 125

Ala Lys His Gly Phe Gly Val Arg Ala Ile Ala Leu Glu Val Ala Asp
    130                 135                 140

Ala Glu Ala Ala Phe Ser Ala Ser Val Ala Lys Gly Ala Glu Pro Ala
145                 150                 155                 160

Ser Pro Pro Val Leu Val Asp Asp Arg Thr Gly Phe Ala Glu Val Arg
                165                 170                 175

Leu Tyr Gly Asp Val Val Leu Arg Tyr Val Ser Tyr Lys Asp Ala Ala
            180                 185                 190

Pro Gln Ala Pro His Ala Asp Pro Ser Arg Trp Phe Leu Pro Gly Phe
        195                 200                 205

Glu Ala Ala Ala Ser Ser Ser Ser Phe Pro Glu Leu Asp Tyr Gly Ile
    210                 215                 220

Arg Arg Leu Asp His Ala Val Gly Asn Val Pro Glu Leu Ala Pro Ala
225                 230                 235                 240

Val Arg Tyr Leu Lys Gly Phe Ser Gly Phe His Glu Phe Ala Glu Phe
                245                 250                 255

Thr Ala Glu Asp Val Gly Thr Ser Glu Ser Gly Leu Asn Ser Val Val
            260                 265                 270

Leu Ala Asn Asn Ser Glu Thr Val Leu Leu Pro Leu Asn Glu Pro Val
        275                 280                 285

Tyr Gly Thr Lys Arg Lys Ser Gln Ile Glu Thr Tyr Leu Glu His Asn
    290                 295                 300

Glu Gly Ala Gly Val Gln His Leu Ala Leu Val Thr His Asp Ile Phe
305                 310                 315                 320

Thr Thr Leu Arg Glu Met Arg Lys Arg Ser Phe Leu Gly Gly Phe Glu
                325                 330                 335

Phe Met Pro Ser Pro Pro Pro Thr Tyr Tyr Ala Asn Leu His Asn Arg
            340                 345                 350

Ala Ala Asp Val Leu Thr Val Asp Gln Ile Lys Gln Cys Glu Glu Leu
        355                 360                 365

Gly Ile Leu Val Asp Arg Asp Asp Gln Gly Thr Leu Leu Gln Ile Phe
    370                 375                 380

Thr Lys Pro Val Gly Asp Arg Pro Thr Ile Phe Ile Glu Ile Ile Gln
385                 390                 395                 400
```

```
Arg Ile Gly Cys Met Val Glu Asp Glu Gly Lys Val Tyr Gln Lys
                405                 410                 415

Gly Ala Cys Gly Gly Phe Gly Lys Gly Asn Phe Ser Glu Leu Phe Lys
            420                 425                 430

Ser Ile Glu Glu Tyr Glu Lys Thr Leu Glu Ala Lys Arg Thr Ala
            435                 440                 445

<210> SEQ ID NO 207
<211> LENGTH: 447
<212> TYPE: PRT
<213> ORGANISM: Solanum tuberosum

<400> SEQUENCE: 207

Met Gly Lys Gln Ala Ala Thr Ala Thr Ala Thr Ala Thr Ala
1               5                   10                  15

Asp Asp Gln Gln Leu Pro Ala Asp Ile Glu Asp Lys Tyr Lys Leu Val
                20                  25                  30

Gly Phe Asn Asn Phe Val Arg Thr Asn Pro Arg Ser Asp Leu Phe Asn
            35                  40                  45

Val Lys Arg Phe His His Ile Glu Phe Trp Cys Gly Asp Ala Thr Asn
50                  55                  60

Thr Ala Arg Arg Phe Ser Trp Gly Leu Gly Leu Pro Ile Ala Ala Lys
65                  70                  75                  80

Ser Asp Leu Ser Thr Gly Asn Ser Val His Ala Ser Tyr Leu Leu Arg
                85                  90                  95

Ser Ser Ser Ser Gln Leu Gln Phe Leu Phe Thr Ala Pro Tyr Ser Pro
            100                 105                 110

Ala Ile Ser Thr Pro Ser Ser Ser Ile Pro Thr Phe Ser Val Ser
            115                 120                 125

Ser His Arg Ser Phe Thr Glu Thr His Gly Leu Gly Val Arg Ala Ile
    130                 135                 140

Ala Leu Glu Val Glu Asn Ser Arg Leu Ala Phe Ser Thr Cys Val Ser
145                 150                 155                 160

His Gly Ala Lys Pro Val Ser Glu Pro Val Ile Leu Asn Asp Glu Val
                165                 170                 175

Val Ile Ser Glu Val His Leu Tyr Gly Asp Val Val Leu Arg Phe Val
            180                 185                 190

Ser Phe Leu Lys Asp Ser Asn Arg Phe Val Phe Leu Pro Gly Phe Glu
        195                 200                 205

Leu Val Glu Gly Ala Gln Leu Asp Tyr Gly Ile Arg Arg Leu Asp His
    210                 215                 220

Ala Val Gly Asn Val Pro Gln Leu Gly Pro Val Val Glu Tyr Ile Lys
225                 230                 235                 240

Ser Phe Thr Gly Phe His Glu Phe Ala Glu Phe Thr Ala Glu Asp Val
                245                 250                 255

Gly Thr Ala Glu Ser Gly Leu Asn Ser Val Val Leu Ala Asn Asn Asp
            260                 265                 270

Glu Thr Val Leu Phe Pro Leu Asn Glu Pro Val Tyr Gly Thr Lys Arg
        275                 280                 285

Lys Ser Gln Ile Gln Thr Tyr Leu Glu His Asn Glu Gly Ala Gly Val
    290                 295                 300

Gln His Leu Ala Leu Val Thr Glu Asp Ile Phe Arg Thr Leu Arg Glu
305                 310                 315                 320

Met Arg Lys Arg Ser Gly Ile Gly Gly Phe Glu Phe Met Pro Ser Pro
```

```
                    325                 330                 335
Pro Pro Thr Tyr Tyr Lys Asn Leu Lys Ser Arg Ala Gly Asp Ile Leu
                340                 345                 350

Ser Asp Glu Gln Ile Lys Glu Cys Glu Glu Leu Gly Ile Leu Val Asp
                355                 360                 365

Arg Asp Asp Gln Gly Thr Leu Leu Gln Ile Phe Thr Lys Pro Val Gly
            370                 375                 380

Asp Arg Pro Thr Ile Phe Leu Glu Ile Ile Gln Arg Ile Gly Cys Met
385                 390                 395                 400

Leu Gln Asn Ala Glu Gly Leu Tyr Gln Lys Gly Cys Gly Gly
                405                 410                 415

Phe Gly Lys Gly Asn Phe Ser Glu Leu Phe Lys Ser Ile Glu Glu Tyr
                420                 425                 430

Glu Lys Thr Leu Glu Ala Lys Gln Asn Thr Gln Val Ala Ile Ala
                435                 440                 445

<210> SEQ ID NO 208
<211> LENGTH: 440
<212> TYPE: PRT
<213> ORGANISM: Brassica napus

<400> SEQUENCE: 208

Met Gly His Glu Asn Ala Ala Val Ser Glu Ser Gln His His Asp Asp
1               5                   10                  15

Ala Ala Ser Ala Ala Ser Pro Gly Phe Lys Leu Val Gly Phe Ser Lys
                20                  25                  30

Phe Val Arg Lys Asn Pro Lys Ser Asp Lys Phe Lys Val Lys Arg Phe
            35                  40                  45

His His Ile Glu Phe Trp Cys Gly Asp Ala Thr Asn Val Ala Arg Arg
        50                  55                  60

Phe Ser Trp Gly Leu Gly Met Arg Phe Ser Ala Lys Ser Asp Leu Ser
65                  70                  75                  80

Thr Gly Asn Met Val His Ala Ser Tyr Leu Leu Thr Ser Gly Asp Leu
                85                  90                  95

Arg Phe Leu Phe Thr Ala Pro Tyr Ser Pro Ser Leu Ser Ala Gly Glu
            100                 105                 110

Thr Ser Thr Ala Ser Ile Pro Ser Phe Asp His Val Ser Cys Arg Ser
        115                 120                 125

Phe Phe Ser Ser His Gly Leu Gly Val Arg Ala Val Ala Ile Glu Val
    130                 135                 140

Glu Asp Ala Glu Ser Ala Phe Ser Ile Ser Val Ala Asn Gly Ala Val
145                 150                 155                 160

Pro Ser Ser Pro Pro Asn Val Leu Asn Gly Ala Val Thr Ile Ala Glu
                165                 170                 175

Val Lys Leu Tyr Gly Asp Val Leu Arg Tyr Val Ser Tyr His Asn
            180                 185                 190

Gly Ala Val Asn Phe Leu Pro Gly Phe Glu Ser Val Asp Asp Thr Ser
        195                 200                 205

Ser Phe Pro Leu Asp Tyr Gly Ile Arg Arg Leu Asp His Ala Val Gly
    210                 215                 220

Asn Val Pro Glu Leu Gly Pro Ala Leu Thr Tyr Leu Ala Gly Phe Thr
225                 230                 235                 240

Gly Phe His Gln Phe Ala Glu Phe Thr Ala Asp Asp Val Gly Thr Ala
                245                 250                 255
```

-continued

```
Glu Ser Gly Leu Asn Ser Ala Val Leu Ala Asn Asn Asp Glu Met Val
                260                 265                 270

Leu Leu Pro Val Asn Glu Pro Val His Gly Thr Lys Arg Lys Ser Gln
            275                 280                 285

Ile Gln Thr Phe Leu Glu His Asn Glu Gly Ala Gly Leu Gln His Leu
        290                 295                 300

Ala Leu Met Ser Glu Asp Ile Phe Arg Thr Leu Arg Glu Met Arg Lys
305                 310                 315                 320

Arg Ser Gly Val Gly Gly Phe Asp Phe Met Pro Ser Pro Pro Pro Thr
                325                 330                 335

Tyr Tyr Lys Asn Leu Lys Lys Arg Ile Gly Asp Val Leu Ser Asp Glu
            340                 345                 350

Gln Ile Arg Glu Cys Glu Glu Leu Gly Ile Leu Val Asp Arg Asp Asp
        355                 360                 365

Gln Gly Thr Leu Leu Gln Ile Phe Thr Lys Pro Leu Gly Asp Arg Pro
370                 375                 380

Thr Ile Phe Ile Glu Ile Ile Gln Arg Val Gly Cys Met Lys Lys Asp
385                 390                 395                 400

Glu Glu Gly Lys Val Tyr Gln Ser Gly Gly Cys Gly Gly Phe Gly Lys
                405                 410                 415

Gly Asn Phe Ser Glu Leu Phe Lys Ser Ile Glu Glu Tyr Glu Lys Thr
            420                 425                 430

Leu Glu Ala Lys Gln Leu Val Gly
            435                 440

<210> SEQ ID NO 209
<211> LENGTH: 435
<212> TYPE: PRT
<213> ORGANISM: Medicago sativa

<400> SEQUENCE: 209

Met Ala Ile Glu Thr Glu Thr Gln Thr Gln Thr Gly Phe Lys Leu Val
1               5                   10                  15

Gly Phe Lys Asn Phe Val Arg Ala Asn Pro Lys Ser Asp Arg Phe Lys
            20                  25                  30

Val Lys Arg Phe His His Val Glu Phe Trp Cys Thr Asp Ala Thr Asn
        35                  40                  45

Thr Ala Arg Arg Phe Ser His Gly Leu Gly Met Pro Ile Val Ala Lys
    50                  55                  60

Ser Asp Leu Ser Thr Gly Asn Gln Thr His Ala Ser Tyr Leu Leu Arg
65                  70                  75                  80

Ser Gly Asp Leu Asn Phe Leu Phe Ser Ala Ala Tyr Ser Pro Ser Ile
                85                  90                  95

Ser Leu Ser Ser Pro Ser Ser Thr Ala Ala Ile Pro Thr Phe Ser Ala
            100                 105                 110

Ser Asn Cys Phe Ser Phe Ser Ala Ser His Gly Leu Ala Val Arg Ala
        115                 120                 125

Val Ala Val Glu Val Glu Asp Ala Glu Leu Ala Phe Thr Thr Ser Val
    130                 135                 140

Asn Asn Gly Ala Ile Pro Ser Ser Pro Val Ile Leu Glu Asn His
145                 150                 155                 160

Val Lys Leu Ala Glu Val Arg Leu Tyr Gly Asp Val Val Leu Arg Tyr
                165                 170                 175

Val Ser Tyr Asn Asp Pro Asn Pro Asn Gln Asn Pro Asn Leu Leu Phe
            180                 185                 190
```

```
Leu Pro Gly Phe Glu Arg Val Ser Asp Glu Ser Ser Asn Ser Ser Leu
            195                 200                 205

Asp Phe Gly Ile Arg Arg Leu Asp His Ala Val Gly Asn Val Pro Glu
210                 215                 220

Leu Ser Ala Val Lys Tyr Val Lys Asp Phe Thr Gly Phe His Glu
225                 230                 235                 240

Phe Ala Glu Phe Thr Ala Glu Asp Val Gly Thr Ser Glu Ser Gly Leu
            245                 250                 255

Asn Ser Val Val Leu Ala Asn Asn Glu Glu Thr Val Leu Leu Pro Met
            260                 265                 270

Asn Glu Pro Val Tyr Gly Thr Lys Arg Lys Ser Gln Ile Glu Thr Tyr
            275                 280                 285

Leu Glu His Asn Glu Gly Ala Gly Leu Gln His Leu Ala Leu Lys Ser
            290                 295                 300

Glu Asp Ile Phe Arg Thr Leu Arg Glu Met Arg Lys Arg Ser Gly Val
305                 310                 315                 320

Gly Gly Phe Glu Phe Met Pro Ser Pro Val Thr Tyr Tyr Arg Asn
            325                 330                 335

Leu Lys Asn Arg Val Gly Asp Val Leu Ser Asp Glu Gln Ile Lys Glu
            340                 345                 350

Cys Glu Glu Leu Gly Ile Leu Val Asp Arg Asp Asp Gln Gly Thr Leu
            355                 360                 365

Leu Gln Ile Phe Thr Lys Pro Ile Gly Asp Arg Pro Thr Ile Phe Ile
            370                 375                 380

Glu Ile Ile Gln Arg Val Gly Cys Met Leu Lys Asp Glu Glu Gly Lys
385                 390                 395                 400

Glu Tyr Gln Lys Gly Gly Cys Gly Gly Phe Gly Lys Gly Asn Phe Ser
            405                 410                 415

Glu Leu Phe Lys Ser Ile Glu Glu Tyr Glu Lys Thr Leu Glu Thr Arg
            420                 425                 430

Arg Thr Ala
        435

<210> SEQ ID NO 210
<211> LENGTH: 436
<212> TYPE: PRT
<213> ORGANISM: Gossypium hirsutum

<400> SEQUENCE: 210

Met Val Gln Thr Asn Gln Ser Gly Ser Gly Asn Asp Phe Lys Leu Val
1               5                   10                  15

Gly Phe Ser Asn Phe Val Arg Ser Asn Pro Lys Ser Asp Arg Phe Thr
            20                  25                  30

Val Lys Arg Phe His His Ile Glu Phe Trp Cys Thr Asp Ala Thr Asn
        35                  40                  45

Val Ala Arg Arg Phe Ser Trp Gly Leu Gly Met Gln Phe Val Ala Lys
    50                  55                  60

Ser Asp Leu Ser Thr Gly Asn Leu Thr His Ala Ser Tyr Leu Leu Arg
65              70                  75                  80

Ser Arg Asp Leu Asn Phe Leu Phe Thr Ala Pro Tyr Ser Pro Ser Ile
                85                  90                  95

Ala Val Ala Gln Asn Leu Ser Pro Gln Ser Thr Ala Ser Ile Pro Ser
            100                 105                 110

Phe Asp His Ser Leu Cys Arg Ser Phe Ala Ala Thr His Gly Leu Gly
```

```
            115                 120                 125
Val Arg Ala Ile Ala Ile Glu Val Asp Asp Ala Glu Thr Ala Phe Thr
    130                 135                 140

Thr Ser Val Thr His Gly Ala Leu Pro Phe Cys Pro Pro Thr Pro Leu
145                 150                 155                 160

Gly Asp Val Ala Thr Ile Ala Glu Val Lys Leu Tyr Gly Asp Val Val
                165                 170                 175

Leu Arg Tyr Val Ser Tyr Thr Thr Thr Ile Asn Ser Asp His Asp Phe
                180                 185                 190

Leu Pro Gly Phe Glu Lys Ile Glu Asp Thr Leu Ser Tyr Pro Leu Asp
                195                 200                 205

Tyr Gly Leu Arg Arg Leu Asp His Ala Val Gly Asn Val Pro Glu Leu
    210                 215                 220

Gly Pro Ala Val Ser Tyr Val Lys Ser Phe Thr Gly Phe His Glu Phe
225                 230                 235                 240

Ala Glu Phe Thr Ala Glu Asp Val Gly Thr Ser Glu Ser Gly Leu Asn
                245                 250                 255

Ser Val Val Leu Ala Asn Asn Glu Glu Met Val Leu Leu Pro Met Asn
                260                 265                 270

Glu Pro Val Phe Gly Thr Lys Arg Lys Ser Gln Ile Gln Thr Tyr Leu
                275                 280                 285

Glu His Asn Glu Gly Ala Gly Val Gln His Leu Ala Leu Val Ser Glu
                290                 295                 300

Asp Ile Phe Lys Thr Leu Arg Glu Met Arg Lys Arg Ser Phe Val Gly
305                 310                 315                 320

Gly Phe Glu Phe Met Pro Ser Pro Pro Thr Tyr Tyr Lys Lys Leu
                325                 330                 335

Lys Gln Arg Ala Gly Asp Ile Leu Ser Asp Glu Gln Ile Lys Glu Cys
                340                 345                 350

Glu Glu Leu Gly Ile Leu Val Asp Arg Asp Asp Gln Gly Thr Leu Leu
                355                 360                 365

Gln Ile Phe Thr Lys Pro Val Gly Asp Arg Pro Thr Ile Phe Ile Glu
    370                 375                 380

Ile Ile Gln Arg Ile Gly Cys Met Val Lys Asp Glu Glu Gly Lys Gln
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Glu Tyr Glu Lys Ser Leu Glu Ala Lys Gln
                420                 425                 430

Ser Gln Asn Pro
        435

<210> SEQ ID NO 211
<211> LENGTH: 434
<212> TYPE: PRT
<213> ORGANISM: Beta vulgaris

<400> SEQUENCE: 211

Met Gly Thr Leu Ser Pro Gln Pro Gln Thr Ser Pro Ser Gln Phe Lys
1               5                   10                  15

Leu Val Gly Tyr Ser Asn Phe Ile Arg Val Asn Pro Leu Ser Asp Leu
                20                  25                  30

Phe Pro Val Lys Arg Phe His His Val Glu Phe Trp Cys Gly Asp Ala
                35                  40                  45
```

Thr Asn Val Ser Arg Arg Phe Ser Trp Gly Leu Gly Met Pro Ile Val
 50                  55                  60

Ala Lys Ser Asp Leu Ser Thr Gly Asn Ser Val His Ala Ser Tyr Leu
 65                  70                  75                  80

Leu Arg Ser Gly Glu Leu His Phe Leu Phe Thr Ser Pro Tyr Ser Pro
                 85                  90                  95

Ser Leu Ser Ser Pro Ser Ser Ala Thr Ile Pro Thr Phe Ser Phe Ser
            100                 105                 110

Leu Phe Thr Ser Phe Leu Thr Ser His Gly Leu Ala Val Arg Ala Val
            115                 120                 125

Ala Val Glu Val Gln Asp Ala Glu Ala Ala Phe His Ile Ser Val Ser
130                 135                 140

Asn Gly Ala Ser Pro Val Ser Pro Pro Ile Arg Leu His Asp Gly Val
145                 150                 155                 160

Val Leu Ser Glu Val His Leu Tyr Gly Asp Val Val Leu Arg Tyr Val
                165                 170                 175

Ser Thr Ser Ser Val Val Asp Gly Ile Phe Leu Pro Gly Phe Glu Glu
            180                 185                 190

Met Leu Gly Glu Ser Ser Phe Gln Glu Leu Asp Phe Gly Leu Arg Arg
            195                 200                 205

Leu Asp His Ala Val Gly Asn Val Pro Glu Leu Ala Pro Ala Ile Glu
210                 215                 220

Tyr Val Lys Lys Phe Thr Gly Phe His Glu Phe Ala Glu Phe Thr Thr
225                 230                 235                 240

Glu Asp Val Gly Thr Ser Glu Ser Gly Leu Asn Ser Ala Val Val Ala
                245                 250                 255

Asn Asn Asp Glu Thr Val Leu Phe Pro Met Asn Glu Pro Val Tyr Gly
            260                 265                 270

Thr Lys Arg Lys Ser Gln Ile Gln Thr Tyr Leu Glu His Asn Glu Gly
            275                 280                 285

Ala Gly Val Gln His Leu Ala Leu Met Ser Glu Asp Ile Phe Trp Thr
290                 295                 300

Leu Arg Glu Met Arg Lys Arg Ser Gly Leu Gly Gly Phe Glu Phe Met
305                 310                 315                 320

Pro Ser Pro Pro Thr Tyr Tyr Arg Asn Leu Arg Asn Arg Ala Ala
                325                 330                 335

Asp Val Leu Ser Glu Glu Gln Met Lys Glu Cys Glu Glu Leu Gly Ile
            340                 345                 350

Leu Val Asp Lys Asp Asp Gln Gly Thr Leu Leu Gln Ile Phe Thr Lys
            355                 360                 365

Pro Ile Gly Asp Arg Pro Thr Met Phe Ile Glu Ile Ile Gln Arg Ile
370                 375                 380

Gly Cys Met Met Lys Asp Glu Glu Gly Lys Val Tyr Gln Lys Gly Gly
385                 390                 395                 400

Cys Gly Gly Phe Gly Lys Gly Asn Phe Ser Glu Leu Phe Lys Ser Ile
                405                 410                 415

Glu Glu Tyr Glu Lys Thr Leu Glu Arg Lys Pro Ile Ala Asp Thr Asn
            420                 425                 430

Ala Thr

<210> SEQ ID NO 212
<211> LENGTH: 418
<212> TYPE: PRT
<213> ORGANISM: Zea mays

<400> SEQUENCE: 212

```
Ala Ser Ala Ala Glu Gln Ala Ala Phe Arg Leu Val Gly His Arg Asn
1               5                   10                  15

Phe Val Arg Phe Asn Pro Arg Ser Asp Arg Phe His Thr Leu Ala Phe
            20                  25                  30

His His Val Glu Leu Trp Cys Ala Asp Ala Ser Ala Ala Gly Arg
        35                  40                  45

Phe Ser Phe Gly Leu Gly Ala Pro Leu Ala Ala Arg Ser Asp Leu Ser
    50                  55                  60

Thr Gly Asn Ser Ala His Ala Ser Leu Leu Arg Ser Gly Ser Leu
65                  70                  75                  80

Ser Phe Leu Phe Thr Ala Pro Tyr Ala His Gly Ala Asp Ala Ala Thr
                85                  90                  95

Ala Ala Leu Pro Ser Phe Ser Ala Ala Ala Arg Arg Phe Ala Ala
                100                 105                 110

Asp His Gly Leu Ala Val Arg Ala Val Ala Leu Arg Val Ala Asp Ala
                115                 120                 125

Glu Asp Ala Phe Arg Ala Ser Val Ala Ala Gly Ala Arg Pro Ala Phe
        130                 135                 140

Gly Pro Val Asp Leu Gly Arg Gly Phe Arg Leu Ala Glu Val Glu Leu
145                 150                 155                 160

Tyr Gly Asp Val Val Leu Arg Tyr Val Ser Tyr Pro Asp Gly Ala Ala
                165                 170                 175

Gly Glu Pro Phe Leu Pro Gly Phe Glu Gly Val Ala Ser Pro Gly Ala
                180                 185                 190

Ala Asp Tyr Gly Leu Ser Arg Phe Asp His Ile Val Gly Asn Val Pro
        195                 200                 205

Glu Leu Ala Pro Ala Ala Tyr Phe Ala Gly Phe Thr Gly Phe His
210                 215                 220

Glu Phe Ala Glu Phe Thr Thr Glu Asp Val Gly Thr Ala Glu Ser Gly
225                 230                 235                 240

Leu Asn Ser Met Val Leu Ala Asn Asn Ser Glu Asn Val Leu Leu Pro
                245                 250                 255

Leu Asn Glu Pro Val His Gly Thr Lys Arg Arg Ser Gln Ile Gln Thr
                260                 265                 270

Phe Leu Asp His His Gly Gly Pro Gly Val Gln His Met Ala Leu Ala
        275                 280                 285

Ser Asp Asp Val Leu Arg Thr Leu Arg Glu Met Gln Ala Arg Ser Ala
    290                 295                 300

Met Gly Gly Phe Glu Phe Met Ala Pro Pro Thr Ser Asp Tyr Tyr Asp
305                 310                 315                 320

Gly Val Arg Arg Arg Ala Gly Asp Val Leu Thr Glu Ala Gln Ile Lys
                325                 330                 335

Glu Cys Gln Glu Leu Gly Val Leu Val Asp Arg Asp Gln Gly Val
                340                 345                 350

Leu Leu Gln Ile Phe Thr Lys Pro Val Gly Asp Arg Pro Thr Leu Phe
        355                 360                 365

Leu Glu Ile Ile Gln Arg Ile Gly Cys Met Glu Lys Asp Glu Lys Gly
    370                 375                 380

Gln Glu Tyr Gln Lys Gly Gly Cys Gly Gly Phe Gly Lys Gly Asn Phe
385                 390                 395                 400

Ser Gln Leu Phe Lys Ser Ile Glu Asp Tyr Glu Lys Ser Leu Glu Ala
```

Lys Gln

<210> SEQ ID NO 213
<211> LENGTH: 446
<212> TYPE: PRT
<213> ORGANISM: Oryza sativa

<400> SEQUENCE: 213

```
Met Pro Pro Thr Pro Thr Pro Thr Ala Thr Gly Ala Val Ser Ala
1               5                   10                  15

Ala Ala Ala Ala Gly Glu Asn Ala Gly Phe Arg Leu Val Gly His Arg
            20                  25                  30

Arg Phe Val Arg Ala Asn Pro Arg Ser Asp Arg Phe Gln Ala Leu Ala
        35                  40                  45

Phe His His Val Glu Leu Trp Cys Ala Asp Ala Ala Ser Ala Ala Gly
    50                  55                  60

Arg Phe Ala Phe Ala Leu Gly Ala Pro Leu Ala Ala Arg Ser Asp Leu
65                  70                  75                  80

Ser Thr Gly Asn Ser Ala His Ala Ser Leu Leu Arg Ser Ala Ser
                85                  90                  95

Val Ala Phe Leu Phe Thr Ala Pro Tyr Gly Gly Asp His Gly Val Gly
            100                 105                 110

Ala Asp Ala Ala Thr Thr Ala Ser Ile Pro Ser Phe Ser Pro Gly Ala
        115                 120                 125

Ala Arg Arg Phe Ala Ala Asp His Gly Leu Ala Val His Ala Val Ala
    130                 135                 140

Leu Arg Val Ala Asp Ala Ala Asp Ala Phe Arg Ala Ser Val Ala Ala
145                 150                 155                 160

Gly Ala Arg Pro Ala Phe Gln Pro Ala Asp Leu Gly Gly Phe Gly
                165                 170                 175

Leu Ala Glu Val Glu Leu Tyr Gly Asp Val Val Leu Arg Phe Val Ser
            180                 185                 190

His Pro Asp Gly Ala Asp Ala Pro Phe Leu Pro Gly Phe Glu Gly Val
        195                 200                 205

Ser Asn Pro Gly Ala Val Asp Tyr Gly Leu Arg Arg Phe Asp His Val
    210                 215                 220

Val Gly Asn Val Pro Glu Leu Ala Pro Val Ala Ala Tyr Ile Ser Gly
225                 230                 235                 240

Phe Thr Gly Phe His Glu Phe Ala Glu Phe Thr Ala Glu Asp Val Gly
                245                 250                 255

Thr Ala Glu Ser Gly Leu Asn Ser Val Val Leu Ala Asn Asn Ala Glu
            260                 265                 270

Thr Val Leu Leu Pro Leu Asn Glu Pro Val His Gly Thr Lys Arg Arg
        275                 280                 285

Ser Gln Ile Gln Thr Tyr Leu Asp His Gly Gly Pro Gly Val Gln
    290                 295                 300

His Ile Ala Leu Ala Ser Asp Asp Val Leu Gly Thr Leu Arg Glu Met
305                 310                 315                 320

Arg Ala Arg Ser Ala Met Gly Gly Phe Glu Phe Leu Ala Pro Pro Pro
                325                 330                 335

Pro Asn Tyr Tyr Asp Gly Val Arg Arg Ala Gly Asp Val Leu Ser
            340                 345                 350

Glu Glu Gln Ile Asn Glu Cys Gln Glu Leu Gly Val Leu Val Asp Arg
```

```
            355                 360                 365
Asp Asp Gln Gly Val Leu Leu Gln Ile Phe Thr Lys Pro Val Gly Asp
    370                 375                 380

Arg Pro Thr Phe Phe Leu Glu Met Ile Gln Arg Ile Gly Cys Met Glu
385                 390                 395                 400

Lys Asp Glu Ser Gly Gln Glu Tyr Gln Lys Gly Gly Cys Gly Gly Phe
                405                 410                 415

Gly Lys Gly Asn Phe Ser Glu Leu Phe Lys Ser Ile Glu Glu Tyr Glu
            420                 425                 430

Lys Ser Leu Glu Ala Lys Gln Ala Pro Thr Val Gln Gly Ser
        435                 440                 445

<210> SEQ ID NO 214
<211> LENGTH: 440
<212> TYPE: PRT
<213> ORGANISM: Artificial Sequence
<220> FEATURE:
<223> OTHER INFORMATION: Artificial sequence

<400> SEQUENCE: 214

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Ala Ala Thr
            100                 105                 110

Ala Ser Ile Pro Ser Phe Ser Ala Asp Ala Ala Arg Thr Phe Ala Ala
        115                 120                 125

Ala His Gly Leu Ala Val Arg Ser Val Gly Val Arg Val Ala Asp Ala
    130                 135                 140

Ala Glu Ala Phe Arg Val Ser Val Ala Gly Gly Ala Arg Pro Ala Phe
145                 150                 155                 160

Ala Pro Ala Asp Leu Gly His Gly Phe Gly Leu Ala Glu Val Glu Leu
                165                 170                 175

Tyr Gly Asp Val Val Leu Arg Phe Val Ser Tyr Pro Asp Glu Thr Asp
            180                 185                 190

Leu Pro Phe Leu Pro Gly Phe Glu Arg Val Ser Ser Pro Gly Ala Val
        195                 200                 205

Asp Tyr Gly Leu Thr Arg Phe Asp His Val Val Gly Asn Val Pro Glu
    210                 215                 220

Met Ala Pro Val Ile Asp Tyr Met Lys Gly Phe Leu Gly Phe His Glu
225                 230                 235                 240

Phe Ala Glu Phe Thr Ala Glu Asp Val Gly Thr Thr Glu Ser Gly Leu
                245                 250                 255

Asn Ser Val Val Leu Ala Asn Asn Ser Glu Ala Val Leu Leu Pro Leu
            260                 265                 270

Asn Glu Pro Val His Gly Thr Lys Arg Arg Ser Gln Ile Gln Thr Tyr
```

```
                      275                 280                 285
Leu Glu Tyr His Gly Gly Pro Gly Val Gln His Ile Ala Leu Ala Ser
        290                 295                 300

Asn Asp Val Leu Arg Thr Leu Arg Glu Met Arg Ala Arg Thr Pro Met
305                 310                 315                 320

Gly Gly Phe Glu Phe Met Ala Pro Pro Gln Ala Lys Tyr Tyr Glu Gly
                325                 330                 335

Val Arg Arg Ile Ala Gly Asp Val Leu Ser Glu Glu Gln Ile Lys Glu
                340                 345                 350

Cys Gln Glu Leu Gly Val Leu Val Asp Arg Asp Gln Gly Val Leu
                355                 360                 365

Leu Gln Ile Phe Thr Lys Pro Val Gly Asp Arg Pro Thr Phe Phe Leu
        370                 375                 380

Glu Met Ile Gln Arg Ile Gly Cys Met Glu Lys Asp Glu Val Gly Gln
385                 390                 395                 400

Glu Tyr Gln Lys Gly Gly Cys Gly Gly Phe Gly Lys Gly Asn Phe Ser
                405                 410                 415

Glu Leu Phe Lys Ser Ile Glu Asp Tyr Glu Lys Ser Leu Glu Val Lys
                420                 425                 430

Gln Ser Val Val Ala Gln Lys Ser
                435                 440
```